United States Patent [19]

Hayashi et al.

[11] 4,180,675
[45] Dec. 25, 1979

[54] 15-CYCLOALKYL-PROSTAGLANDIN DERIVATIVES

[75] Inventors: Masaki Hayashi; Seiji Kori, both of Takatsuki; Isao Ohyama, Osaka; Sadahiko Iguchi, Tsuzuki; Takanori Okada, Osaka, all of Japan

[73] Assignee: Warner-Lambert Company, Morris Plains, N.J.

[21] Appl. No.: 857,341

[22] Filed: Dec. 5, 1977

Related U.S. Application Data

[62] Division of Ser. No. 703,158, Jul. 7, 1976, Pat. No. 4,087,620.

[30] Foreign Application Priority Data

Jul. 17, 1975 [GB] United Kingdom .............. 30072/75
May 6, 1976 [GB] United Kingdom .............. 18651/76

[51] Int. Cl.$^2$ ............................................. C07C 177/00
[52] U.S. Cl. ..................................... 560/118; 562/500
[58] Field of Search ........................ 560/118; 562/500

[56] References Cited

U.S. PATENT DOCUMENTS

| 4,028,396 | 6/1977 | Schaub et al. ...................... 260/468 |
| 4,034,003 | 7/1977 | Hayashi et al. .................... 260/514 |
| 4,045,468 | 8/1977 | Kurono et al. ...................... 260/468 |

Primary Examiner—Robert Gerstl
Attorney, Agent, or Firm—Albert H. Graddis

[57] ABSTRACT

The present invention relates to 15-cycloalkyl-prostaglandins of the formula:

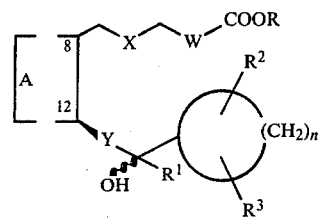

wherein A represents a grouping of the formula:

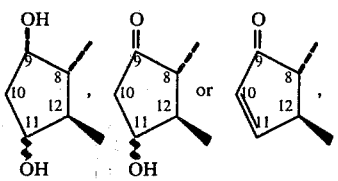

W represents ethylene or trans-vinylene, X represents ethylene or cis-vinylene, Y represents ethylene or trans-vinylene, R represents a hydrogen atom or a straight- or branched-chain alkyl group containing from 1 to 12 carbon atoms, $R^1$ represents a hydrogen atom or a methyl or ethyl group, $R^2$ represents a straight- or branched-chain alkyl group containing from 2 to 8 carbon atoms or a phenyl group unsubstituted or substituted by an alkyl group containing from 1 to 3 carbon atoms, $R^3$ represents a hydrogen atom or a straight- or branched-chain alkyl group containing from 1 to 3 carbon atoms, and n represents 4 or 5 and cyclodextrin clathrates of such acids and esters and, when R represents a hydrogen atom, non-toxic salts thereof.

These new compounds exhibit characteristic prostaglandin-like activities.

13 Claims, No Drawings

15-CYCLOALKYL-PROSTAGLANDIN DERIVATIVES

This is a division, of application Ser. No. 703,158 filed July 7, 1976, now U.S. Pat. No. 4,087,620.

This invention is concerned with new prostaglandin analogues.

Prostaglandins are derivatives of prostanoic acid which has the following formula:

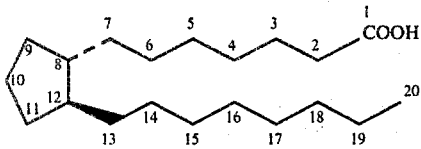

Various types of prostaglandins are known, the types depending inter alia on the structure and substituents on the alicyclic ring. For example, the alicylic rings of prostaglandins F(PGF), E(PGE) and A(PGA) have the structures:

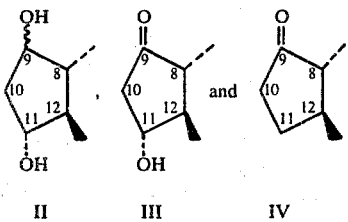

respectively. The dotted lines in the foregoing formulae and in other formulae throughout this specification denote, in accordance with generally accepted rules of nomenclature, that the attached grouping lies behind the general plane of the ring system, i.e. that the grouping is in a α-configuration, the thickened lines ▮ denote that the grouping lies in front of the general plane of the system, i.e. that the grouping is in β-configuration, and the wavy line ∿ indicates that the grouping is in α- or β-configuration.

Such compounds are sub-classified according to the position of double bond(s) in the side chain(s) attached to the 8- and 12-positions of the alicyclic ring. Thus $PG_1$ compounds have a trans-double bond between $C_{13}-C_{14}$(trans-$\Delta^{13}$) and $PG_2$ compounds have a cis-double bond between $C_5-C_6$ and a trans-double bond between $C_{13}-C_{14}$(cis-$\Delta^5$,trans-$\Delta^{13}$). For example, prostaglandin $F_{1\alpha}$ ($PGF_{1\alpha}$) and prostaglandin $E_1$ ($PGE_1$) are characterized by the following structures V and VI.

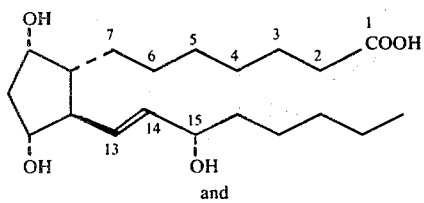

and

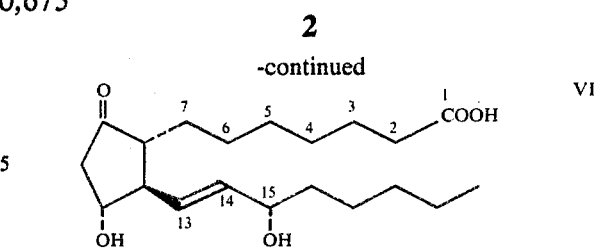

respectively. The structures of $PGF_{2\alpha}$ and $PGE_2$, as members of the $PG_2$ group, correspond to those of formulae V and VI respectively with a cis-double bond between the carbon atoms in positions 5 and 6. Compounds in which the double bond between the carbon atoms in positions 13 and 14 of members of the $PG_1$ group is replaced by ethylene are known as dihydro-prostaglandins, e.g. dihydro-prostaglandin-$F_{1\alpha}$ (dihydro-$PGF_{1\alpha}$) and dihydro-prostaglandin-$E_1$ (dihydro-$PGE_1$).

Moreover, when one or more methylene groups are added to, or eliminated from, the aliphatic group attached to the 12-position of the alicyclic ring of the prostaglandins the compounds are known, in accordance with the usual rules of organic nomenclature, as homo-prostaglandins (methylene group added) or nor-prostaglandins (methylene group eliminated), and, when more than one methylene group is added or eliminated, the number is indicated by di-, tri- etc. before the prefix "homo" or "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGEs and PGAs have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. $PGE_1$ inhibits blood platelet aggregation and also removes the thrombus and prevents thrombosis. PGEs and PGFs have a stimulating effect on smooth muscle and increases the intestinal peristalsis; these actions indicate therapeutic utility on post-operative ileus and as purgatives. Furthermore, PGEs and PGFs may be used as oxytocics, as abortifacients in the first and second trimesters; in the post-labour abortion of the placenta, and as oral contraceptives because they regulate the sexual cycle of female mammals. PGEs and PGAs have vasodilator and diuretic activities. PGEs are useful for improvement in patients suffering from cerebral vascular disease because they increase the cerebral blood flow, and are also useful in the treatment of asthmatic conditions in patients because of their bronchodilating activity.

During the past decade widespread investigations have been carried out in order to discover inter alia new products possessing the pharmacological properties of the 'natural' prostaglandins or one or more of such properties to an enhanced degree. It has now been found that by replacing the pentyl group at the end of the aliphatic group linked to the 12-position of the alicyclic ring of prostaglandins by a substituted cyclopentyl or cyclohexyl group and certain analogues thereof, the pharmacological properties of the 'natural' prostaglandins are, in some aspects of their activities, improved or modified.

The present invention accordingly provides the new prostaglandin analogues of the general formula:

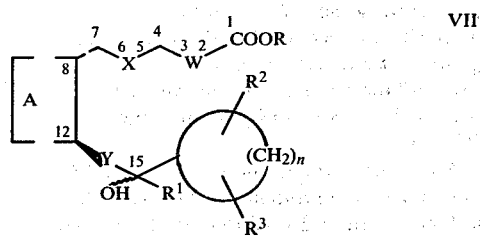

(wherein A represents a grouping of formula IV as indicated hereinbefore or a grouping of the formula:

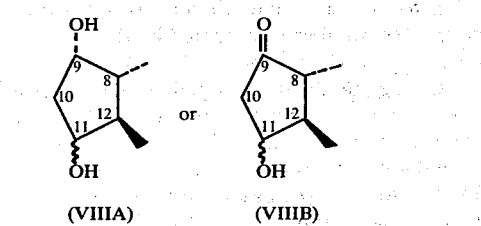

W represents ethylene (i.e. —CH$_2$CH$_2$—) or trans-vinylene (i.e. —CH=CH), X represents ethylene or cis-vinylene, Y represents ethylene or trans-vinylene, R represents a hydrogen atom or a straight- or branched-chain alkyl group containing from 1 to 12 carbon atoms, R$^1$ represents a hydrogen atom or a methyl or ethyl group, R$^2$ represents a straight- or branched-chain alkyl group containing from 2 to 8 carbon atoms or a phenyl group unsubstituted or substituted by an alkyl group containing from 1 to 3 carbon atoms, R$^3$ represents a hydrogen atom or a straight- or branched-chain alkyl group containing from 1 to 3 carbon atoms, and n represents 4 or 5) and cyclodextrin clathrates of such acids and esters and, when R represents a hydrogen atom, non-toxic (e.g. sodium) salts thereof. Preferably R represents a hydrogen atom or a methyl group, preferably R$^1$ represents a hydrogen atom, preferably R$^2$ represents an alkyl group of 2 or 3 carbon atoms, or a phenyl group, preferably R$^3$ represents a hydrogen atom or a methyl group, preferably A represents a grouping of formula VIIIA or VIIIB, and preferably the hydroxy groups depicted in formulae VII, VIIA and VIIIB in α- or β-configuration are attached to the carbon atom in α-configuration.

It is to be understood that the structure

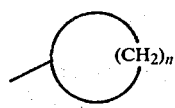

in general formula VII and subsequent formulae appearing in this specification represents a cyclopentyl or cyclohexyl group.

The present invention is concerned with all compounds of general formula VII in the 'natural' form or its enantiomeric form, or mixtures thereof, more particularly the racemic form, consisting of equimolecular mixtures of natural and its enantiomeric form.

As will be apparent to those skilled in the art, the compounds depicted in general formula VII have at least three centres of chirality, these three centres of chirality being at the alicyclic ring carbon atoms of group A identified as 8 and 12 and at the C-15 carbon atom which has attached to it a hydroxy group. Still further centres of chirality occur when the alicyclic group A carries a hydroxy group on the carbon atom in position 11 (i.e. when the ring is that of formula VIIIB) or hydroxy groups in positions 9 and 11 (i.e. when the ring is that of formula VIIIA), and other centres of chirality may occur when R$^2$ is a branched-chain alkyl group. The presence of chirality leads, as is well known, to the existence of isomerism. However, the compounds of general formula VII all have such a configuration that the side-chains attached to the ring carbon atoms in the positions identified as 8 and 12 are trans with respect to each other. Accordingly, all isomers of general formula VII, and mixtures thereof, which have those side-chains attached to the ring carbon atoms in positions 8 and 12 in the trans-configuration and have a hydroxy group as depicted in the 15-position are to be considered within the scope of general formula VII.

According to a feature of the present invention, the prostaglandin analogues of general formula VII, wherein A represents a grouping of formula VIIIA, W represents a ethylene, R represents a hydrogen atom or an alkyl group containing from 1 to 4 carbon atoms, and the other symbols are as hereinbefore defined, i.e. compounds of the general formula:

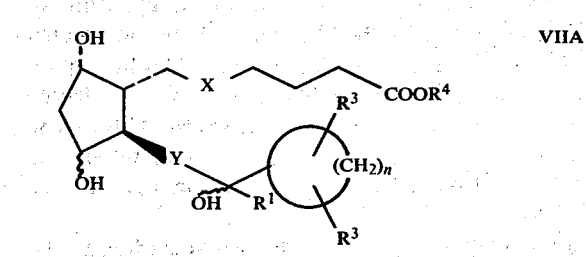

(wherein X, Y, R$^1$, R$^2$, R$^3$ and n are as hereinbefore defined, and R$^4$ represents a hydrogen atom or a straight- or branched-chain alkyl group containing from 1 to 4 carbon atoms, preferably methyl), are prepared by the process which comprises hydrolysing to a hydroxy group the group OR$^5$ of a compound of the general formula:

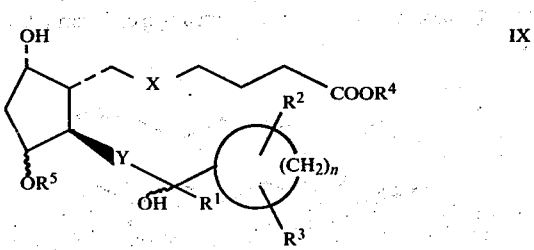

wherein $R^5$ represents a 2-tetrahydropyranyl group unsubstituted or substituted by at least one alkyl group, or a 2-tetrahydrofuranyl or 1-ethoxyethyl group (preferably 2-tetrahydropyranyl), and the other symbols are as hereinbefore defined.

The $OR^5$ group of the compounds of general formula IX may be converted to a hydroxy group by mild hydrolysis with an aqueous solution of an organic acid, e.g. acetic acid, or with a dilute aqueous inorganic acid, e.g. hydrochloric acid, advantageously in the presence of an organic solvent miscible with water, e.g. tetrahydrofuran or an alkanol containing from 1 to 4 carbon atoms, e.g. methanol. The mild hydrolysis may be carried out at a temperature ranging from ambient to 60° C. (preferably at a temperature below 45° C.) with an acid mixture, e.g. a mixture of hydrochloric acid with tetrahydrofuran or methanol, or a mixture of acetic acid, water and tetrahydrofuran. The products of formula VIIA may be purified by column chromatography on silica gel.

Compounds of general formula IX, wherein the various symbols are as hereinbefore defined, may be prepared by the hydrolysis under alkaline conditions of a compound of the general formula:

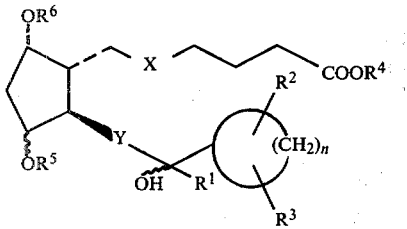

X wherein $R^6$ represents an alkylcarbonyl group containing from 2 to 5 carbon atoms, and the other symbols are as hereinbefore defined. The hydrolysis under alkaline conditions may be effected with (1) an aqueous solution of an alkali metal, e.g. sodium or potassium, hydroxide or carbonate in the presence of a water miscible solvent, e.g. tetrahydrofuran or an alkanol containing from 1 to 4 carbon atoms, to give a compound of general formula IX wherein $R^4$ represents a hydrogen atom, or (2) with anhydrous potassium carbonate in an anhydrous alkanol containing from 1 to 4 carbon atoms, preferably absolute methanol, to give a compound of general formula IX wherein $R^4$ represents an alkyl group containing from 1 to 4 carbon atoms.

Compounds of general formula X wherein $R^1$ represents a hydrogen atom and the other symbols are as hereinbefore defined, i.e. compounds of the general formula:

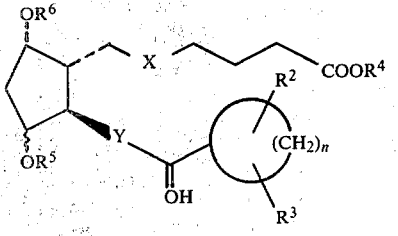

XA (wherein the various symbols are as hereinbefore defined) may be prepared from a compound of the general formula:-

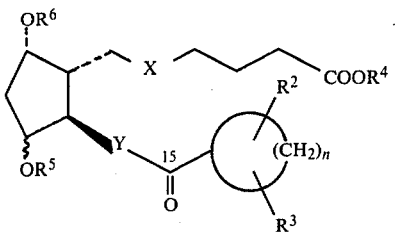

XI (wherein the various symbols are as hereinbefore defined) by reduction to convert the 15-oxo group to a hydroxy group. The reduction is suitably effected with excess sodium borohydride in an alkanol containing from 1 to $\alpha$ carbon atoms, e.g. methanol, at a low temperature, preferably $-30°$ to $-60°$ C., or with zinc borohydride in a suitable inert organic solvent, e.g. 1,2-dimethoxyethane, at a temperature of $-10°$ to $10°$ C. The product thus obtained is a mixture of isomers in which the hydroxy group at position 15 is in $\alpha$- or $\beta$-configuration respectively. If desired, the isomer having the hydroxy group in $\alpha$-configuration may be separated from the isomer having the hydroxy group in $\beta$-configuration by column chromatography of the mixture on silica gel. The separated isomers may be utilized in the procedures herein described to give prostaglandin analogues of general formula VII in which the hydroxy group in position 15 is in $\alpha$- or $\beta$-configuration.

Compounds of general formula X wherein $R^1$ represents a methyl or ethyl group and the other symbols are as hereinbefore defined, i.e. compounds of the general formula:

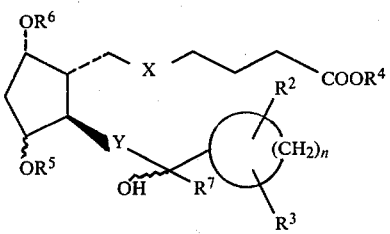

XB (wherein $R^7$ represents a methyl or ethyl group, and the other symbols are as hereinbefore defined), may be prepared from a compound of general formula XI, wherein the various symbols are as hereinbefore defined, by treatment with a Grignard reagent of the general formula:

$R^7$-Mg-Hal     XII (wherein $R^7$ is as hereinbefore defined, and Hal represents a halogen atom), e.g. methylmagnesium iodide, in an inert organic solvent, for example tetrahydrofuran or diethyl ether, at a moderately low temperature, for example at 0° C., followed by hydrolysis of the resulting organomagnesium prostaglandin compound, for example by treatment with water or an aqueous solution of ammonium chloride or an acid, e.g. hydrochloric acid or oxalic acid, to give a mixture of the $\alpha$- and $\beta$-hydroxy epimers of compounds of general formula XB.

The method hereinbefore described for the preparation of prostaglandin analogues of general formula VIIA may be represented by the series of reactions depicted schematically in Scheme A, wherein the various symbols are as hereinbefore defined.

SCHEME A

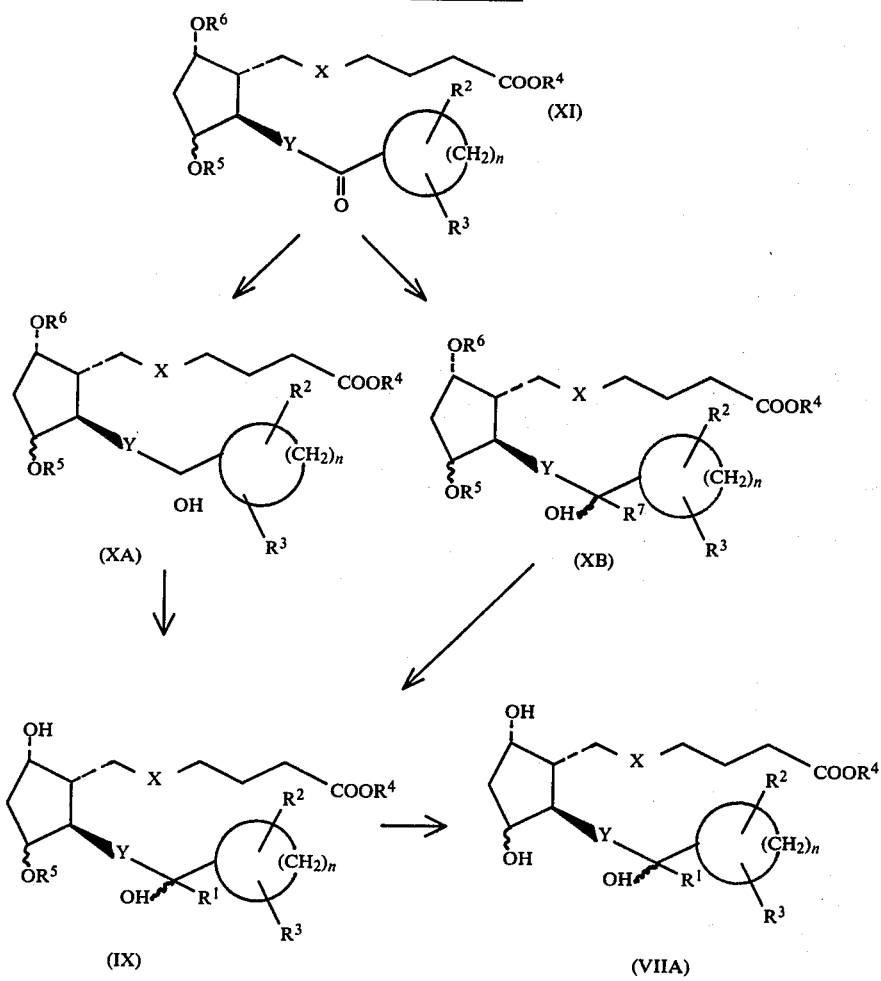

Compounds of general formula XI, wherein Y represents trans-vinylene and the other symbols are as hereinbefore defined, may be obtained by the Wittig reaction of a compound of the general formula:

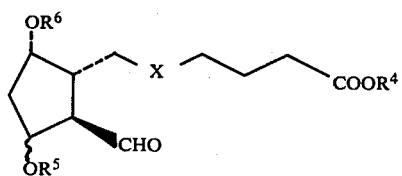

XIII (wherein the various symbols are as hereinbefore defined) with the sodio derivative of a dialkyl phosphonate of the general formula:

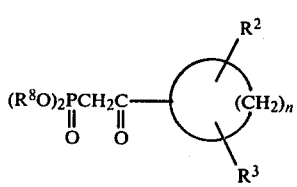

XIV wherein $R^8$ represents an alkyl group containing from 1 to 4 carbon atoms, and the other symbols are as hereinbefore defined. The reaction is preferably effected by suspending sodium hydride in an inert organic solvent, e.g. tetrahydrofuran or 1,2-dimethoxyethane, and adding the dialkyl phosphonate of formula XIV. The resulting sodio derivative of the dialkyl phosphonate may be reacted with the compound of formula XIII at 20° C. to 45° C. for one to five hours to form the trans-enone compound of formula XI stereoselectively.

The compounds of general formula XIII, wherein the various symbols are as hereinbefore defined and the group $OR^5$ is in α-configuration [hereinafter depicted in general formula XIIIA], used as starting materials in the hereinbefore described procedure, may themselves be prepared by methods known per se from compounds of general formula XV by the series of reactions depicted schematically below in Scheme B.

SCHEME B

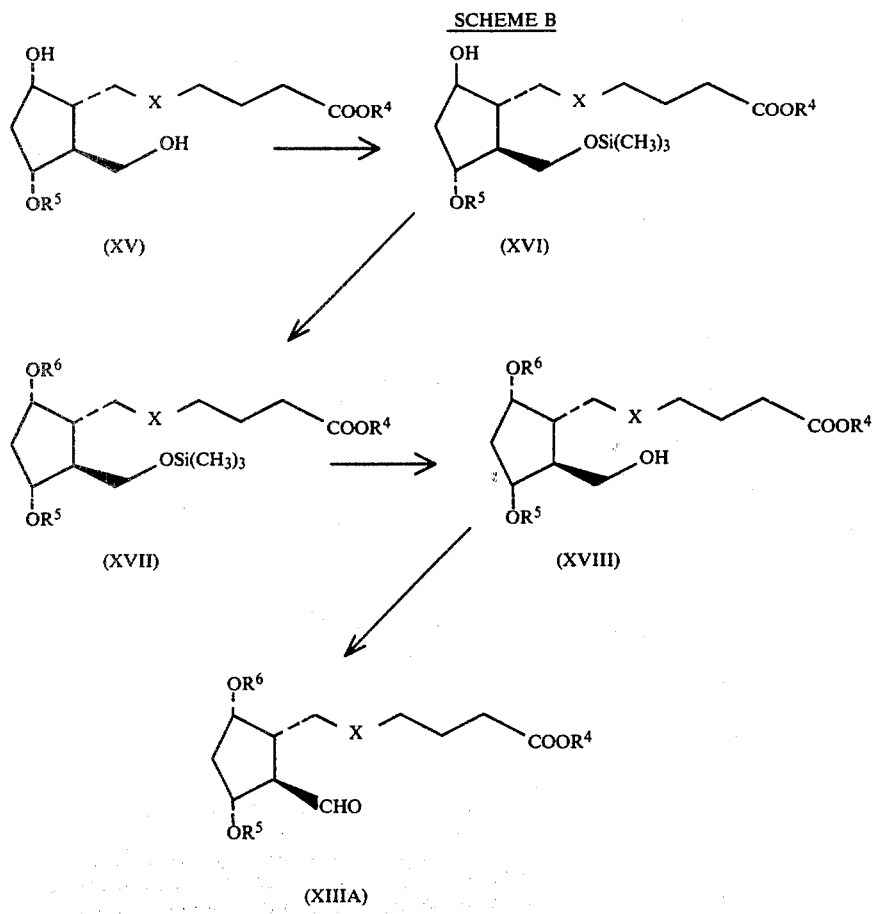

wherein X, $R^4$, $R^5$ and $R^6$ are as hereinbefore defined, and preferably $R^6$ represents an acetyl group.

Compounds of formula XVI may be prepared by reacting a compound of formula XV with trimethylchlorosilane in an inert organic solvent, for example methylenechloride, in the presence of a base, for example pyridine or a tertiary amine, at a low temperature, e.g. at a temperature of −30° C. to 0° C. Compounds of formula XVII may be prepared by reacting a trimethylsilyl ether of formula XVI with the appropriate acyl chloride or acid anhydride in an inert organic solvent, for example methylene chloride, in the presence of a base, for example pyridine or a tertiary amine, at a low temperature, e.g. at a temperature of 0° C. to 30° C. Compounds of formula XVIII may be prepared by treating a compound of formula XVII by methods known per se for the removal of the trimethylsilyl group, for example by treatment with an acid; it is preferably not to use a strong acid in order to avoid the risk of the removal of the group $R^5$. The compounds of formula XVIII may be converted to compounds of formula XIIIA under mild and neutral conditions, e.g. with chromium trioxide-pyridine complex or Jones' reagent and at a moderately low temperature.

The compounds of general formula XV may themselves be prepared by the method described in Japanese Patent Publication No. 49-102646 from the known compounds of formula XIX below [the racemic form of the compound of formula XIX is described in J. Amer. Chem. Soc. 91, 5675 (1969) and the natural configuration compound of formula XIX is described in J. Amer. Chem. Soc. 92, 397 (1970)] which may be represented by the series of reactions depicted schematically below in Scheme C.

SCHEME C

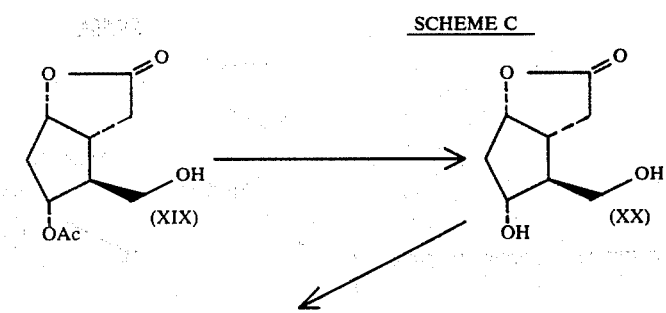

SCHEME C

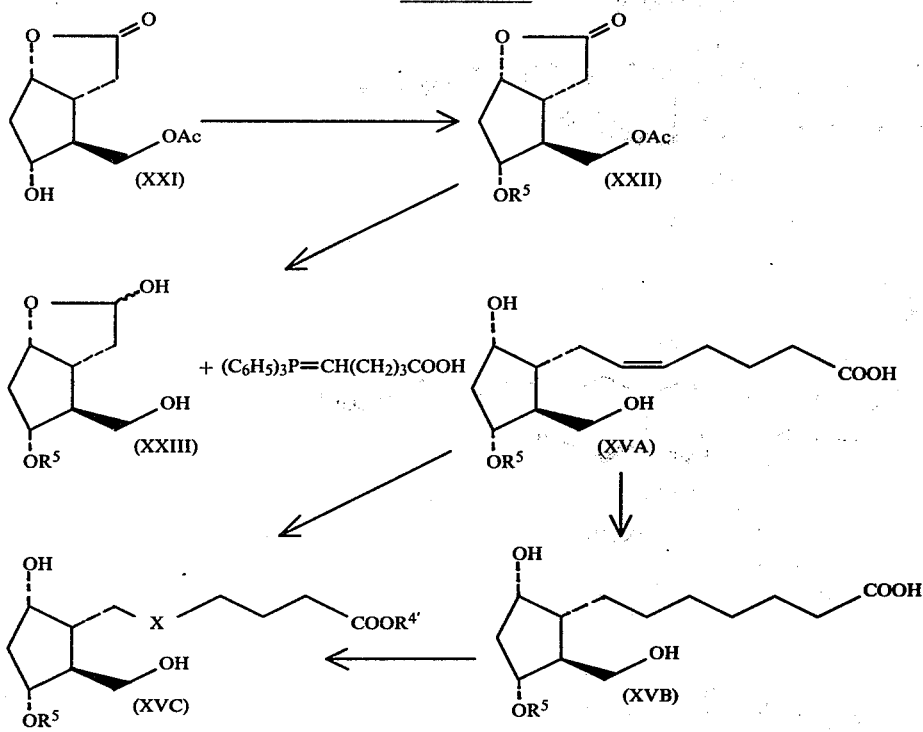

wherein Ac represents the acetyl group (—COCH₃), R⁴' represents a straight- or branched-chain alkyl group containing from 1 to 4 carbon atoms and R⁵ is as hereinbefore defined.

Compounds of formula XX may be prepared by hydrolysis under alkaline conditions of compounds of formula XIX. Compounds of formula XXI may be obtained by the acetylation of compounds of formula XX under mild conditions and may be converted into compounds of formula XXII by reaction with a dihydropyran, dihydrofuran or ethyl vinyl ether in an inert solvent, e.g. methylene chloride, in the presence of a condensing agent, e.g. p-toluenesulphonic acid. Compounds of formula XXIII may be prepared by reducing compounds of formula XXII with diisobutylaluminium hydride in toluene for about 15 minutes at −60° C. Dimsyl anion, previously prepared from sodium hydride and dimethyl sulphoxide, is reacted with (4-carboxybutyl)triphenylphosphonium bromide to form (4-carboxybutylidene)triphenylphosphorane. To that compound is added a compound of formula XXIII and the mixture in dimethyl sulphoxide is made to react for 2 hours at room temperature to yield a compound of formula XVA.

Compounds of formula XVA may, if desired, be reduced to give compounds of formula XVB. Suitably, the reduction may be effected by hydrogenation in the presence of a hydrogenation catalyst, for example palladium on charcoal, palladium black or platinum dioxide, in the presence of an inert organic solvent, for example a lower alkanol, e.g. methanol or ethanol, at laboratory temperature at normal or elevated pressure, e.g. at a hydrogen pressure from atmospheric to 15 kilogrammes per square centimetre. Compounds of formulae XVA or XVB are then reacted with a diazoalkane in a suitable inert solvent (e.g. diethyl ether) to give, when required, esters of formula XVC.

The compounds of general formula XIII wherein X represents ethylene or cis-vinylene, R⁴, R⁵ and R⁶ are as hereinbefore defined and the group OR⁵ is in β-configuration, which may be used as starting materials in the hereinbefore described procedures, may themselves be prepared by the series of reactions depicted in Schemes B and C but replacing the compounds of formula XIX by compounds of the formula:

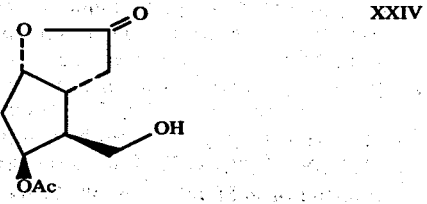

XXIV wherein Ac is as hereinbefore defined.

A method for the preparation of the bicyclooctane starting materials of formula XXIV, wherein Ac is as hereinbefore defined, utilizing known procedures may be represented by the series of reactions depicted schematically below in Scheme D (cf. E.J. Corey and Shiro Terashima, Tetrahedron Letters, No. 2, pp. 111–113, 1972).

SCHEME D

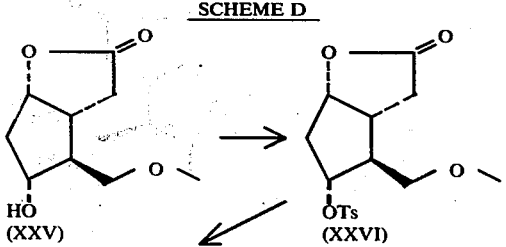

-continued

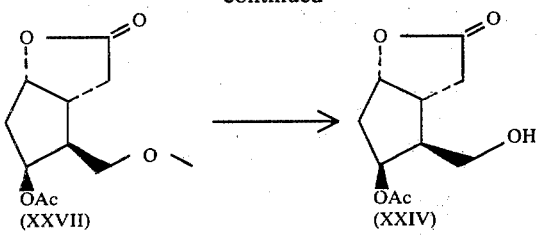

wherein Ac is as hereinbefore defined and Ts represents the tosyl group. The various reactions depicted above in Scheme D may be effected by methods known per se. Compounds of formula XXVII may be prepared by reacting compounds of formula XXVI with tetraethylammonium acetate.

The dialkyl phosphonate starting materials of general formula XIV, wherein the various symbols are as hereinbefore defined, may be prepared by reacting a solution of n-butyllithium in diethyl ether with a solution of a dialkyl methylphosphonate of the formula:

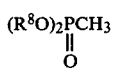
XXVIII (wherein $R^8$ is as hereinbefore defined), e.g. dimethyl methylphosphonate or diethyl methylphosphonate, at a temperature below $-50°$ C., and then adding dropwise to the reaction mixture a solution of a compound of the general formula:

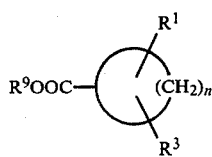
XXIX (wherein $R^9$ represents an alkyl group containing from 1 to 4 carbon atoms, and the other symbols are as hereinbefore defined) in tetrahydrofuran at a temperature below $-50°$ C., stirring the reaction mixture at below $-50°$ C., and then stirring at a moderately low temperature, e.g. at $0°$ C., to give the desired dialkyl phosphonate of general formula XIV.

The prostaglandin analogues of general formula VII wherein A represents a grouping of formula VIIIA or VIIIB, W represents ethylene, R represents a hydrogen atom or a straight- or branched-chain alkyl group containing from 1 to 4 carbon atoms, X represents ethylene or cis-vinylene and Y represents trans-vinylene or X and Y each represent ethylene, and the other symbols are as hereinbefore defined, i.e. compounds of the general formula:

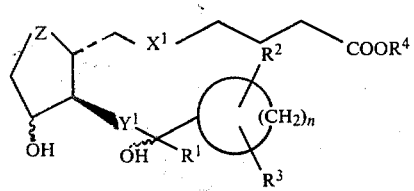
VIIB (wherein Z represents

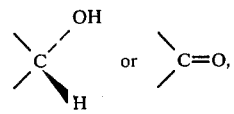

$X^1$ represents ethylene or cis-vinylene and $Y^1$ represents trans-vinylene or $X^1$ and $Y^1$ each represent ethylene, and the other symbols are as hereinbefore defined), are prepared by the process which comprises hydrolysing to hydroxy groups the $OR^5$ groups of a compound of the general formula:

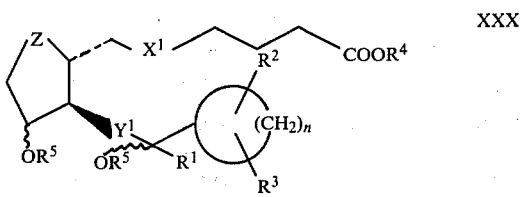
XXX (wherein the various symbols are as hereinbefore defined) by means hereinbefore described for the conversion of compounds of the general formula IX into compounds of general formula VIIA.

If desired, acids of general formula VIIB, wherein $R^4$ represents a hydrogen atom, Z represents $>C=O$ and the other symbols are as hereinbefore defined, may be prepared by treatment of corresponding esters of that formula, viz. compounds wherein $R^4$ represents an alkyl group containing from 1 to 4 carbon atoms, with bakers' yeast [cf. C. J. Sih et al, J. Amer. Chem. Soc. 94, 3643–3644 (1972)].

Compounds of general formula XXX wherein Z represents $>C=O$ and the other symbols are as hereinbefore defined, i.e. compounds of the general formula XXXA hereinafter depicted, may be prepared from compounds of general formula XXX wherein Z represents

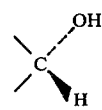

by methods known per se for the conversion of a hydroxy group in the 9-position of a prostaglandin compound to an oxo radical, for example by means of Collins' reagent (chromium trioxidepyridine complex) at about $0°$ C., or a chromic acid solution (e.g. obtained from chromium trioxide, manganese sulphate, sulphuric acid and water) or Jones' reagent.

Compounds of general formula XXX wherein Z represents

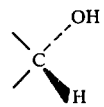

and $X^1$ represents ethylene, $Y^1$ represents trans-vinylene or ethylene, and the other symbols are as hereinbefore defined, i.e. compounds of general formula XXXB hereinafter depicted, may be prepared from a compound of the general formula:

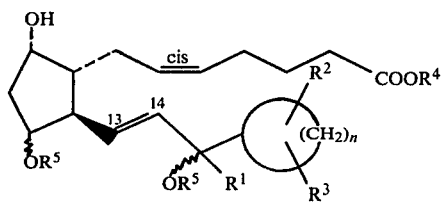

XXXI (wherein the various symbols are as hereinbefore defined) by hydrogenation in the presence of a hydrogenation catalyst, for example palladium black or palladium on charcoal, in the presence of an inert solvent, for example, a lower alkanol, e.g. methanol or ethanol, at laboratory temperature and at normal pressure or elevated pressure, e.g. at a hydrogen pressure from atmospheric to 15 kilogrammes per square centimeter, the hydrogenation being monitored to avoid, if desired, any reduction of the $C_{13}$–$C_{14}$ trans double bond.

Compounds of general formula XXXI, wherein the various symbols are as hereinbefore defined, and related compounds of the general formula:

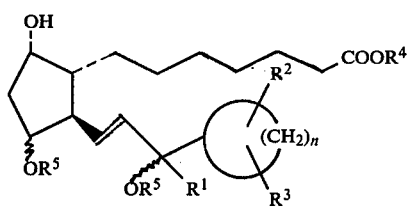

XXXII (wherein the various symbols are as hereinbefore defined) may be prepared from a compound of the general formula:

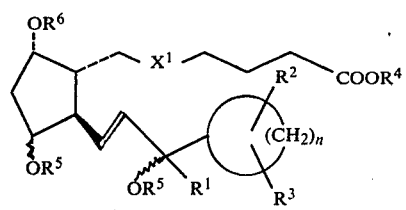

XXXIII (wherein the various symbols are as hereinbefore defined) by the application of the procedures hereinbefore described for the conversion of compounds of general formula X into compounds of general formula IX.

Compounds of general formula XXXIII, wherein the various symbols are as hereinbefore defined, may be prepared from a compound of general formula X wherein the various symbols are as hereinbefore defined, by reaction with a dihydropyran, dihydrofuran or ethyl vinyl ether in an inert organic solvent, e.g. methylene chloride, in the presence of a condensing agent, e.g. p-toluenesulphonic acid.

The method hereinbefore described for the preparation of prostaglandin analogues of general formula VIIB may be represented by the series of reactions depicted schematically below in Scheme E, wherein the various symbols are as hereinbefore defined.

SCHEME E

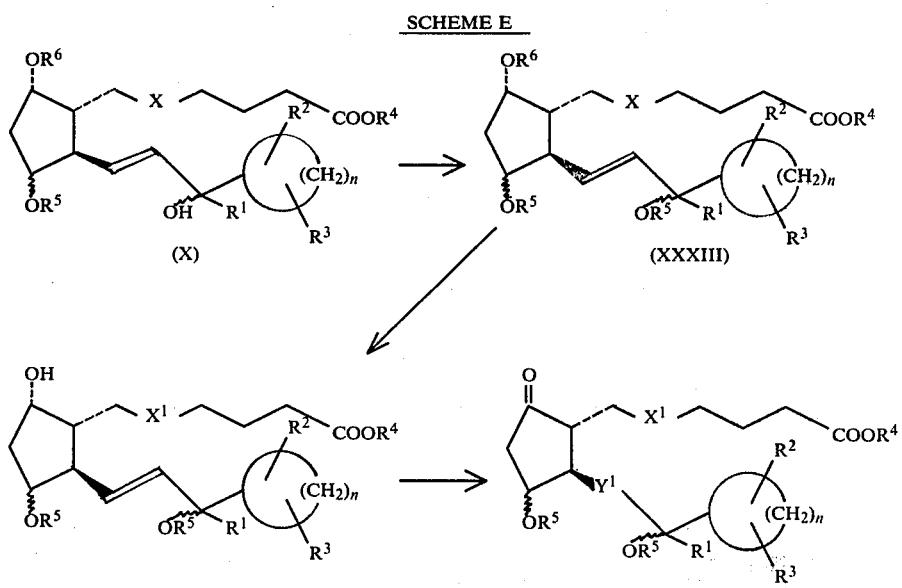

SCHEME E

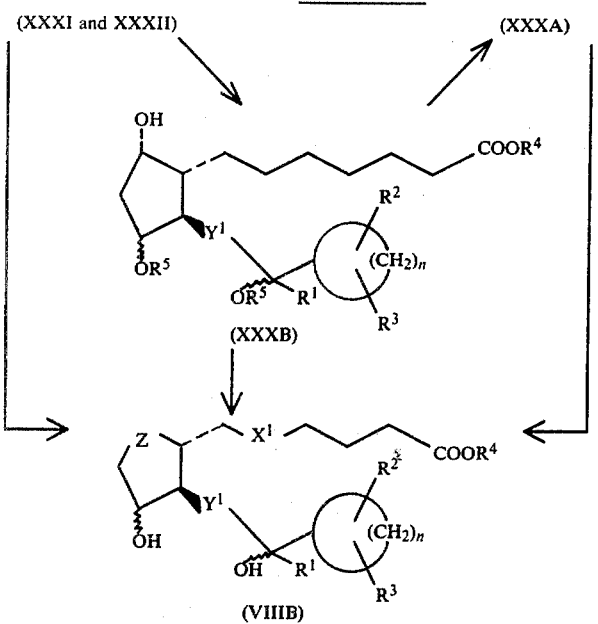

The prostaglandin analogues of general formula VII wherein A represents a grouping of formula VIIIA or VIIIB, W represents ethylene, R represents a hydrogen atom or a straight- or branched-chain alkyl group containing from 1 to 4 carbon atoms, X represents cis-vinylene, Y represents ethylene and the other symbols are as hereinbefore defined, i.e. compounds of the general formula:

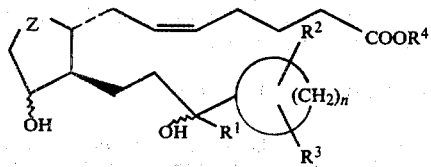

VIIC (wherein the various symbols are as hereinbefore defined), are prepared by the process which comprises hydrolysing to hydroxy groups the $OR^5$ groups of a compound of the general formula:

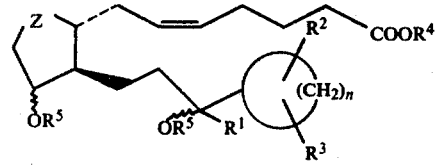

XXXIV (wherein the various symbols are as hereinbefore defined) by means hereinbefore described for the conversion of compounds of general formula IX into compounds of general formula VIIA.

The starting materials of general formula XXXIV may be prepared by the series of reactions depicted below in Scheme F, wherein the various symbols are as hereinbefore defined.

SCHEME F

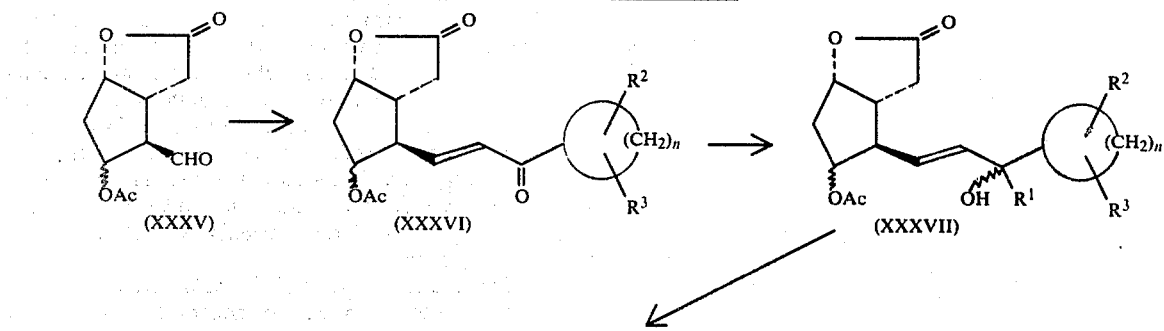

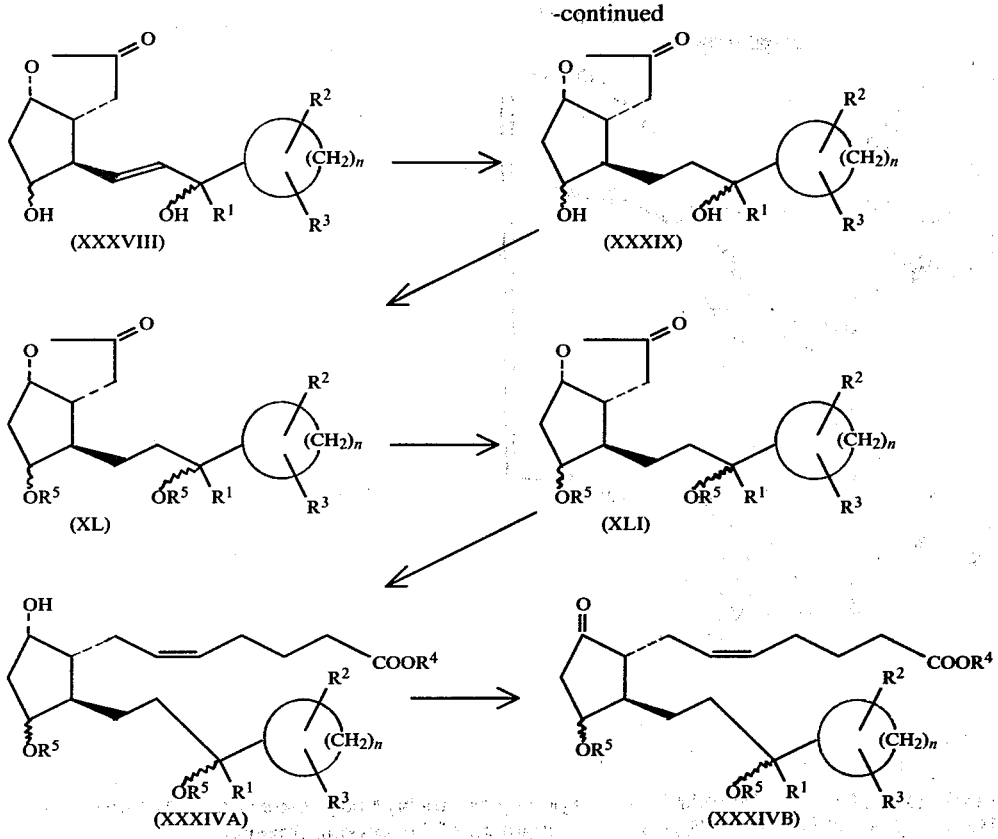

The starting compound of formula XXXV wherein the acetoxy group is in α-configuration may be prepared according to the method described in J. Amer. Chem. Soc., 91, 5675 (1969) and J. Amer. Chem. Soc., 92, 397 (1970), and the starting compound of formula XXXV wherein the acetoxy group is in β-configuration may be prepared by oxidation under mild and neutral conditions, e.g. with Collins' reagent or Jones' reagent and at a moderately low temperature, of a compound of formula XXIV.

The compounds of formula XXXV may be converted to compounds of general formula XXXVI by the application of the procedures hereinbefore described for the conversion of compounds of general formula XIII into compounds of the general formula XI.

Compounds of general formula XXXVI may be converted to compounds of general formula XXXVII by the application of the procedures hereinbefore described for the conversion of compounds of general formula XI into compounds of the general formula X.

Compounds of general formula XXXVII may be converted to compounds of general formula XXXVIII by reaction with anhydrous potassium carbonate in methanol.

Compounds of general formula XXXVIII may be converted to compounds of general formula XXXIX by the application of the procedures hereinbefore described for the conversion of compounds of general formula XXXI into compounds of general formula XXXB.

Compounds of general formula XXXIX may be converted to compounds of general formula XL by the application of the procedures hereinbefore described for the conversion of compounds of general formula X into compounds of general formula XXXIII.

Compounds of general formula XL may be converted to compounds of general formula XLI by reduction with diisobutylaluminium hydride in an inert solvent, e.g. toluene, n-pentane or n-hexane, at a low temperature, e.g. −78° to −20° C.

Compounds of general formula XLI may be converted to compounds of general formula XXXIVA wherein $R^4$ represents a hydrogen atom, by reaction with a compound of the formula:

$$(C_6H_5)_3\overset{\oplus}{P}CH_2CH_2CH_2CH_2COOHBr^{\ominus} \qquad \text{XLII}$$

in the presence of a strong base, for example sodium methylsulphinylmethylide, under the normal conditions utilized for effecting the Wittig reaction, e.g. in an inert solvent at ambient temperature. The reaction is preferably carried out in dimethyl sulphoxide because the compound of formula XLII is practically insoluble in other solvents, e.g. tetrahydrofuran, and because a cis-double bond must be formed stereospecifically in the Wittig reaction. For the better performance of the Wittig reaction, more than three equivalents of the phosphorane compound, prepared from the compound of the formula XLII, viz. (4-carboxybutylidene)triphenylphosphorane, are required. Reaction between the compound of the formula XLI and the phosphorane is usually completed in about one to five hours at laboratory temperature.

Compounds of general formula XXXIVA, wherein $R^4$ represents a straight- or branched-chain alkyl group containing from 1 to 4 carbon atoms, may be prepared by the esterification with a diazoalkane of the corresponding acids of that formula, viz. $R^4$ represents a hyrogen atom.

Compounds of general formula XXXIVA may be converted to compounds of general formula XXXIVB by the application of the procedures hereinbefore described for the conversion of compounds of general formula XXXB, into compounds of general formula XXXA.

It will be appreciated that the prostaglandin analogues of general formulae VIIB and VIIC can be combined into a single general formula, thus:

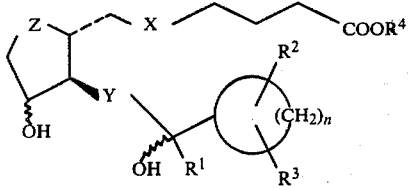    VIID (wherein the various symbols are as hereinbefore defined), and the starting materials for the preparation of such products of general formulae XXX and XXXIV are covered by the single general formula:

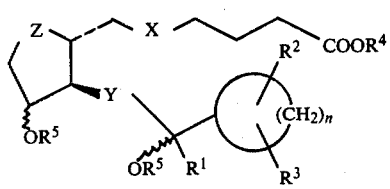    XLIII wherein the various symbols are as hereinbefore defined.

Compounds of general formula XLIII, wherein Z represents >C=O and the other symbols are as hereinbefore defined, i.e. compounds of the general formula:

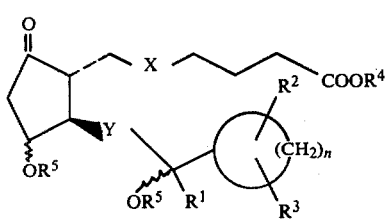    XLIIIA (wherein the various symbols are as hereinbefore defined) may be prepared from compounds of general formula XLIII, wherein Z represents

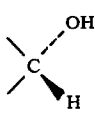

and the other symbols are as hereinbefore defined, i.e. compounds of the general formula:

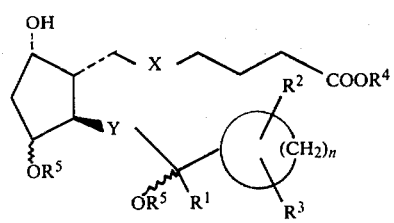    XLIIIB (wherein the various symbols are as hereinbefore defined) by methods known per se, for example by means of Collins' reagent or a chromic acid solution or Jones' reagent.

Compounds of general formula XLIIIB, wherein the various symbols are as hereinbefore defined, may be prepared from a compound of the general formula:

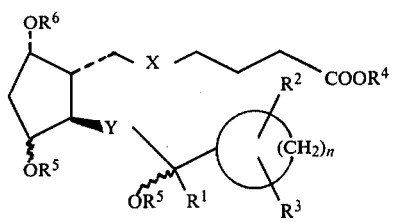    XLIV (wherein the various symbols are as hereinbefore defined) by means heretofore mentioned for the conversion of compounds of general formula X to those of general formula IX.

Compounds of general formula XLIV, wherein the various symbols are as hereinbefore defined, may be prepared from compounds of general formula X by means heretofore mentioned for the conversion of compounds of general formula X to those of general formula XXXIII.

According to another feature of the present invention, the compounds of general formula VII wherein A represents a grouping of formula VIIIB, W and X each represent ethylene, R represents a hydrogen atom or an alkyl group containing from 1 to 4 carbon atoms, and the other symbols are as hereinbefore defined, i.e. compounds of the general formula:

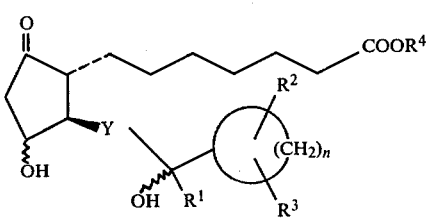    VIIE (wherein the various symbols are as hereinbefore defined, cf. general formula VIID in which Z represents >C=O, X represents ethylene, Y represents ethylene or trans-vinylene, and the other symbols are as hereinbefore defined) are prepared by the process which comprises hydrolyzing a compound of the general formula:

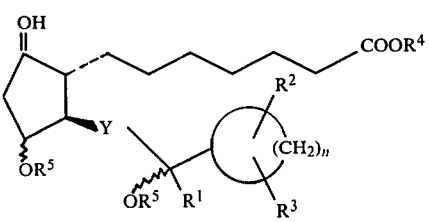    XLV (wherein $R^{10}$ represents a straight- or branched-chain alkyl group containing from 1 to 4 carbon atoms or a 2-tetrahydropyranyl group unsubstituted or substituted by at least one alkyl group, or a 2-tetrahydrofuranyl or 1-ethoxyethyl group, and the other symbols are as hereinbefore defined) by means heretofore mentioned for the conversion of compounds of general formula IX to those of general formula VIIA to convert the OR⁵ groups to hydroxy groups, and the grouping COOR¹⁰ (when it is other than an alkoxycarbonyl group) to a carboxy group.

Compounds of general formula XLV, wherein the various symbols are as hereinbefore defined, may be prepared from a compound of the general formula:

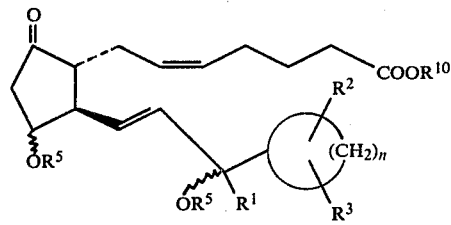

(wherein the various symbols are as hereinbefore defined) by means heretofore mentioned for the conversion of compounds of general formula XXXI to those of general formula XXXB.

Compounds of general formula XLVI, wherein the various symbols are as hereinbefore defined, may be prepared from compounds of general formula VIID, wherein Z represents >C=O, X represents cis-vinylene, Y represents trans-vinylene and the other symbols are as hereinbefore defined, by means heretofore mentioned for the conversion of compounds of general formula X to those of general formula XXXIII.

Compounds of general formula X, wherein the various symbols are as hereinbefore defined, may also be prepared from compounds of general formula XLVII by the series of reactions depicted schematically below in Scheme G, wherein the various symbols are as hereinbefore defined.

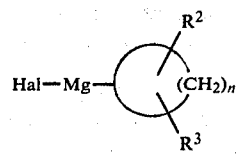

(wherein the various symbols are as hereinbefore defined) in an inert organic solvent, e.g. diethyl ether or tetrahydrofuran, at a moderately low temperature, e.g. at 0° C., followed by hydrolysis of the resulting organomagnesium compound, for example by treatment with water or an aqueous solution of ammonium chloride or an acid, e.g. hydrochloric acid or oxalic acid, to give a mixture of the 15α- and 15β-hydroxy isomers of compounds of general formula XA. If desired, the isomers having the hydroxy group in α- and β-configuration may be separated from the mixture by column chromatography on silica gel.

Compounds of general formula XI, wherein the various symbols are as hereinbefore defined, may be prepared from compounds of general formula XA by methods known per se, for example by means of a chromic acid solution or manganese dioxide.

Compounds of general formula XI may be converted to compounds of general formula XB as hereinbefore described.

Compounds of general formula XLVII, wherein the various symbols are as hereinbefore defined, may be prepared by the sequence of reactions hereinafter depicted schematically in Scheme H, wherein the various symbols are as hereinbefore defined.

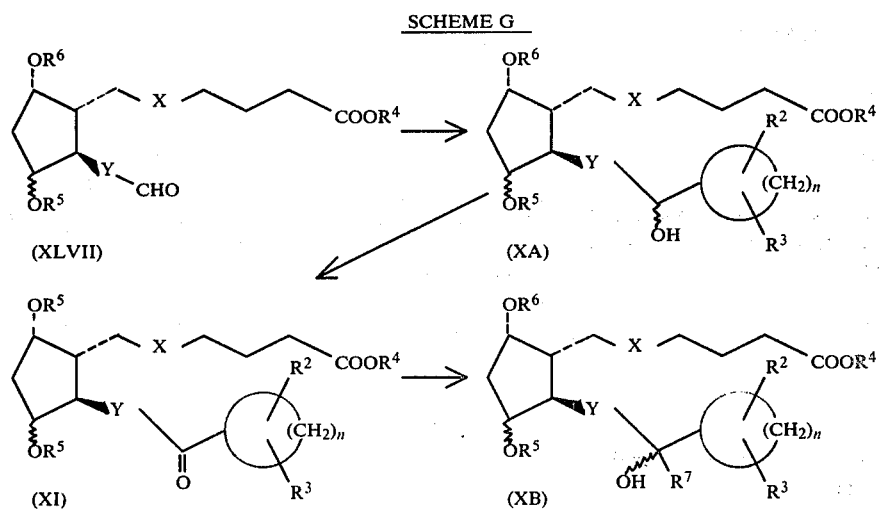

Compounds of general formula XA, wherein the various symbols are as hereinbefore defined, may be prepared from compounds of general formula XLVII by treatment with a Grignard reagent of the general formula:

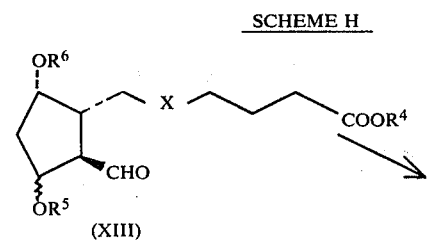

-continued
SCHEME H

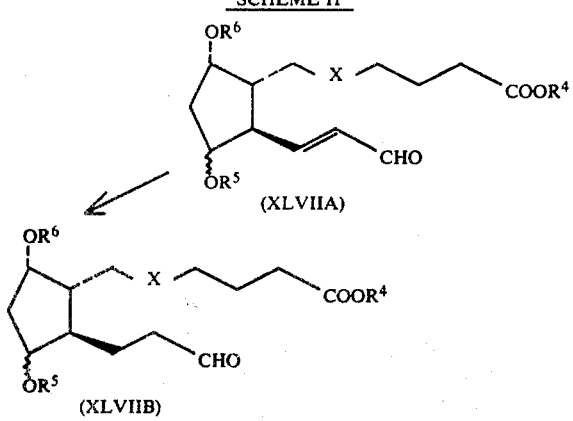

Compounds of general formula XIII may be converted to compounds of general formula XLVIIA by reaction with formylmethylenetriphenylphosphorane of the formula $(C_6H_5)_3P=CHCHO$ [described in J. Chem. Soc., 1266 (1961) by S. Tipett and D. M. Walker] in an inert organic solvent, e.g. benzene, N,N-dimethylformamide or dimethyl sulphoxide, at a temperature of 30° to 80° C.

Compounds of general formula XLVIIA may, if desired, be converted to compounds of general formula XLVIIB by the selective reduction of the carbonyl conjugated double bond of the compounds of general formula XLVIIA by known methods, for example by means of lithium 1-pentyne-hydrocuprate of the formula $LiCuH-C\equiv C-n-C_3H_7$ [cf. J. Amer. Chem. Soc. 96, 3686 (1974)].

Compounds of general formula XLVII, wherein X represents cis-vinylene, Y represents trans-vinylene and the other symbols are as hereinbefore defined, may be prepared by the sequence of reactions hereinafter depicted schematically in Scheme I, wherein $R^{11}$ represents an alkyl group containing from 1 to 4 carbon atoms and the other symbols are as hereinbefore defined.

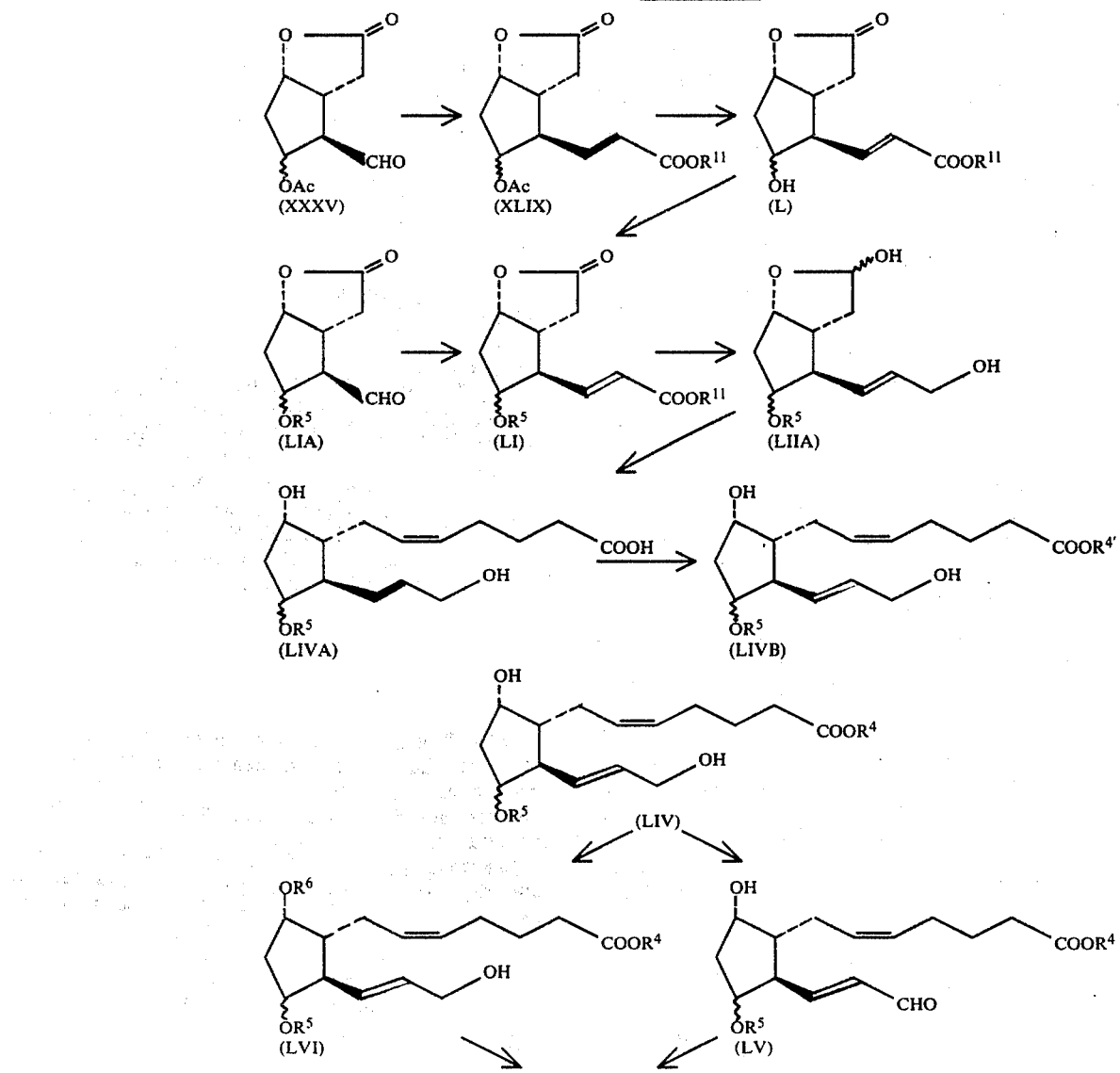

SCHEME I -continued

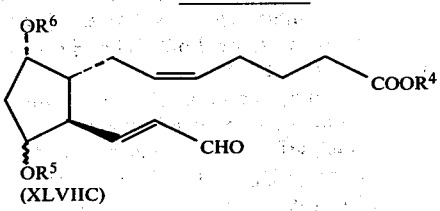

(XLVIIC)

Compounds of formula XXXV may be converted stereoselectively to the trans-$\alpha,\beta$-unsaturated esters of general formula XLIX by reaction with a sodium derivative of the general formula:

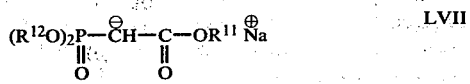
LVII (wherein $R^{12}$ represents an alkyl group containing from 1 to 4 carbon atoms and $R^{11}$ is as hereinbefore defined) in an inert organic solvent, e.g. tetrahydrofuran or 1,2-dimethoxyethane, at a temperature of 0° to 30° C.

Compounds of general formula XLIX may be converted to compounds of general formula L by selective deacetylation with an equimolar amount of anhydrous potassium carbonate in absolute methanol.

The conversion of compounds of general formula L to those of general formula LI may be carried out by means heretofore mentioned for the conversion of compounds of general formula X to those of general formula XXXIII.

Compounds of general formula LI may also be prepared from compounds of general formula LII by means heretofore mentioned for the conversion of compounds of formula XXXV to those of general formula XLIX.

Compounds of general formula LI may be converted to compounds of general formula LIII by reduction with diisobutylaluminium hydride in an inert organic solvent, e.g. toluene, n-pentane or n-hexane, at a low temperature, e.g. at −78° to −20° C.

The conversion of compounds of general formula LIII to those of general formula LIVA may be carried out by means heretofore mentioned for the conversion of compounds of general formula XXIII to those of general formula XVA.

Compounds of general formula LIVB, wherein $R^{4'}$ represents an alkyl group containing from 1 to 4 carbon atoms and $R^5$ is as hereinbefore defined, may, if desired, be prepared from compounds of general formula LIVA by methods known per se, for example by reaction with a diazoalkane compound containing from 1 to 4 carbon atoms.

Compounds of general formula LIV may be converted to compounds of general formula LV by oxidation with manganese dioxide in an inert organic solvent, e.g. acetone, at laboratory temperature, which oxidises an allylic alcohol group selectively to a formyl group.

The conversion of compounds of general formula LV to those of general formula XLVIIC may be carried out by means heretofore mentioned for the conversion of compounds of general formula XVI to those of general formula XVII.

Compounds of general formula LIV may be converted to compounds of general formula LVI by reaction with trimethylchlorosilane in an inert organic solvent, e.g. methylene chloride, in the presence of a base, e.g. pyridine or a tertiary amine, at a low temperature, acylation with an acyl halide or acid anhydride in an inert organic solvent in the presence of a base, e.g. pyridine or a tertiary amine, and treatment of the resulting compound by methods known per se for the removal of the trimethylsilyl group, for example by treatment with an acid. It is preferable not to use a strong acid to avoid the risk of the removal of the group $R^5$.

The conversion of compounds of general formula LVI to those of general formula XLVIIC may be carried out by means heretofore mentioned for the conversion of compounds of general formula LIV to those of general formula LV.

Compounds of general formula LII may be prepared from a compound of the general formula:

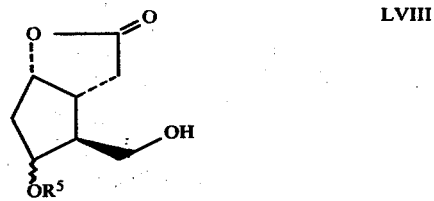
LVIII (wherein $R^5$ is as hereinbefore defined) by means heretofore mentioned for the conversion of compounds of general formula XVIII to those of general formula XIIIA.

Compounds of general formula LVIII wherein the group $OR^5$ is in $\alpha$-configuration may be prepared from a compound of general formula XXII, the compounds of general formula LVIII wherein the group $OR^5$ is in $\beta$-configuration may be prepared from a compound of the general formula:

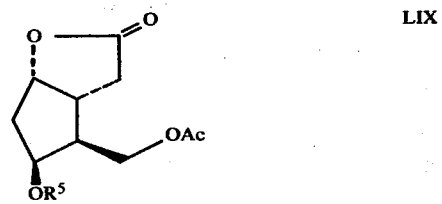
LIX (wherein $R^5$ is as hereinbefore defined) by deacetylation with potassium carbonate in methanol at laboratory temperature.

Compounds of general formula LIX wherein $R^5$ and Ac are as hereinbefore defined may be prepared from compounds of the formula XXIV by the series of reactions depicted schematically below in following Scheme J.

SCHEME J

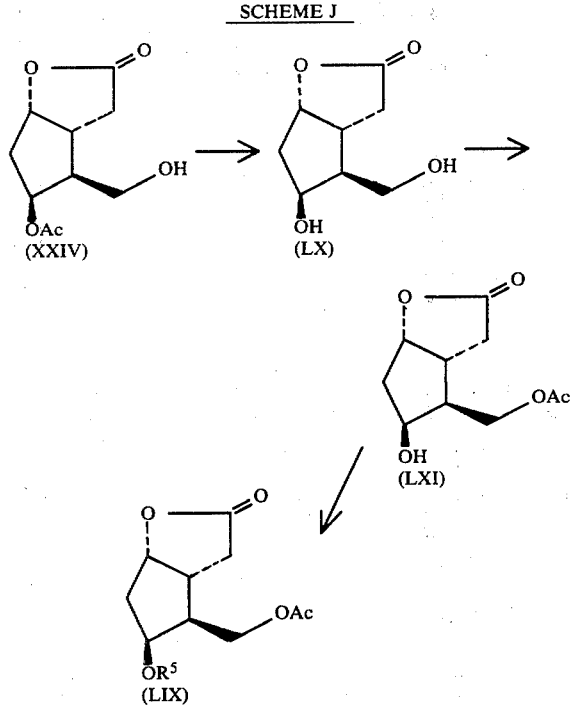

wherein R⁵ and Ac are as hereinbefore defined. The various reactions depicted above in Scheme J may be effected by known methods. Compounds of formula LXI may be prepared by selective acetylation of compounds of formula LX under mild conditions, for example with an equimolecular amount of acetyl chloride at a low temperature, for example −20° to −10° C.

According to a further feature of the present invention, the trans-Δ²-prostaglandin analogues of general formula VII, wherein A represents a grouping of formula VIIIA or VIIIB, W represents trans-vinylene, R represents a hydrogen atom or a straight- or branched-chain alkyl group containing from 1 to 4 carbon atoms and the other symbols are as hereinbefore defined, i.e. compounds of the general formula:

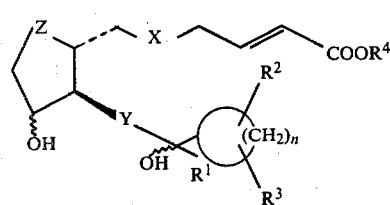

VIIF (wherein the various symbols are as hereinbefore defined, and the depicted double bond is trans) are prepared by the process which comprises hydrolysing to a hydroxy group the group OR⁵, and the group OR¹³ when R¹³ is other than a hydrogen atom, of a compound of the general formula:

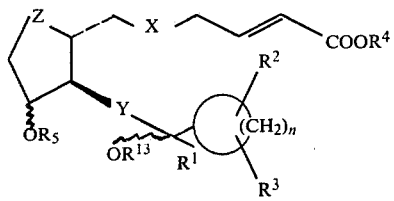

LXII (wherein R¹³ represents a hydrogen atom or a 2-tetrahydropyranyl group unsubstituted or substituted by at least one alkyl group, or a 2-tetrahydrofuranyl or 1-ethoxyethyl group, and the other symbols are as hereinbefore defined) by means heretofore mentioned for the conversion of compounds of general formula IX to those of general formula VIIA.

Compounds of general formula LXII, wherein Z represents >C=O, R¹³ is other than a hydrogen atom and the other symbols are as hereinbefore defined, i.e. compounds of the general formula:

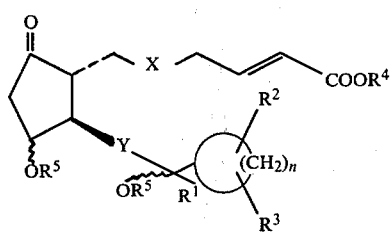

LXIIA (wherein the various symbols are as hereinbefore defined, and the depicted carbon to carbon double bond is trans) may be prepared from compounds of general formula LXII, wherein Z represents

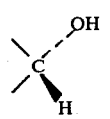

R¹³ is other than a hydrogen atom, and the other symbols are as hereinbefore defined, i.e. compounds of the general formula:

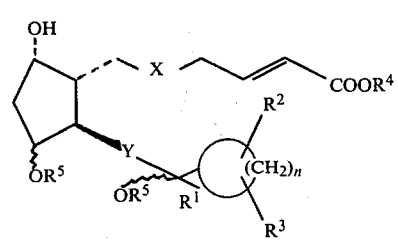

LXIIB (wherein the various symbols are as hereinbefore defined, and the depicted double bond is trans) by means heretofore mentioned for the conversion of compounds of general formula XXXI or XXXII to those of general formula XXXA.

Compounds of general formula LXII, wherein Z represents

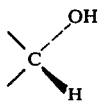

and the other symbols are as hereinbefore defined, i.e. compounds of the general formula:

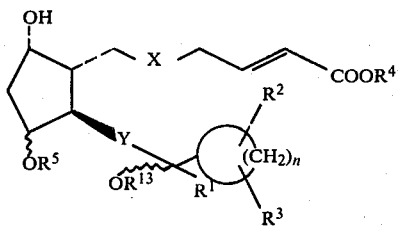

LXIIC (wherein the various symbols are as hereinbefore defined, and the depicted double bond is trans) may be prepared by the process which comprises reacting compounds of general formula IX or XLIIIB, i.e. compounds of the general formula:

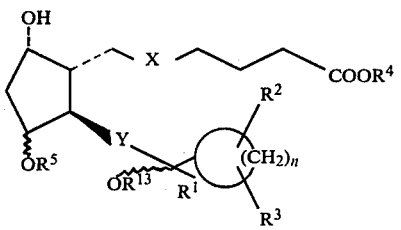

LXIII (wherein the various symbols are as hereinbefore defined) with a lithium compound of the general formula:

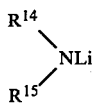

LXIV (wherein $R^{14}$ and $R^{15}$, which may be the same or different, each represent a straight- or branched-chain alkyl group containing from 1 to 6 carbon atoms, or a cycloalkyl group containing from 3 to 6 carbon atoms), e.g. lithium diisopropylamide, to obtain a lithium compound of the general formula:

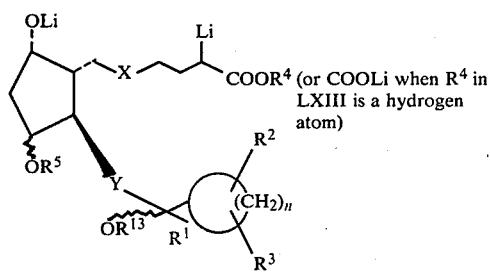

LXV (or OLi when $R^{13}$ in LXIII is a hydrogen atom)

(wherein the various symbols are as hereinbefore defined), reacting the lithium compound with benzeneselenenyl bromide (i.e. $C_6H_5SeBr$), or diphenyldiselenide, or a dialkyldisulphide or diphenyldisulphide of the general formula: $R^{16}SSR^{16}$, wherein $R^{16}$ represents an alkyl group containing from 1 to 4 carbon atoms or a phenyl group, hydrolysing the resulting intermediate to obtain a compound of the general formula:

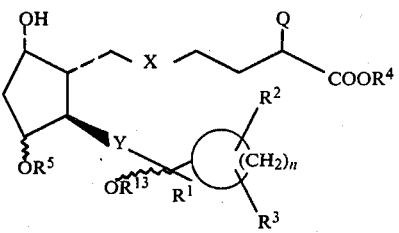

LXVI (wherein Q represents a group $-SeC_6H_5$ or a group $-SR^{16}$, in which $R^{16}$ is as hereinbefore defined, and the other symbols are as hereinbefore defined), treating the resulting compound with hydrogen peroxide or sodium periodate, and decomposing the resulting compound of the general formula:

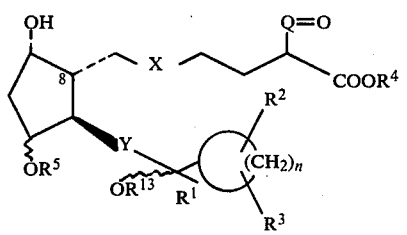

LXVII (wherein the various symbols are as hereinbefore defined) to convert the grouping

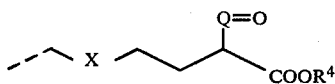

attached to the 8-position of the cyclopentane ring to a trans-$\Delta^2$ grouping

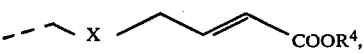

wherein $R^4$ is as hereinbefore defined.

The reaction between compounds of general formula LXIII and lithiated amines of general formula LXIV is carried out in an organic solvent, for example when $R^4$ represents an alkyl group, by adding dropwise a solution of an ester of general formula LXIII in tetrahydrofuran to a solution of an amine of general formula LXIV in tetrahydrofuran at a low temperature, e.g. at −78° C., or, when $R^4$ represents a hydrogen atom, adding dropwise a solution of an acid of general formula LXIII in tetrahydrofuran to a solution of an amine of general formula LXIV in tetrahydrofuran at a low temperature in the presence of hexamethylphosphotriamide at 0° C., the ratio of the molecular equivalents of compounds of general formula LXIII to LXIV in the reaction mixture being suitably adjusted to obtain a lithium compound of general formula LXV. In the case where a prostaglandin ester is employed as reactant, after completion of the addition of the prostaglandin solution to the amine solution, the reaction mixture is stirred at the same temperature for about 30 minutes to obtain a solution of the lithium compound of general formula LXV. In the case where a prostaglandin acid is employed as reactant ($R^4$ represents a hydrogen atom), the reaction mixture is stirred at room temperature for about 30 minutes to obtain a solution of the lithium compound of general formula LXV.

The reaction between the lithium compound of general formula LXV and benzeneselenenyl bromide, diphenyldiselenide or a dialkyl- or diphenyldisulphide, is preferably carried out in tetrahydrofuran, hexamethylphosphotriamide, diethyl ether, n-hexane or n-pentane or a mixture of two or more of them, tetrahydrofuran being the preferred solvent, at a low temperature when $R^4$ in formula LXV represents an alkyl group, e.g. $-78°$ C., or, when $R^4$ in formula LXV represents a hydrogen atom, at $0°$ C. Thus, to the lithium compound solution obtained as described above there is added a solution in tetrahydrofuran of benzeneselenenyl bromide, diphenyldiselenide or a dialkyl- or diphenyl-disulphide, the temperature of the two solutions being $-78°$ C. or $0°$ C. according to whether an ester or acid of general formula LXV respectively is the reactant. The reaction mixture is then stirred (when $R^4$ is formula LXV is an alkyl group) at $-78°$ C. (a) for one hour when a selenium compound is the reactant or (b) for 30 minutes when a disulphide is the reactant, and subsequently at ambient temperature, e.g. $15°$ C., for 30 minutes, or (when $R^4$ in formula LXV is a hydrogen atom) at room temperature for 1 hour 30 minutes. After addition of, for example, a small amount of a saturated aqueous ammonium chloride solution to the solution of the resulting prostaglandin intermediate to hydrolyze it, the product of formula LXVI is extracted with ethyl acetate.

If desired, the intermediate esters of general formula LXVI wherein $R^4$ represents an alkyl group may be converted to corresponding acids of general formula LXVI, i.e. $R^4$ represents a hydrogen atom, by hydrolysis under alkaline conditions. The hydrolysis of the esters under alkaline conditions may be effected with an aqueous solution of an alkali metal, e.g. sodium or potassium, hydroxide or carbonate in the presence of a water-miscible organic solvent, e.g. tetrahydrofuran or an alkanol containing from 1 to 4 carbon atoms, e.g. methanol.

When the product of general formula LXVI is a compound wherein Q represents $-SeC_6H_5$, the product is then treated with 5 to 7 molecular equivalents of hydrogen peroxide in a mixture of ethyl acetate and tetrahydrofuran or methanol at a temperature of $30°$ C. or below, or with 5 molecular equivalents of sodium periodate in the presence of a lower alkanol, preferably methanol, and water, at a temperature below $20°$ C., preferably for about 24 hours, to form a compound of general formula LXVII wherein $-Q=O$ represents $-Se(O)C_6H_5$, and stirring of the reaction mixture at a temperature of $25°$ to $30°$ C. for one hour results in decomposition of the compound to a trans-$\Delta^2$ compound of general formula LXIIC, which can be separated from the reaction mixture by methods known per se and, if desired, purified by column chromatography on silica gel.

When the product of general formula LXVI is a compound wherein Q is a group $-SR^{16}$, $R^{16}$ being as hereinbefore defined, the product is treated with hydrogen peroxide or sodium periodate in the same way as hereinbefore described for a product of general formula LXVI wherein Q is phenylseleno to obtain a compound of general formula LXVII wheein Q is a group $-SR^{16}$, $R^{16}$ being as hereinbefore defined, which can be separated from the reaction mixture by methods known per se.

When the compound of general formula LXVII is one wherein Q represents an alkylthio group $-SR^{17}$, wherein $R^{17}$ represents an alkyl group containing from 1 to 4 carbon atoms, the compound is dissolved in toluene and the solution stirred preferably in the presence of a small amount of calcium carbonate, at a temperature of $100°$ to $120°$ C. for a period ranging from 5 to 24 hours to decompose the compound to a trans-$\Delta^2$ compound of general formula LXIIC. When the compound of general formula LXVII is one wherein Q represents the phenylthio group, the compound is dissolved in carbon tetrachloride and the solution stirred, preferably in the presence of a small amount of calcium carbonate, at a temperature of about $50°$ C. for a period ranging from 5 to 24 hours to decompose the compound to a trans-$\Delta^2$ compound of general formula LXIIC.

The methods hereinbefore described for the preparation of compounds of general formula LXIIC may be represented by the series of reactions depicted schematically below in Scheme K, wherein the various symbols are as hereinbefore defined, and the depicted carbon to carbon double bond is trans.

SCHEME K

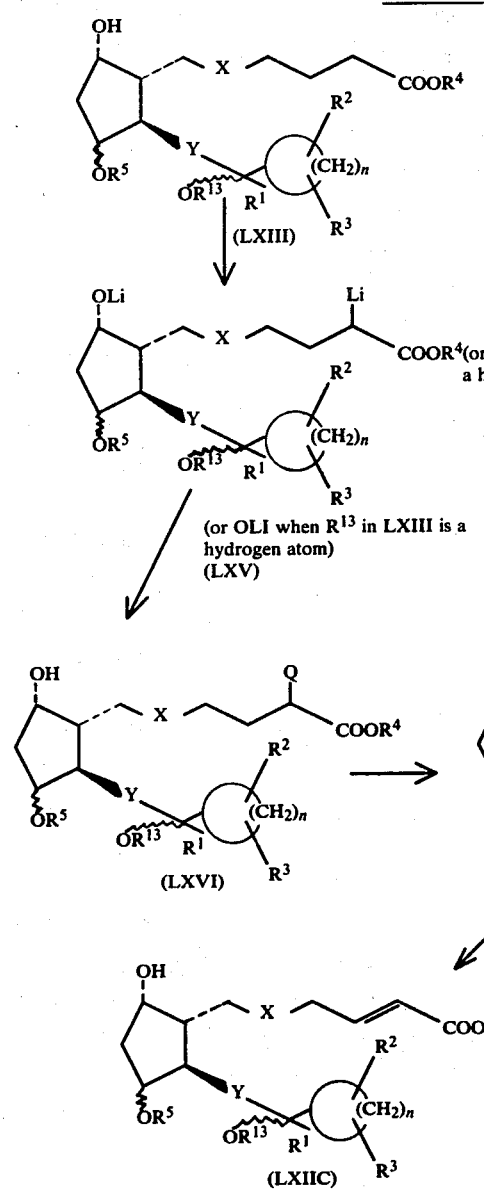

Compounds of general formula LXIIC, wherein Y represents trans-vinylene and the other symbols are as hereinbefore defined (hereinafter depicted as formula LXIID), may be prepared by the series of reactions depicted below in Scheme L, wherein the various symbols are as hereinbefore defined, and the depicted carbon to carbon double bonds are trans.

SCHEME L

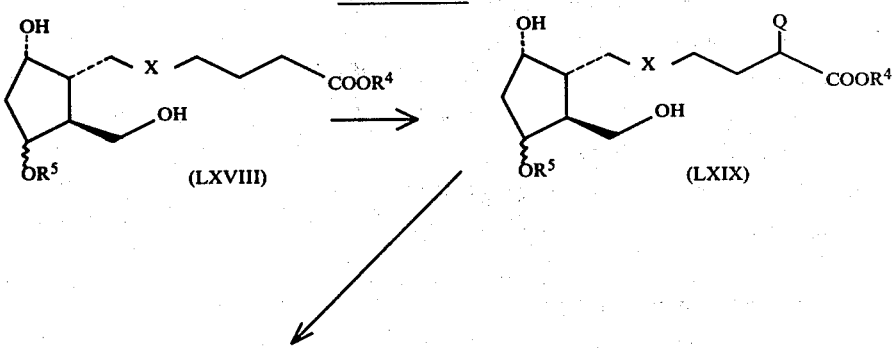

SCHEME L

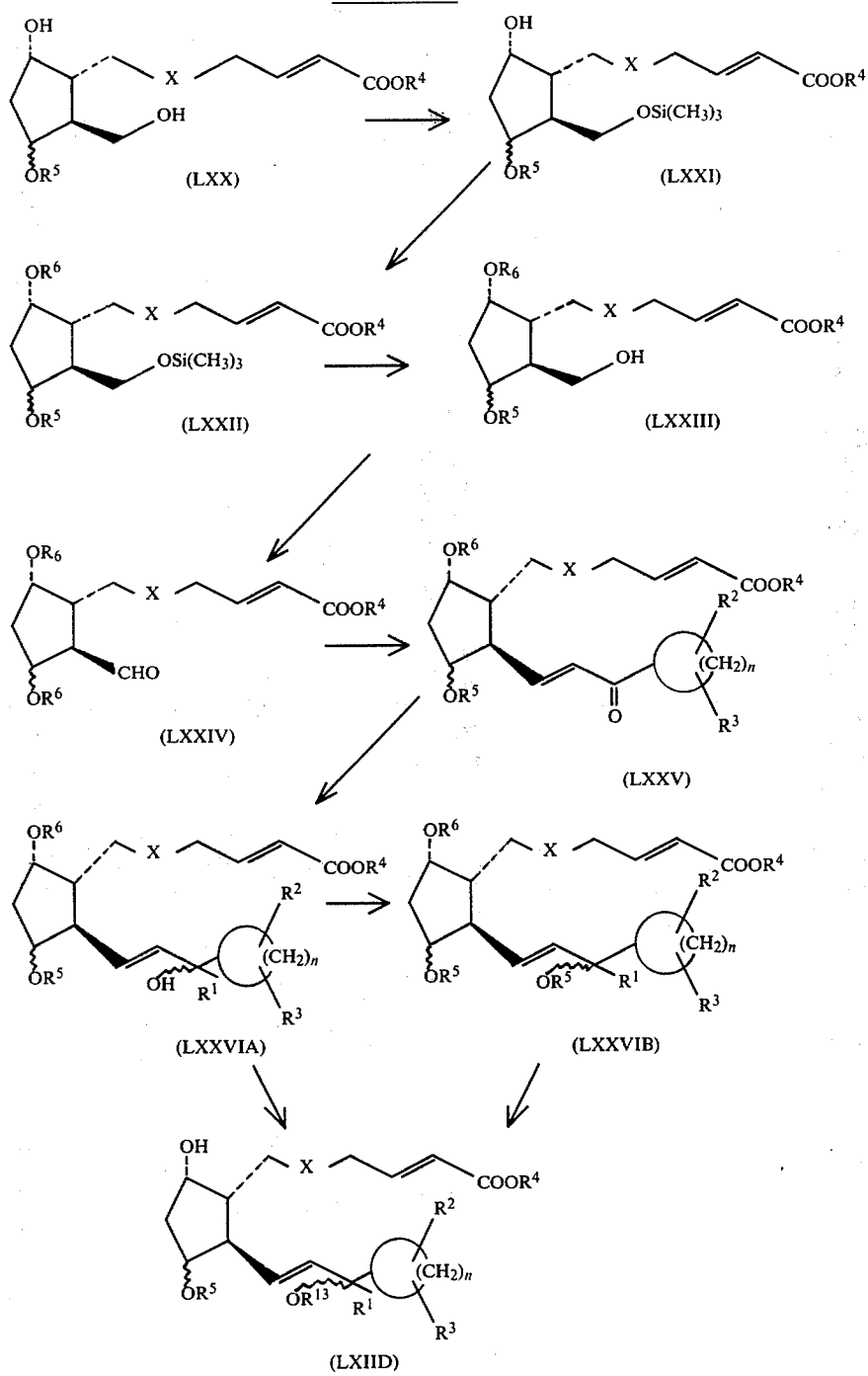

Compounds of general formula LXX may be prepared from compounds of general formula LXVIII by means heretofore mentioned for the conversion of compounds of general formula LXIII to those of general formula LXIIC.

Compounds of general formula LXXIV may be prepared by the series of reactions depicted in Scheme B but replacing the compounds of general formula XV by compounds of general formula LXX.

The conversion of compounds of general formula LXXIV to those of general formula LXXV may be carried out by means heretofore mentioned for the conversion of compounds of general formula XIII to those of general formula XI.

The conversion of compounds of general formula LXXV to those of general formula LXXVIA may be carried out by means heretofore mentioned for the conversion of compounds of general formula XI to those of general formula X.

Compounds of general formula LXXVIA, if desired, may be converted to compounds of general formula LXXVIB by means heretofore mentioned for the conversion of compounds of general formula X to those of general formula XXXIII.

Compounds of general formula LXXVIA or LXXVIB may be converted to compounds of general formula LXIID by means heretofore mentioned for the conversion of compounds of general formula X to those of general formula IX.

If desired, acids of general formula VIIA, VIIB, VIIC, VIIE or VIIF, wherein $R^4$ represents a hydrogen atom and the other symbols are as hereinbefore defined, may be prepared by treatment of corresponding esters of that formula, viz. compounds wherein $R^4$ represents an alkyl group containing from 1 to 4 carbon atoms, (1) when Z represents

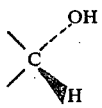

or the ester is of formula VIIA, with an aqueous solution of an alkali metal, e.g. sodium or potassium, hydroxide or carbonate in the presence of a water-miscible organic solvent, for example tetrahydrofuran or an alkanol containing from 1 to 4 carbon atoms, e.g. methanol or ethanol, or (2) when Z represents >C=O, with bakers' yeast [cf. C. J. Sih et al, J. Amer. Chem. Soc., 94, 3643–3644 (1972)].

The PGA compounds of general formula VII wherein A represents a grouping of formula IV are prepared from the corresponding PGE compounds of general formula VII, wherein A represents a grouping of formula VIIB, by subjecting the PGEs to dehydration using an aqueous solution of an organic or inorganic acid having a higher concentration than that employed for hydrolysing the $OR^5$ group of compounds of general formula IX, e.g. 1 N hydrochloric acid, if desired in the presence of cupric chloride, or acetic acid, and heating at a temperature of 30° to 60° C.

It will be appreciated that PGA compounds conforming to general formula VII can be obtained directly from compounds of general formulae XXX, XXXIV and LXII, wherein Z represents >C=O, and XLV when such stronger acidic conditions are utilized to hydrolyze the $OR^5$ groups as the intermediate PGEs will then by dehydrated in situ to PGA compounds.

According to a further feature of the present invention, the compounds of general formula VII, wherein A, W, X, Y, $R^1$, $R^2$, $R^3$ and n are as hereinbefore defined and R represents a straight- or branched-chain alkyl group containing from 1 to 12 carbon atoms, are prepared by esterification of the corresponding acids of formula VII wherein R represents a hydrogen atom by methods known per se, for example by reaction with (i) the appropriate diazoalkane in an inert organic solvent, e.g. diethyl ether, at a temperature of from −10° to 25° C. and preferably 0° C., (ii) the appropriate alcohol in the presence of dicyclohexylcarbodiimide as condensing agent, or (iii) the appropriate alcohol following formation of a mixed anhydride by adding a tertiary amine and pivaloyl halide or an alkylsulphonyl or arylsulphonyl halide (cf. our British Patents Nos. 1362956 and 1364125).

Compounds of general formula VII wherein R represents a hydrogen atom may, if desired, be converted by methods known per se into non-toxic salts.

By the term "non-toxic salts", as used in this specification, is meant salts the cations of which are relatively innocuous to the animal organism when used in therapeutic doses so that the beneficial pharmacological properties of the compounds of general formula VII are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

The non-toxic salts may be prepared from acids of general formula VII wherein R represents a hydrogen atom by, for example, reaction of stoichiometric quantities of an acid of general formula VII and the appropriate base, e.g. an alkali metal hydroxide or carbonate, ammonium hydroxide, ammonia or an amine, in a suitable solvent. The salts may be isolated by lyophilisation of the solution, or, if sufficiently insoluble in the reaction medium, by filtration, if necessary after removal of part of the solvent.

Cyclodextrin clathrates of the prostaglandin analogues of general formula VII may be prepared by dissolving the cyclodextrin in water or an organic solvent which is miscible with water and adding to the solution the prostaglandin analogue in a water-miscible organic solvent. The mixture is then heated and the desired cyclodextrin clathrate product isolated by concentrating the mixture under reduced pressure or by cooling and separating the product by filtration or decantation. The ratio of organic solvent to water may be varied according to the solubilities of the starting materials and products. Preferably the temperature is not allowed to exceed 70° C. during the preparation of the cyclodextrin clathrates. α-, β- and γ-Cyclodextrins or mixtures thereof may be used in the preparation of the cyclodextrin clathrates. Conversion into their cyclodextrin clathrates serves to increase the stability of the prostaglandin analogues.

The present invention also includes, as further features, the hitherto unknown compounds of general formulae IX, XXX, XXXIV, XLV and LXII and the methods heretofore described for their preparation.

The prostaglandin analogues of general formula VII and their cyclodextrin clathrates and, when R represents a hydrogen atom, non-toxic salts possess the valuable pharmacological properties typical of the prostaglandins in a selective fashion, in particular hypotensive activity, inhibitory activity on blood platelet aggregation, inhibitory activity on gastric acid secretion and gastric ulceration, stimulatory activity on uterine contraction and abortifacient, luteolytic and antinidatory activity, and are useful in the treatment of hypertension, in the treatment of disorders of the peripheral circulation, in the prevention and treatment of cerebral thrombosis and myocardial infarction, in the treatment of gastric ulceration, in the termination of pregnancy and induction of labour in pregnant female mammals, in the treatment of impaired fertility and in the control of oestrus, contraception and menstrual regulation in female mammals. For example, in standard laboratory tests, (i) by intravenous administration to the allobarbital-anaesthetized dog,, 15-(3-propylcyclopentyl)-16,17,18,19,20-pentanor-$PGE_2$ methyl ester produces a fall in blood pressure of 30 mm.Hg. lasting 5 minutes at the dose of 5 μg./kg. animal body weight, 15-(3-propylcyclopentyl)-16,17,18,19,20-pentanor-PGE$_1$ methyl ester produces falls in blood pressure of 30 mg.Hg and 42 mm.Hg lasting 15 and 20 minutes at the doses of 0.5 and 1.0 μg/kg. animal body weight, respectively, 15-(1-methyl-3-propylcyclopentyl)-16,17,18,19,20-pentanor-PGE$_2$ methyl ester produces a fall in blood pressure of 33 mm.Hg lasting 29 minutes at the dose of 20 μg./kg. animal body weight, 15-(1-methyl-3-propylcyclopentyl)-16,17,18,19,20-pentanor-PGE$_1$ methyl ester produces falls in blood pressure of 10 mm.Hg and 32 mm.Hg lasting 12 and 27 minutes at the doses of 2.0 and 5.0 μg./kg. animal body weight, respectively, 15-(3-phenylcyclopentyl)-16,17,18,19,20-pentanor-PGE$_2$ methyl ester produces falls in blood pressure of 12 mm.Hg and 24 mm.Hg lasting 4 and 20 minutes at the doses of 20 and 50 μg./kg. animal body weight, respectively, 15-(3-ethylcyclohexyl)-16,17,18,19,20-pentanor-PGE$_2$ methyl ester produces falls in blood pressure of 6 mm.Hg and 26 mm.Hg lasting 3 and 3 minutes at the doses of 5.0 and 10 μg./kg. animal body weight, respectively, 15-(trans-4-ethylcyclohexyl)-16,17,18,19,20-pentanor-PGE$_2$ produces falls in blood pressure of 18 mm.Hg, 20 mm.Hg and 42 mm.Hg lasting 2, 9 and 21 minutes at the doses of 2.0, 5.0 and 10 μg./kg. animal body weight, respectively, 15-(3-propylcyclopentyl)-16,17,18,19,20-pentanor-PGE$_1$ produces falls in blood pressure of 36 mm.Hg and 68 mm.Hg lasting 7 and 18 minutes at the doses of 1.0 and 2.0 μg./kg. animal body weight, respectively, 15-(trans-4-ethylcyclohexyl)-16,17,18,19,20-pentanor-PGE$_1$ produces falls in blood pressure of 12 mm.Hg and 46 mm.Hg lasting 10 and 16 minutes at the doses of 0.2 and 0.5 μg./kg. animal body weight, respectively, 15-(3-ethylcyclohexyl)-16,17,18,19,20-pentanor-PGE$_1$ methyl ester produces falls in blood pressure of 26 mm.Hg and 38 mm.Hg lasting 14 and 16 minutes at the doses of 0.5 and 1.0 μg./kg. animal body weight, respectively, 15-(3-ethylcyclopentyl)-16,17,18,19,20-pentanor-PGE$_2$ produces falls in blood pressure of 16 mm.Hg and 28 mm.Hg lasting 3 and 4 minutes at the doses of 1.0 and 2.0 μg./kg. animal body weight, respectively, 15-(3-propylcyclopentyl)-16,17,18,19,20-pentanor-trans-$\Delta^2$-PGE$_1$ produces falls in blood pressure of 16 mm.Hg, 30 mm.Hg and 50 mm.Hg lasting 5, 6 and 12 minutes at the doses of 0.5, 1.0 and 2.0 μg./kg. animal body weight, respectively, and 15-(3-ethylcyclopentyl)-16,17,18,19,20-pentanor-PGE$_1$ produces falls in blood pressure of 20 mm.Hg, 34 mm.Hg and 54 mm.Hg lasting 3, 6 and 14 minutes at the doses of 0.5, 1.0 and 2.0 μg./kg. animal body weight, respectively, (ii) by oral administration to the conscious spontaneously hypertensive rat, 15-(3-propylcyclopentyl)-16,17,18,19,20-pentanor-PGE$_2$ methyl ester produces falls in blood pressure of 19 mm.Hg, 14 mm.Hg and 14 mm.Hg at 0.5, 1 and 3 hours after administration, respectively at the dose of 0.1 mg.kg. animal body weight, 15-(3-propylcyclopentyl)-16,17,18,19,20-pentanor-PGE$_1$ methyl ester produces falls in blood pressure of 33 mm.Hg and 20 mm.Hg at 0.5 and 1 hours after administration, respectively at the dose of 0.1 mg./kg. animal body weight, 15-(1-methyl-3-propylcyclopentyl)-16,17,18,19,20-pentanor-PGE$_1$ methyl ester produces falls in blood pressure of 35 mm.Hg, 16 mm.Hg and 13 mm.Hg at 0.5, 1 and 3 hours after administration, respectively at the dose of 0.2 mg/kg. animal body weight, 15-(3-propylcyclopentyl)-16,17,18,19,20-pentanor-PGE$_1$ produces falls in blood pressure of 52 mm.Hg, 47 mm.Hg and 41 mm.Hg at 0.5, 1 and 3 hours after administration, respectively at the dose of 1.0 mg./kg. animal body weight, 15-(trans-4-ethylcyclohexyl)-16,17,18,19,20-pentanor-PGE$_1$ produces falls in blood pressure of 24 mm.Hg, 19 mm.Hg and 21 mm.Hg at 0.5, 1 and 3 hours after administration, respectively at the dose of 0.1 mg./kg. animal body weight, 15-(3-ethylcyclohexyl)-16,17,18,19,20-pentanor-PGE$_1$ methyl ester produces falls in blood pressure of 43 mm.Hg, 34 mm.Hg and 34 mm.Hg at 0.5, 1 and 3 hours after administration, respectively at the dose of 1.0 mg./kg. animal body weight, 15-(3-propylcyclopentyl)-16,17,18,19,20-pentanor-trans-$\Delta^2$-PGE$_1$ produces falls in blood pressure of 38 mm.Hg, 32 mm.Hg and 29 mm.Hg at 0.5, 1 and 3 hours after administration, respectively at the dose of 1.0 mg./kg. animal body weight, and 15-(3-ethylcyclopentyl)-16,17,18,19,20-pentanor-PGE$_1$ produces falls in blood pressure of 44 mm.Hg, 35 mm.Hg and 30 mm.Hg at 0.1, 1 and 3 hours after administration, respectively at the dose of 1.0 mg./kg. animal body weight, (iii) in increase of coronary flows in isolated rabbit hearts, 15-(3-propylcyclopentyl)-16,17,18,19,20-pentanor-PGE$_1$, 15-(trans-4-ethylcyclohexyl)-16,17,18,19,20-pentanor-PGE$_1$ and 15-(3-ethylcyclohexyl)-16,17,18,19,20-pentanor-PGE$_1$ methyl ester are 18.7 times, 2.9 times and 1.6 times, respectively, as potent as PGE$_1$, (iv) 15-(3-propylcyclopentyl)-16,17,18,19,20-pentanor-PGE$_1$ methyl ester produces a 50% inhibition of adenosine diphosphate-induced blood platelet aggregation in platelet-rich plasma of human and rats at the concentration of $1.9 \times 10^{-4}$ μg./ml. and $1.6 \times 10^{-3}$ μg./ml., respectively, in comparison with controls, 15-(1-methyl-3-propylcyclopentyl)-16,17,18,19,20-pentanor-PGE$_1$ methyl ester produces a 50% inhibition of adenosine diphosphate-induced blood platelet aggregation in platelet-rich plasma of human and rats at the concentrations of $5.9 \times 10^{-2}$ μg./ml. and $5.2 \times 10^{-2}$ μg./ml., respectively, in comparison with controls, 15-(3-propylcyclopentyl)-16,17,18,19,20-pentanor-PGE$_1$ produces a 50% inhibition of adenosine diphosphate-induced blood platelet aggregation in platelet-rich plasma of human and rats at the concentrations of $9.8 \times 10^{-4}$ μg./ml. and $1.9 \times 10^{-3}$ μg./ml., respectively, in comparison with controls, 15-(trans-4-ethylcyclohexyl)-16,17,18,19,20-pentanor-PGE$_1$ produces a 50% inhibition of adenosine diphosphate-induced blood platelet aggregation in platelet-rich plasma of human and rats at the concentrations of $4.4 \times 10^{-3}$ μg./ml. and $3.1 \times 10^{-3}$ μg./ml., respectively, in comparison with controls, 15-(3-ethylcyclohexyl)-16,17,18,19,20-pentanor-PGE$_1$ methyl ester produces a 50% inhibition of adenosine diphosphate-induced blood platelet aggregation in platelet-rich plasma of human and rats at the concentrations of $1.5 \times 10^{-2}$ μg./ml. and $4.3 \times 10^{-3}$ μg./ml., respectively, in comparison with controls, 15-(3-propylcyclopentyl)-16,17,18,19,20-pentanor-trans-$\Delta^2$-PGE$_1$ produces a 50% inhibition of adenosine diphosphate-induced blood platelet aggregation in platelet-rich plasma of human and rats at the concentrations of $4.4 \times 10^{-4}$ μg./ml. and $8.7 \times 10^{-4}$ μg./ml., respectively, in comparison with controls, 15-(3-ethylcyclopentyl)-16,17,18,19,20-pentanor-PGE$_1$ produces a 50% inhibition of adenosine diphosphate-induced blood platelet aggregation in platelet-rich plasma of human and rats at the concentrations of $1.8 \times 10^{-3}$ μg./ml. and $3.5 \times 10^{-3}$ μg./ml., respectively, in comparison with controls, 15-(3-ethylcyclopentyl)-

13,14-dihydro-16,17,18,19,20-pentanor-PGE$_1$ produces a 50% inhibition of adenosine diphosphate-induced blood platelet aggregation in platelet-rich plasma of human and rats at the concentrations of $1.9\times10^{-3}$ μg./ml. and $5.6\times10^{-3}$ μg./ml., respectively, in comparison with controls, and 15-(3-ethylcyclopentyl)-16,17,18,19,20-pentanor-trans-$\Delta^2$-PGE$_1$ produces a 50% inhibition of adenosine diphosphate-induced blood platelet aggregation in platelet-rich plasma of human and rats at the concentrations of $1.8\times10^{-3}$ μg./ml. and $4.3\times10^{-3}$ μg./ml., respectively, in comparison with controls, (v) 15-(3-propylcyclopentyl)-16,17,18,19,20-pentanor-PGE$_2$ methyl ester, 15-(3-propylcyclopentyl)-16,17,18,19,20-pentanor-PGE$_1$ methyl ester, 15-(1-methyl-3-propylcyclopentyl)-16,17,18,19,20-pentanor-PGE$_1$ methyl ester, 15-(3-propylcyclopentyl)-16,17,18,19,20-pentanor-PGE$_1$, 15-(trans-4-ethylcyclohexyl)-16,17,18,19,20-pentanor-PGE$_1$, and 15-(3-propylcyclopentyl)-16,17,18,19,20-pentanor-trans-$\Delta^2$-PGE$_1$ produce an increase in gastric acid pH from 2.0-2.5 to at least 4.0 in 50% of pentagastrin-treated rats when perfused into the stomach at the rates of 1.0-2.0, 0.4, >>5.0, 2.0-4.0, <1.0 and 1.0-2.0 μg./animal/minute, respectively, (vi) in stress ulceration of rats [produced according to the method of Takagi and Okabe— Jap. J. Pharmac., 18, 9-18 (1968) by soaking rats in a water bath at 19° C. for 6 hours], 15-(3-propylcyclopentyl)-16,17,18,19,20-pentanor-PGE$_2$ methyl ester produces 50.17% inhibition of stress ulceration by oral administration at the dose of 500 μg./kg. animal body weight, 15-(3-propylcyclopentyl)-16,17,18,19,20-pentanor-PGE$_1$ methyl ester produces 52.83% and 76.40% inhibitions of stress ulceration by oral administration at doses of 500 and 1000 μg./kg. animal body weight, respectively, 15-(1-methyl-3-propylcyclopentyl)-16,17,18,19,20-pentanor-PGE$_2$ methyl ester produces 33.83% inhibition of stress ulceration by oral administration at the dose of 200 μg./kg. animal body weight, 15-(1-methyl-3-propylcyclopentyl)-16,17,18,19,20-pentanor-PGE$_1$ methyl ester produces 76.73% and 91.84% inhibitions of stress ulceration by oral administration at doses of 1000 and 2000 μg./kg. animal body weight, respectively, 15-(3-ethylcyclohexyl)-16,17,18,19,20-pentanor-PGE$_2$ methyl ester produces 71.6% inhibition of stress ulceration by oral administration at the dose of 500 μg./kg. animal body weight, 15-(3-propylcyclopentyl)-16,17,18,19,20-pentanor-PGE$_1$ produces 53.90% inhibition of stress ulceration by oral administration at the dose of 500 μg./kg. animal body weight, 15-(trans-4-ethylcyclohexyl)-16,17,18,19,20-pentanor-PGE$_1$ produces 47.90% and 70.59% inhibitions of stress ulceration by oral administration at the doses of 100 and 200 μg./kg. animal body weight, respectively, and 15-(3-ethylcyclohexyl)-16,17,18,19,20-pentanor-PGE$_1$ methyl ester produces 76.0% inhibition of stress ulceration by oral administration at the dose of 500 μg./kg. animal body weight, (vii) 15-(3-propylcyclopentyl)-16,17,18,19,20-pentanor-PGF$_{2\alpha}$ methyl ester, 15-(3-ethylcyclohexyl)-16,17,18,19,20-pentanor-PGF$_{2\alpha}$, 15-(3-propylcyclopentyl)-16,17,18,19,20-pentanor-PGF$_{2\alpha}$, 15-(1-methyl-3-propylcyclopentyl)-16,17,18,19,20-pentanor-PGF$_{2\alpha}$ methyl ester and 15-(trans-4-ethylcyclohexyl)-16,17,18,19,20-pentanor-PGF$_{2\alpha}$ inhibit implantation in pregnant female rats when administered subcutaneously on the 3rd, 4th and 5th days of pregnancy at the daily doses of 0.2, 0.5, 0.5, 1.0 and 0.05 mg./kg. animal body weight, respectively, and (viii) 15-(3-propylcyclopentyl)-16,17,18,19,20-pentanor-PGF$_{2\alpha}$ methyl ester, 15-(3-propylcyclopentyl)-16,17,18,19,20-pentanor-PGE$_2$ methyl ester, 15-(3-propylcyclopentyl)-16,17,18,19,20-pentanor-PGE$_1$ methyl ester, 15-(3-ethylcyclohexyl)-16,17,18,19,20-pentanor-PGF$_{2\alpha}$, 15-(3-propylcyclopentyl)-16,17,18,19,20-pentanor-PGF$_{2\alpha}$, 15-(1-methyl-3-propylcyclopentyl)-16,17,18,19,20-pentanor-PGF$_{2\alpha}$ methyl ester, 15-(1-methyl-3-propylcyclopentyl)-16,17,18,19,20-pentanor-PGE$_2$ methyl ester, 15-(1-methyl-3-propylcyclopentyl)-16,17,18,19,20-pentanor-PGE$_1$ methyl ester, 15-(3-phenylcyclopentyl)-16,17,18,19,20-pentanor-PGF$_{2\alpha}$ methyl ester, 15-(3-phenylcyclopentyl)-16,17,18,19,20-pentanor-PGE$_2$ methyl ester, 15-(3-ethylcyclohexyl)-16,17,18,19,20-pentanor-PGE$_2$ methyl ester, 15-(trans-4-ethylcyclohexyl)-16,17,18,19,20-pentanor-PGF$_{2\alpha}$, 15-(trans-4-ethylcyclohexyl)-16,17,18,19,20-pentanor-PGE$_2$, 15-(3-propylcyclopentyl)-16,17,18,19,20-pentanor-PGE$_1$, 15-(trans-4-ethylcyclohexyl)-16,17,18,19,20-pentanor-PGE$_1$, 15-(3-ethylcyclohexyl)-16,17,18,19,20-pentanor-PGE$_1$ methyl ester, 15-(3-ethylcyclopentyl)-16,17,18,19,20-pentanor-PGE$_2$, 15-(3-ethylcyclopentyl)-16,17,18,19,20-pentanor-PGE$_1$, 15-(3-ethylcyclopentyl)-13,14-dihydro-16,17,18,19,20-pentanor-PGE$_1$ and 15-(3-ethylcyclopentyl)-16,17,18,19,20-pentanor-trans-$\Delta^2$-PGE$_1$ stimulate uterine contraction in the pregnant female rat when administered intravenously on the 20th day of gestation at the doses of 10-20, 5-10, 5, 2-5, 50, 20, 5, 50, 100, 50-100, 100, 50, 100, 10-20, 100, 50-100, 2-5, 10, 20-50 and 20-50 μg./kg. animal body weight, respectively.

The prostaglandin analogues of the present invention, their cyclodextrin clathrates and non-toxic salts can cause diarrhoea, the doses by oral administration of 15-(3-propylcyclopentyl)-16,17,18,19,20-pentanor-PGE$_{2\alpha}$ methyl ester, 15-(3-propylcyclopentyl)-16,17,18,19,20-pentanor-PGE$_2$ methyl ester, 15-(3-propylcyclopentyl)-16,17,18,19,20-pentanor-PGE$_1$ methyl ester, 15-(3-ethylcyclohexyl)-16,17,18,19,20-pentanor-PGF$_{2\alpha}$, 15-(1-methyl-3-propylcyclopentyl)-16,17,18,19,20-pentanor-PGF$_{2\alpha}$ methyl ester, 15-(1-methyl-3-propylcyclopentyl)-16,17,18,19,20-pentanor-PGE$_2$ methyl ester, 15-(1-methyl-3-propylcyclopentyl)-16,17,18,19,20-pentanor-PGE$_1$ methyl ester, 15-(3-phenylcyclopentyl)-16,17,18,19,20-pentanor-PGF$_{2\alpha}$ methyl ester, 15-(3-phenylcyclopentyl)-16,17,18,19,20-pentanor-PGE$_2$ methyl ester, 15-(3-ethylcyclohexyl)-16,17,18,19,20-pentanor-PGE$_2$ methyl ester, 15-(trans-4-ethylcyclohexyl)-16,17,18,19,20-pentanor-PGF$_{2\alpha}$, 15-(trans-4-ethylcyclohexyl)-16,17,18,19,20-pentanor-PGE$_2$, 15-(3-propylcyclopentyl)-16,17,18,19,20-pentanor-PGE$_1$, 15-(trans-4-ethylcyclohexyl)-16,17,18,19,20-pentanor-PGE$_1$, 15-(3-ethylcyclohexyl)-16,17,18,19,20-pentanor-PGE$_1$ methyl ester and 15-(3-propylcyclopentyl)-16,17,18,19,20-pentanor-trans-$\Delta^2$-PGE$_1$, required to produce diarrhoea in 50% of mice so treated are 1-5, 0.7-1.0, 5-10, 0.86, >20, 1.45, >10, 5-10, >2.0, 2.0, 0.45, 0.9, 3.1, >10, >10 and 5-10 mg./kg. animal body weight, respectively.

The following Reference Examples and Examples illustrate the preparation of new prostaglandin analogues of the present invention. In them 'IR', 'NMR' and 'TLC' represent respectively 'Infrared absorption spectrum', 'Nuclear magnetic resonance spectrum' and 'Thin layer chromatography'. Where solvent ratios are specified in chromatographic separations, the ratios are by volume.

REFERENCE EXAMPLE 1

Dimethyl 2-oxo-2-(trans-4-ethylcyclohexyl)ethylphosphonate

Under an atmosphere of nitrogen, 47 ml. of a 1.25 M solution of n-butyllithium in n-hexane were added dropwise to a solution of 7.64 g. of dimethyl methylphosphonate in 120 ml. of tetrahydrofuran at −70° C. After one hour of stirring at −70° C., a solution of 5.63 g. of ethyl trans-4-ethylcyclohexanecarboxylate [c.f. N. L. Allinger and L. A. Freiberg, J. Org. Chem., 31, 894, (1966)] in 30 ml. of tetrahydrofuran was added dropwise at −70° C., and the mixture was stirred at the same temperature for one hour and further stirred at −5° C., for one hour. The reaction mixture was then acidified with acetic acid and concentrated under reduced pressure. The residue was diluted with diethyl ether, washed with water and an aqueous solution of sodium chloride, dried over magnesium sulphate and concentrated under reduced pressure. The residue was purified by distillation to give 5.0 g. of the title compound having the following physical characteristics:

boiling point: 135° C./0.06 mm.Hg;
IR(liquid film): $\nu$=2930, 1860, 1700, 1450, 1260, 1180, 1050, 1030 cm$^{-1}$;
NMR(CDCl$_3$ solution): $\delta$=3.78(6H,d), 3.15(2H,d), 2.8–2.3 (1H,m), 2.1–1.0(11H,m).

REFERENCE EXAMPLE 2

Methyl 9α-acetoxy-11α-(2-tetrahydropyranyloxy)-15-oxo-15-(trans-4-ethylcyclohexyl)-16,17,18,19,20-pentanorprosta-cis-5,trans-13-dienoate Under an atmosphere of nitrogen, a solution of 4.8 g. of dimethyl 2-oxo-2-(trans-4-ethylcyclohexyl)ethylphosphonate (prepared as described in Reference Example 1) in 30 ml. of tetrahydrofuran was added dropwise to a suspension of 590 mg. of sodium hydride (63% content) in 50 ml. of tetrahydrofuran at room temperature with stirring and the mixture was stirred until the solution became clear. To the solution thus obtained was added a solution of 5.1 g. of 1α-acetoxy-2α-(6-methoxycarbonylhex-cis-2-enyl)-3β-formyl-4α-(2-tetrahydropyranyloxy)cyclopentane (prepared as described hereafter) in 40 ml. of tetrahydrofuran and the mixture was stirred at room temperature for 2 hours. The reaction mixture was then acidified with acetic acid and filtered through a pad of magnesium sulphate, and the filtrate was concentrated under reduced pressure. The residue was purified by column chromatography on silica gel using a mixture of benzene and ethyl acetate (7:2) as eluent to give 4.28 g. of the title compound having the following physical characteristics:

TLC (developing solvent, benzene-ethyl acetate=2:1): Rf=0.73;
IR(liquid film): $\nu$=2950, 2860, 1735, 1685, 1660, 1620, 1440, 1370, 1240 cm$^{-1}$;
NMR(CDCl$_3$ solution): $\delta$=6.73(1H,dd), 6.23(1H,d), 5.50–5.15 (2H,m), 5.15–4.85(1H,m), 4.7–4.35(1H,m), 3.64(3H,s), 4.35–3.0(3H,m).

1α-Acetoxy-2α-(6-methoxycarbonylhex-cis-2-enyl)-3β-formyl-4α-(2-tetrahydropyranyloxy)cyclopentane, used as starting material in the above procedure, was prepared from 2-oxa-3-oxo-6-syn-hydroxymethyl-7-anti-acetoxy-cis-bicyclo[3,3,0]octane, [prepared as described by E. J. Corey et al., J. Amer. Chem. Soc., 92, 397 (1970)], as follows:

190 g. of 2-oxa-3-oxo-6-syn-hydroxymethyl-7-anti-acetoxy-cis-bicyclo[3,3,0]octane in 1.5 liters of absolute methanol and 130 g. of potassium hydroxide were stirred at room temperature for one hour, and then successively cooled in an ice-bath, and neutralised with hydrochloric acid. The precipitate was filtered off and the filtrate was concentrated under reduced pressure. The residue was washed with ethanol, and then with ethyl acetate and dried to give 124 g. of 2-oxa-3-oxo-6-syn-hydroxymethyl-7-anti-hydroxy-cis-bicyclo[3,3,-0]octane as white crystallites having the following physical characteristics:

m.p. 119° C.;
IR (KBr tablet): $\nu$: 3350, 2970–2880, 1740, 1480, 1440, 1410, 1380, 1335, 1305, 1270, 1205, 1100, 1080, 1060, 1040, 1020, 1000 and 975 cm$^{-1}$.
NMR (CDCl$_3$+deutero dimethyl sulphoxide solution): $\delta$: 5.10–4.60 (1H,m), 4.29 (2H,s), 4.13–3.77 (1H,m) and 3.38 (2H,d);
TLC (developing solvent, methylene chloride-methanol=20:1); Rf=0.27.

124 g. of 2-oxa-3-oxo-6-syn-hydroxymethyl-7-anti-hydroxy-cis-bicyclo[3,3,0]octane (obtained as described above) were dissolved in absolute pyridine (1.4 liters) and the solution was cooled to −40° C. 74 g. of acetic anhydride were added dropwise and the mixture stirred for 5 hours at −40° to −20° C., and then for 16 hours at 0° C. The pyridine was evaporated off under reduced pressure and the residue was dissolved in 1 liter of ethyl acetate. 200 g. of sodium bisulphate were added, and the mixture stirred vigorously and filtered. The filtrate was concentrated under reduced pressure and the residue was purified by column chromatography on silica gel using a benzene-ethyl acetate mixture (1:3) as eluent to give 112 g. of 2-oxa-3-oxo-6-syn-acetoxymethyl-7-anti-hydroxy-cis-bicyclo[3,3,0]octane as colourless needles having the following physical characteristics:

m.p. 36° to 37° C.;
IR (KBr tablet): $\nu$; 3450, 2960, 2850, 1775, 1740, 1420, 1370, 1250, 1190, 1120, 1090, 1040 and 980 cm$^{-1}$;
NMR (CDCl$_3$ solution): $\delta$; 5.15–4.60 (1H,m), 4.3–3.75 (3H,m), 3.50 (1H,s) and 2.02 (3H,s);
TLC (developing solvent methylene chloride-methanol=20:1); Rf=0.50.

43 g. of 2-oxa-3-oxo-6-syn-acetoxymethyl-7-anti-hydroxy-cis-bicyclo[3,3,0]octane (obtained as described above) were dissolved in 520 ml. of methylene chloride, 25 g. of dihydropyran and 0.52 g. of p-toluenesulphonic acid were added and the mixture stirred for 20 minutes at room temperature. The reaction mixture was neutralised with an aqueous solution of sodium bicarbonate, diluted with ethyl acetate, washed with water, dried and concentrated under reduced pressure to give 56 g. of 2-oxa-3-oxo-6-syn-acetoxymethyl-7-anti-(2-tetrahydropyranyloxy)-cis-bicyclo[3,3,0]octane as a colourless oil having the following physical characteristics:

IR (liquid film): $\nu$; 2950–2840 1775, 1740, 1465, 1440, 1390–1340, 1240, 1180, 1140–1120, 1080, 1040 and 980 cm$^{-1}$;
NMR (CDCl$_3$ solution): $\delta$; 5.2–4.72 (1H,m), 4.72–4.30 (1H,m), 4.2–3.2 (5H,m) and 2.01 (3H,s);
TLC (developing solvent, methylene chloride-methanol=20:1); Rf=0.74.

56 g. of the acetyl ether (prepared as described above) were dissolved in 900 ml. of toluene and the solution was cooled to −60° C. 456 ml. of a 25(w/v)% toluene solution of diisobutylaluminium hydride were added and the mixture stirred for 20 minutes at the same temperature; aqueous methanol was added in order to decompose the excess of diisobutylaluminium hydride. The resulting precipitate was filtered off and the filtrate was dried and concentrated under reduced pressure to give 35.2 g. of 2-oxa-3-hydroxy-6-syn-hydroxymethyl-7-anti-(2-tetrahydropyranyloxy)-cis-bicyclo[3,3,0]octane as a colourless oil having the following physical characteristics:

IR (liquid film): $\nu$; 3400, 2940–2860, 1465-1440, 1380, 1355, 1325, 1260, 1200, 1140, 1120, 1075 and 1020 cm$^{-1}$;

TLC (developing solvent, ethyl acetate): Rf=0.25.

37.6 g. of sodium hydride (content 63.5%) were suspended in 400 ml. of dimethyl sulphoxide and the suspension was stirred at 70° C., for 1.5 hours to obtain sodium methylsulphinylmethylide. The reaction mixture was allowed to cool to room temperature and then added dropwise to a solution of 226 g. of (4-carboxybutyl)triphenylphosphonium bromide in 460 ml. of dimethyl sulphoxide, the reaction temperature being kept within the range 20° to 25° C.

A solution of 35.2 g. of 2-oxa-3-hydroxy-6-syn-hydroxymethyl-7-anti-(2-tetrahydropyranyloxy)-cis-bicyclo[3,3,0]octane (prepared as described above) in 90 ml. of dimethyl sulphoxide was added to the above reaction mixture and the solution was stirred at 35° to 40° C., for 1.5 hours. The reaction mixture was then poured into 6 liters of ice-water and the neutral substances were removed by extraction with an ethyl acetate-diethyl ether mixture (1:1). The aqueous layer was acidified to pH 2 with saturated aqueous oxalic acid solution and extracted with a diethyl ether-n-pentane mixture (1:1). The organic layer was washed with water, dried over sodium sulphate and concentrated under reduced pressure. The residue was subjected to column chromatography on silica gel using a benzene-methanol mixture (10:1) as eluent to give 35 g. of 2α-(6-carboxyhex-cis-2-enyl)-3β-hydroxymethyl-4α-(2-tetrahydropyranyloxy)cyclopentan-1α-ol as a colourless oil having the following physical characteristics:

IR (liquid film): $\nu$; 3400, 2940–2860, —2300, 1710, 1450, 1435, 1400, 1355, 1245, 1200, 1140, 1120, 1075 and 1025 cm$^{-1}$;

NMR (CDCl$_3$ solution): $\delta$; 6.20 (3H,s), 5.50–5.10 (2H,m), 4.75–4.36 (1H,m), 4.24–3.85 (2H,m), and 3.85–3.0 (4H,m);

TLC (developing solvent, chloroform-tetrahydrofuran-acetic acid=10:2:1); Rf=0.53.

To a solution of 18.8 g. of 2α-(6-carboxyhex-cis-2-enyl)-3β-hydroxymethyl-4α-(2-tetrahydropyranyloxy)-cyclopentan-1α-ol (obtained as described above) in 130 ml. of diethyl ether, a freshly prepared ethereal solution of diazomethane was added with cooling in an ice-bath until the reaction mixture showed a pale yellow colour. The reaction mixture was concentrated in vacuo, and the residue was subjected to column chromatography on silica gel using a cyclohexane-ethyl acetate mixture (2:1) as eluent to give 15.4 g. of 2α-(6-methoxycarbonylhex-cis-2-enyl)-3β-hydroxymethyl-4α-(2-tetrahydropyranyloxy)-cyclopentan-1α-ol as a colourless oil having the following physical characteristics:

IR (liquid film): $\nu$; 3450, 2950, 2870, 1740, 1440, 1360, 1325, 1250, 1200, 1140, 1120, 1080 and 1025 cm$^{-1}$;

NMR (CDCl$_3$ solution): $\delta$; 5.55–5.00 (2H,m), 4.78–4.30 (1H,m), 4.20–3.06 (6H,m), 3.55 (3H,s) and 2.97 (2H,s);

TLC (developing solvent, methylene chloride-methanol=19:1); Rf=0.43.

13.1 g. of 2α-(6-methoxycarbonylhex-cis-2-enyl)-3β-hydroxymethyl-4α-(2-tetrahydropyranyloxy)-cyclopentan-1α-ol (obtained as described above) were dissolved in 250 ml. of absolute methylene chloride, and 25 ml. of pyridine were added. The air in the apparatus was replaced with nitrogen and the contents cooled to −20° C. To the reaction mixture was added dropwise a solution of 5.1 ml. of trimethylchlorosilane in 30 ml. of methylene chloride with stirring, followed by stirring at the same temperature for 30 minutes. A sample of the product thus obtained had the following physical characteristic:

TLC (developing solvent, benzene - ethyl acetate=2:1); Rf=0.61.

A solution of 2.9 ml. of acetyl chloride in 20 ml. of methylene chloride was added dropwise to the above reaction mixture and the solution was stirred at room temperature for 30 minutes. Then 2 ml. of ethanol were added to decompose the excess of acetyl chloride. Pyridine in the reaction mixture was neutralised by the addition of 50 g. of sodium bisulphate, and the resulting precipitate was filtered off. The filtrate was concentrated under reduced pressure to give a residue having the following physical characteristic:

TLC (developing solvent, benzene - ethyl acetate=2:1); Rf=0.82.

The residue was dissolved in 300 ml. of ethyl acetate, 100 ml. of aqueous oxalic acid solution were added and the solution was stirred vigorously at room temperature. The organic layer was separated, washed successively with water, aqueous sodium bisulphate solution, water and aqueous sodium chloride solution, dried with sodium sulphate and concentrated under reduced pressure to give 13.7 g. of crude product. The crude product was subjected to column chromatography on silica gel using a benzene-ethyl acetate mixture (3:1) as eluent to give 7.45 g. of 1α-acetoxy-2α-(6-methoxycarbonylhex-cis-2-enyl)-3β-hydroxymethyl-4α-(2-tetrahydropyranyloxy)-cyclopentane, 2.40 g. of 1α-hydroxy-2α-(6-methoxycarbonylhex-cis-2-enyl)-3β-hydroxymethyl-4α-(2-tetrahydropyranyloxy)-cyclopentane, 720 mg. of 1α-hydroxy-2α-(6-methoxycarbonylhex-cis-2-enyl)-3β-acetoxymethyl-4α-(2-tetrahydropyranyloxy)-cyclopentane, and 1.45 g. of 1α-acetoxy-2α-(6-methoxycarbonylhex-cis-2-enyl)-3β-acetoxymethyl-4α-(2-tetrahydropyranyloxy)-cyclopentane.

1α-Acetoxy-2α-(6-methoxycarbonylhex-cis-2-enyl)3β-hydroxymethyl-4α-(2-tetrahydropyranyloxy)-cyclopentane had the following physical characteristics:

IR (liquid film): $\nu$; 3450, 3000, 2950, 2870, 1740, 1440, 1380, 1330, 1250, 1200, 1160, 1140, 1080, 1030, 980, 920, 875 and 815 cm$^{-1}$;

NMR (CDCl$_3$ solution): $\delta$; 5.45–5.27 (2H,m), 5.16–4.92 (1H,m), 4.76–4.46 (1H,m), 4.27–3.96 (1H,m), 3.67 (3H,s), 2.98–2.64 (1H,m) and 2.05 (3H,s);

TLC (developing solvent, benzene - ethyl acetate=2:1); Rf=0.27.

Under an atmosphere of nitrogen, 4.4 ml. of pyridine were dissolved in 80 ml. of dichloromethane, 2.88 g. of chromium trioxide were added with stirring and then the mixture was stirred for 15 minutes. 12 g. of infusorial earth were added to the reaction mixture, and then there was added a solution of 956 mg. of 1α-acetoxy-2α-(6-methoxycarbonylhex-cis-2-enyl)-3β-hydroxymethyl-4α-(2-tetrahydropyranyloxy)-cyclopentane (prepared as described above) in 20 ml. of dichloromethane. After stirring for 10 minutes, 20 g. of sodium bisulphate were added to the reaction mixture and stirring continued for a further 10 minutes. The resulting precipitate was filtered off and the filtrate was concentrated under reduced pressure. The residue was subjected to silica gel column chromatography using a benzene-ethyl acetate mixture (5:1) as eluent to give 768 mg. of 1α-acetoxy-2α-(6-methoxycarbonylhex-cis-2-enyl)-3β-formyl-4α-(2-tetrahydropyranyloxy)cyclopentane as a colourless oil having the following physical characteristics:

IR (liquid film): ν; 3000, 2950, 2860, 2725, 1740, 1440, 1380, 1325, 1255, 1200, 1165, 1140, 1085, 1030, 980, 920, 880 and 820 cm$^{-1}$;

NMR (CDCl$_3$ solution): δ; 9.85-9.68 (1H,m), 5.45-4.96 (1H,m), 4.68-4.48 (1H,m), 4.48-4.25 (1H,m), 3.67 (3H,s), and 2.08 (3H,s);

TLC (developing solvent, benzene - ethyl acetate = 2:1); Rf = 0.66.

REFERENCE EXAMPLE 3

Methyl 9α-acetoxy-11α-(2-tetrahydropyranyloxy)-15S-hydroxy-15-(trans-4-ethylcyclohexyl)-16,17,18,19,20-pentanorprosta-cis-5, trans-13-dienoate To a solution of 4.28 g. of methyl 9α-acetoxy-11α-(2-tetrahydropyranyloxy)-15-oxo-15-(trans-4-ethylcyclohexyl)-16,17,18,19,20-pentanorprosta-cis-5,trans-13-dienoate (prepared as described in Reference Example 2) in a mixture of 40 ml. of ethanol and 15 ml. of tetrahydrofuran was added portionwise 0.92 g. of sodium borohydride at −50° C. After one hour of stirring at −50° to −40° C., the reaction mixture was acidified with acetic acid and concentrated under reduced pressure. The residue was diluted with ethyl acetate, washed with water, an aqueous solution of sodium bicarbonate, water and an aqueous solution of sodium chloride, dried over magnesium sulphate and concentrated under reduced pressure. The residue was purified by column chromatography on silica gel using a mixture of benzene and ethyl acetate (3:1) as eluent to give 1.92 g. of the title compound, 570 mg. of its 15R-hydroxy isomer and 160 mg. of their mixture. The title compound showed the following physical characteristics:

TLC (developing solvent, benzene-ethyl acetate = 2:1): Rf = 0.36, (15R-hydroxy isomer, Rf = 0.50);

IR (liquid film): ν = 3500, 2940, 2860, 1730, 1430, 1370, 1240, 1020, 970 cm$^{-1}$;

NMR(CDCl$_3$ solution): δ = 5.7-5.4 (2H,m), 5.4-5.15(2H,m), 5.15-4.8(1H,m), 4.7-4.4(1H,m), 3.65 (3H,s), 4.2-3.1(4H,m), 2.03(3H,s).

EXAMPLE 1

9α,15S-Dihydroxy-11α-(2-tetrahydropyranyloxy)-15-(trans-4-ethylcyclohexyl)-16,17,18,19,20-pentanorprosta-cis-5, trans-13-dienoic acid To a solution of 457 mg. of methyl 9α-acetoxy-11α-(2-tetrahydropyranyloxy)-15S-hydroxy-15-(trans-4-ethylcyclohexyl)-16,17,18,19,20-pentanorprosta-cis-5, trans-13-dienoate (prepared as described in Reference Example 3) in 6 ml. of methanol was added 3 ml. of a 2 N aqueous solution of potassium hydroxide and the mixture was stirred at 45° to 50° C., for 15 minutes. The reaction mixture was acidified with acetic acid, diluted with 200 ml. of ethyl acetate, washed with water and an aqueous solution of sodium chloride, dried over magnesium sulphate and concentrated under reduced pressure to give 376 mg. of the crude title compound having the following physical characteristics:

TLC (developing solvent, benzene-ethyl acetate = 1:2): Rf = 0.13;

IR (liquid film): ν = 3430, 3300-2300, 2940, 2860, 1710, 1440, 1020, 970 cm$^{-1}$;

NMR(CDCl$_3$ solution): δ = 5.8-4.8 (7H,m), 4.8-4.5 (1H,m), 4.3-3.1 (5H,m).

EXAMPLE 2

9α,11α,15S-Trihydroxy-15-(trans-4-ethylcyclohexyl)-16,17,18,19,20-pentanorprosta-cis-5,trans-13-dienoic acid [or 15-(trans-4-ethylcyclohexyl)-16,17,18,19,20-pentanor-PGF$_{2α}$]

376 mg. of 9α,15S-dihydroxy-11α-(2-tetrahydropyranyloxy)-15-(trans-4-ethylcyclohexyl)-16,17,18,19,20-pentanorprosta-cis-5,trans-13-dienoic acid (prepared as described in Example 1) were dissolved in a mixture of 1 ml. of tetrahydrofuran and 10 ml. of a 65% aqueous solution of acetic acid and the mixture was stirred at 45° C. for one hour. The reaction mixture was diluted with ethyl acetate, washed with water and an aqueous solution of sodium chloride, dried over magnesium sulphate and concentrated under reduced pressure. The residue was purified by column chromatography on silica gel using a mixture of cyclohexane and ethyl acetate (1:3) as eluent to give 120 mg. of the title compound having the following physical characteristics:

TLC (developing solvent, chloroform-tetrahydrofuran-acetic acid = 10:2:1): Rf = 0.07;

IR(CHCl$_3$ solution): ν = 3400, 3300-2300, 2940, 2860, 1700, 975 cm$^{-1}$;

NMR(CDCl$_3$+acetone-d$_6$ solution): δ = 6.1-4.7 (8H, m), 4.4-3.5 (3H, m).

REFERENCE EXAMPLE 4

Methyl 9α-acetoxy-11α,15S-bis(2-tetrahydropyranyloxy)-15-(trans-4-ethylcyclohexyl)-16,17,18,19,20-pentanorprosta-cis-5,trans-13-dienoate To a solution of 1.32 g. of methyl 9α-acetoxy-11α-(2-tetrahydropyranyloxy)-15S-hydroxy-15-(trans-4-ethylcyclohexyl)-16,17,18,19,20-pentanorprosta-cis-5,trans-13-dienoate (prepared as described in Reference Example 3) in 10 ml. of methylene chloride were added 4.8 g. of p-toluenesulphonic acid and 0.48 ml. of 2,3-dihydropyran, and the mixture was stirred at room temperature for 15 minutes. The reaction mixture was diluted with 200 ml. of ethyl acetate, washed with water, an aqueous solution of sodium bicarbonate, water and an aqueous solution of sodium chloride, dried over magnesium sulphate and concentrated under reduced pressure to give 1.55 g. of the crude title compound having the following physical characteristics:

TLC (developing solvent, benzene-ethyl acetate = 4:1): Rf = 0.36;

IR (liquid film): ν = 2940, 2860, 1730, 970 cm$^{-1}$;

NMR(CDCl$_3$ solution): δ = 5.7-5.1 (4H, m), 5.1-4.8 (1H,m), 4.8-4.3 (2H,m), 4.3-3.1 (6H,m), 3.60 (3H, s), 2.0 (3H,s).

EXAMPLE 3

9α-Hydroxy-11α,15S-bis(2-tetrahydropyranyloxy)-15-(trans-4-ethylcyclohexyl)-16,17,18,19,20-pentanorprosta-cis-5,trans-13-dienoic acid By proceeding as described in Example 1 but replacing the methyl 9α-acetoxy-11α-(2-tetrahydropyranyloxy)-15S-hydroxy-15-(trans-4-ethylcyclohexyl)-16,17,18,19,20-pentanorprosta-cis-5,trans-13-dienoate by 1.55 g. of methyl 9α-acetoxy-11α,15S-bis(2-tetrahydropyranyloxy)-15-(trans-4-ethylcyclohexyl)-16,17,18,19,20-pentanorprosta-cis-5,trans-13-dienoate (prepared as described in Reference Example 4) dissolved in 15 ml. of methanol and utilizing 6 ml. of a 2 N aqueous solution of potassium hydroxide, there were obtained 1.4 g. of the title compound having the following physical characteristics:

TLC (developing solvent, benzene-ethyl acetate=2:1): Rf=0.06;

IR (liquid film): $\nu$=3450, 3300-2300, 2940, 2860, 1720, 1710, 970 cm$^{-1}$;

NMR(CDCl$_3$ solution): $\delta$=6.9-6.0 (2H,m), 5.7-5.1 (4H,m), 4.9-4.4 (2H,m), 4.4-3.1 (7H,m).

EXAMPLE 4

9-Oxo-11α,15S-bis(2-tetrahydropyranyloxy)-15-(trans-4-ethylcyclohexyl)-16,17,18,19,20-pentanorprosta-cis-5,trans-13-dienoic acid To a solution of 580 mg. of 9α-hydroxy-11α,15S-bis(2-tetrahydropyranyloxy)-15-(trans-4-ethylcyclohexyl)-16,17,18,19,20-pentanorprosta-cis-5,trans-13-dienoic acid (prepared as described in Example 3) in 18 ml. of diethyl ether was added 18 ml. of a chromic acid solution (obtained from 2 g. of chromium trioxide, 6.75 g. of manganese sulphate, 2.23 ml. of sulphuric acid in 50 ml. of water) at 5° C. and the mixture was stirred at 5° C. for 1.5 hours. The reaction mixture was extracted with diethyl ether. The extract was washed with water and an aqueous solution of sodium chloride, dried over magnesium sulphate and concentrated under reduced pressure. The residue was purified by column chromatography on silica gel using a mixture of benzene and ethyl acetate (1:1) as eluent to give 455 mg. of the title compound having the following physical characteristics:

TLC (developing solvent, benzene-ethyl acetate=1:2): Rf=0.40;

IR (liquid film): $\nu$=3300-2300, 2940, 2860, 1730, 1700, 970 cm$^{-1}$;

NMR(CDCl$_3$ solution): $\delta$=8.7-7.8 (1H,m), 5.8-5.2 (4H,m), 4.9-4.45 (2H,m), 4.45-3.15 (6H,m).

EXAMPLE 5

9-Oxo-11α,15S-dihydroxy-15-(trans-4-ethylcyclohexyl)-16,17,18,19,20-pentanorprosta-cis-5,trans-13-dienoic acid [or
15-(trans-4-ethylcyclohexyl)-16,17,18,19,20-pentanor-PGE$_2$]

By proceeding as described in Example 2 but replacing the 9α,15S-dihydroxy-11α-(2-tetrahydropyranyloxy)-15-(trans-4-ethylcyclohexyl)-16,17,18,19,20-pentanorprosta-cis-5,trans-13-dienoic acid by 455 mg. of 9-oxo-11α,15S-bis(2-tetrahydropyranyloxy)-15-(trans-4-ethylcyclohexyl)-16,17,18,19,20-pentanorprosta-cis-5,trans-13-dienoic acid (prepared as described in Example 4) dissolved in a mixture of 1 ml. of tetrahydrofuran and 10 ml. of a 65% aqueous solution of acetic acid, there were obtained 208 mg. of the title compound having the following physical characteristics:

TLC (developing solvent, chloroform-tetrahydrofuran-acetic acid=10:2:1): Rf=0.08;

IR(CHCl$_3$ solution): $\nu$=3400, 3300-2300, 2940, 2860, 1730, 1700, 970 cm$^{-1}$;

NMR(CDCl$_3$ solution): $\delta$=5.85-5.10 (7H,m), 4.2-3.6 (2H,m), 2.75 (1H,dd).

EXAMPLE 6

9α-Hydroxy-11α,15S-bis(2-tetrahydropyranyloxy)-15-(trans-4-ethylcyclohexyl)-16,17,18,19,20-pentanorprost-trans-13-enoic acid 820 mg. of 9α-hydroxy-11α,15S-bis(2-tetrahydropyranyloxy)-15-(trans-4-ethylcyclohexyl)-16,17,18,19,20-pentanorprosta-cis-5,trans-13-dienoic acid (prepared as described in Example 3) were hydrogenated at a pressure of one atmosphere in 40 ml. of methanol containing 270 mg. of 5% palladium on charcoal. The reduction was stopped after the absorption of one equivalent of hydrogen gas. The catalyst was removed by filtration and the filtrate was concentrated under reduced pressure to give 760 mg. of the crude title compound having the following physical characteristics:

TLC (developing solvent, methylene chloride-methanol=20:1): Rf=0.26;

IR (liquid film): $\nu$=3450, 3300-2300, 2940, 2860, 1705, 970 cm$^{-1}$;

NMR(CDCl$_3$ solution): $\delta$=6.25 (2H, broad s), 5.60-5.15 (2H,m), 4.8-4.5 (2H,m).

EXAMPLE 7

9-Oxo-11α,15S-bis(2-tetrahydropyranyloxy)-15-(trans-4-ethylcyclohexyl)-16,17,18,19,20-pentanorprost-trans-13-enoic acid By proceeding as described in Example 4 but replacing the 9α-hydroxy-11α,15S-bis(2-tetrahydropyranyloxy)-15-(trans-4-ethylcyclohexyl)-16,17,18,19,20-pentanorprosta-cis-5,trans-13-dienoic acid by 760 mg. of 9α-hydroxy-11α,15S-bis(2-tetrahydropyranyloxy)-15-(trans-4-ethylcyclohexyl)-16,17,18,19,20-pentanorprost-trans-13-enoic acid (prepared as described in Example 6) dissolved in 24 ml. of diethyl ether and utilizing 24 ml. of the chromic acid solution there were obtained 620 mg. of the title compound having the following physical characteristics:

TLC (developing solvent, methylene chloride-methanol=20:1): Rf=0.47;

IR (liquid film): $\nu$=3300-2300, 2940, 2860, 1730, 1700, 970 cm$^{-1}$;

NMR(CDCl$_3$ solution): $\delta$=8.65 (1H, broad s), 5.75-5.30 (2H,m), 4.8-4.5 (2H,m), 2.77 (1H,dd).

EXAMPLE 8

9-Oxo-11α,15S-dihydroxy-15-(trans-4-ethylcyclohexyl)-16,17,18,19,20-pentanorprost-trans-13-enoic acid [or
15-(trans-4-ethylcyclohexyl)-16,17,18,19,20-pentanor-PGE$_1$]

By proceeding as described in Example 2 but replacing the 9α,15S-dihydroxy-11α-(2-tetrahydropyranyloxy)-15-(trans-4-ethylcyclohexyl)-16,17,18,19,20-pentanorprosta-cis-5,trans-13-dienoic acid by 620 mg. of 9-oxo-11α,15S-bis(2-tetrahydropyranyloxy)-15-(trans-4-ethylcyclohexyl)-16,17,18,19,20-pentanorprost-trans-13-enoic acid (prepared as described in Example 7)

dissolved in a mixture of 1.1 ml. of tetrahydrofuran and 11 ml. of a 65% aqueous solution of acetic acid, there were obtained 165 mg. of the title compound as a white powder having the following physical characteristics:
melting point: 120°-123° C.;
TLC (developing solvent, chloroform-tetrahydrofuran-acetic acid=10:2:1): Rf=0.14;
IR(CHCl$_3$ solution): $\nu$=3400, 3300-2400, 2930, 2860, 1730, 1700, 965 cm$^{-1}$;
NMR(CDCl$_3$ solution): $\delta$=5.7-5.5 (2H,m), 5.42 (3H,broad s), 4.23-3.7 (2H,m), 2.74 (1H,dd).

REFERENCE EXAMPLE 5

Dimethyl 2-oxo-2-(3-propylcyclopentyl)ethylphosphonate 17 ml. of a 2 M solution of n-butyllithium in diethyl ether were added dropwise with stirring, under an atmosphere of nitrogen, to a solution of 4.2 g. of dimethyl methylphosphonate in 40 ml. of dry tetrahydrofuran at −50° to −60° C. After stirring for 10 minutes, 2.9 g. of 1-methoxycarbonyl-3-propylcyclopentane in 10 ml. of dry tetrahydrofuran were added dropwise at −78° C. and the reaction mixture was stirred for 4 hours at −78° C. and further stirred overnight at 0° C. The reaction mixture was then acidified with acetic acid and concentrated under reduced pressure. The residue was diluted with diethyl ether, washed with water, dried over magnesium sulphate and concentrated under reduced pressure. The residue was purified by column chromatography on silica gel using ethyl acetate as eluent to give 3.1 g. of the title compound having the following physical characteristics:
IR (liquid film): $\nu$; 2950, 2850, 1710, 1450, 1260, 1190, 1040, 820 cm$^{-1}$;
NMR (CDCl$_3$ solution): $\delta$; 3.83 (6H,d), 3.15 (2H,d), 3.82-2.95 (1H,m), 2.21-1.13 (11H,m), 0.95 (3H,t).

REFERENCE EXAMPLE 6

Methyl 9α-acetoxy-11α-(2-tetrahydropyranyloxy)-15-oxo-15-(3-propylcyclopentyl)-16,17,18,19,20-pentanorprosta-cis-5,trans-13-dienoate By proceeding as described in Reference Example 2 but replacing the dimethyl 2-oxo-2-(trans-4-ethylcyclohexyl)-ethylphosphonate by 3.1 g. of dimethyl 2-oxo-2-(3-propylcyclopentyl)ethylphosphonate (prepared as described in Reference Example 5) dissolved in 10 ml. of dry tetrahydrofuran and utilising a suspension of 0.450 g. of sodium hydride (63% content) in 65 ml. of dry tetrahydrofuran and 3.8 g. of 1α-acetoxy-2α-(6-methoxycarbonylhex-cis-2-enyl)-3β-formyl-4α-(2-tetrahydropyranyloxy)cyclopentane (prepared as described in Reference Example 2) in 10 ml. of dry tetrahydrofuran, there were obtained 3.9 g. of the title compound having the following physical characteristics:
TLC (developing solvent, benzene-ethyl acetate=4:1): Rf=0.547;
IR (liquid film): $\nu$=2950, 2850, 1740, 1700, 1670, 1630, 1540, 1380, 1250, 1200, 1140, 1030, 980 cm$^{-1}$;
NMR(CDCl$_3$ solution): $\delta$=6.72 (1H,dd), 6.20 (1H,d), 5.48-5.18 (2H,m), 5.17-4.90 (1H,m), 4.65-4.44 (1H,m), 4.21-3.20 (7H,m), 2.60-1.05 (29H,m), 0.95 (3H,t).

REFERENCE EXAMPLE 7

Methyl 9α-acetoxy-11α-(2-tetrahydropyranyloxy)-15S-hydroxy-15-(3-propylcyclopentyl)-16,17,18,19,20-pentanorprosta-cis-5,trans-13-dienoate By proceeding as described in Reference Example 3 but replacing the methyl 9α-acetoxy-11α-(2-tetrahydropyranyloxy)-15-oxo-15-(trans-4-ethylcyclohexyl)-16,17,18,19,20-pentanorprosta-cis-5,trans-13-dienoate by 3.91 g. of methyl 9α-acetoxy-11α-(2-tetrahydropyranyloxy)-15-oxo-15-(3-propylcyclopentyl)-16,17,18,19,20-pentanorprosta-cis-5,trans-13-dienoate (prepared as described in Reference Example 6) dissolved in 40 ml. of methanol and utilizing 0.574 g. of sodium borohydride, there were obtained 1.592 g. of the title compound and 1.408 g. of its 15R-hydroxy isomer. The title compound showed the following physical characteristics:
TLC (developing solvent, benzene-ethyl acetate=2:1); Rf=0.34, (15R-hydroxy isomer, Rf=0.50);
IR (liquid film): $\nu$=3450, 2950, 2850, 1740, 1420, 1380, 1250, 1140, 1080, 1020, 980 cm$^{-1}$;
NMR(CDCl$_3$ solution): $\delta$=5.75-5.18 (4H,m), 5.18-4.90 (1H,m), 4.73-4.55 (1H,m), 4.20-3.30 (7H,m), 2.05 (3H,s), 0.95 (3H,t).

EXAMPLE 9

Methyl 9α,15S-dihydroxy-11α-(2-tetrahydropyranyloxy)-15-(3-propylcyclopentyl)-16,17,18,19,20-pentanorprosta-cis-5,trans-13-dienoate A solution of 0.350 g. of methyl 9α-acetoxy-11α-(2-tetrahydropyranyloxy)-15S-hydroxy-15-(3-propylcyclopentyl)-16,17,18,19,20-pentanorprosta-cis-5,trans-13-dienoate (prepared as described in Reference Example 7) in 10 ml. of dry methanol was stirred with 0.370 g. of anhydrous potassium carbonate at 40° C., for one hour, then cooled to 0° C., and acidified with acetic acid. The reaction mixture was diluted with ethyl acetate, washed with an aqueous solution of sodium bicarbonate and an aqueous solution of sodium chloride, dried over magnesium sulphate and concentrated under reduced pressure to give 0.321 g. of the title compound having the following physical characteristics:
TLC (developing solvent, benzene-ethyl acetate=1:1): Rf=0.458;
IR (liquid film): $\nu$=3450, 2950, 2850, 1740, 1420, 1380, 1240, 1200, 1140, 1020, 980 cm$^{-1}$;
NMR(CDCl$_3$ solution): $\delta$=5.75-5.18 (4H,m), 4.78-4.55 (1H,m), 4.76-3.22 (8H,m), 0.95 (3H,t).

EXAMPLE 10

Methyl 9α,11α-15S-trihydroxy-15-(3-propylcyclopentyl)-16,17,18,19,20-pentanorprosta-cis-5,trans-13-dienoate [or 15-(3-propylcyclopentyl)-16,17,18,19,20-pentanor-PGF$_2$α methyl ester]

By proceeding as described in Example 2 but replacing the 9α,15S-dihydroxy-11α-(2-tetrahydropyranyloxy)-15-(trans-4-ethylcyclohexyl)-16,17,18,19,20-pentanorprosta-cis-5,trans-13-dienoic acid by 321 mg. of methyl 9α,15S-dihydroxy-11α-(2-tetrahydropyranyloxy)-15-(3-propylcyclopentyl)-16,17,18,19,20-pentanorprosta-cis-5,trans-13-dienoate (prepared as described in Example 9) dissolved in a mixture of 1 ml. of tetrahydrofuran and 10 ml. of 65% aqueous acetic acid, there were obtained 178 mg. of the title compound having the following physical characteristics:

TLC (developing solvent, chloroform-tetrahydrofuran-acetic acid=10:2:1): Rf=0.233;

IR (liquid film): $\nu=3350$, 2950, 2850, 1740, 1440, 1380, 1250, 1180, 1060, 980 cm$^{-1}$;

NMR(CDCl$_3$ solution): $\delta=5.60$-5.13 (4H,m), 4.25-3.50 (6H,m), 0.95 (3H,t).

REFERENCE EXAMPLE 8

Methyl 9α-acetoxy-11α,15S-bis(2-tetrahydropyranyloxy)-15-(3-propylcyclopentyl)-16,17,18,19,20-pentanorprosta-cis-5,trans-13-dienoate By proceeding as described in Reference Example 4 but replacing the methyl 9α-acetoxy-11α-(2-tetrahydropyranyloxy)-15S-hydroxy-15-(trans-4-ethylcyclohexyl)-16,17,18,19,20-pentanorprosta-cis-5,trans-13-dienoate by 1.22 g. of methyl 9α-acetoxy-11α-(2-tetrahydropyranyloxy)-15S-hydroxy-15-(3-propylcyclopentyl)-16,17,18,19,20-pentanorprosta-cis-5,trans-13-dienoate (prepared as described in Reference Example 7) dissolved in 6 ml. of methylene chloride and utilizing 5 mg. of p-toluenesulphonic acid and 0.295 g. of 2,3-dihydropyran, there were obtained 1.48 g. of the title compound having the following physical characteristics:

TLC (developing solvent, benzene-ethyl acetate=2:1): Rf=0.666;

IR (liquid film): $\nu=2950$, 2850, 1740, 1440, 1380, 1250, 1220, 1140, 1090, 1030, 980 cm$^{-1}$.

EXAMPLE 11

Methyl 9α-hydroxy-11α,15S-bis(2-tetrahydropyranyloxy)-15-(3-propylcyclopentyl)-16,17,18,19,20-pentanorprosta-cis-5,trans-13-dienoate By proceeding as described in Example 9 but replacing the methyl 9α-acetoxy-11α-(2-tetrahydropyranyloxy)-15S-hydroxy-15-(3-propylcyclopentyl)-16,17,18,19,20-pentanorprosta-cis-5,trans-13-dienoate by 1.48 g. of methyl 9α-acetoxy-11α,15S-bis(2-tetrahydropyranyloxy)-15-(3-propylcyclopentyl)-16,17,18,19,20-pentanorprosta-cis-5,trans-13-dienoate (prepared as described in Reference Example 8) dissolved in 35 ml. of methanol and utilizing 1.29 g. of anhydrous potassium carbonate, there were obtained 1.277 g. of the title compound having the following physical characteristics:

TLC (developing solvent, benzene-ethyl acetate=2:1): Rf=0.375;

IR (liquid film): $\nu=3450$, 2950, 2850, 1740, 1440, 1380, 1330, 1270, 1210, 1140, 1080, 1020, 980 cm$^{-1}$;

NMR(CDCl$_3$ solution): $\delta=5.70$-5.30 (4H,m), 4.85-4.55 (2H,m), 4.30-3.30 (10H,m), 0.95 (3H,t).

EXAMPLE 12

Methyl 9-oxo-11α,15S-bis(2-tetrahydropyranyloxy)-15-(3-propylcyclopentyl)-16,17,18,19,20-pentanorprosta-cis-5,trans-13-dienoate 0.641 g. of chromium trioxide was added to a solution of 1.03 ml. of dry pyridine in 18 ml. of dry methylene chloride. The mixture was stirred at room temperature for 20 minutes and 1 g. of infusorial earth was added to it. The solution was cooled to 0° C., and to the solution was added a solution of 0.602 g. of methyl 9α-hydroxy-11α,15S-bis(2-tetrahydropyranyloxy)-15-(3-propylcyclopentyl)-16,17,18,19,20-pentanorprosta-cis-5,trans-13-dienoate (prepared as described in Example 11) in 2 ml. of dry methylene chloride. After stirring for an additional 10 minutes at 0° C., 3.6 g. of sodium bisulphate monohydrate were added, and the mixture was stirred for 10 minutes and then filtered through a pad of magnesium sulphate. The filtrate was concentrated under reduced pressure to give 550 mg. of the title compound having the following physical characteristics:

TLC (developing solvent, benzene-ethyl acetate=2:1): Rf=0.625.

EXAMPLE 13

Methyl 9-oxo-11α,15S-dihydroxy-15-(3-propylcyclopentyl)-16,17,18,19,20-pentanorprosta-cis-5,trans-13-dienoate [or 15-(3-propylcyclopentyl)-16,17,18,19,20-pentanor-PGE$_2$ methyl ester]

By proceeding as described in Example 2 but replacing the 9α,15S-dihydroxy-11α-(2-tetrahydropyranyloxy)-15-(trans-4-ethylcyclohexyl)-16,17,18,19,20-pentanorprosta-cis-5,trans-13-dienoic acid by 550 mg. of methyl 9-oxo-11α,15S-bis(2-tetrahydropyranyloxy)-15-(3-propylcyclopentyl)-16,17,18,19,20-pentanorprosta-cis-5,trans-13-dienoate (prepared as described in Example 12) dissolved in a mixture of 1 ml. of tetrahydrofuran and 10 ml. of a 65% aqueous solution of acetic acid, there were obtained 253 mg. of the title compound having the following physical characteristics:

TLC (developing solvent, chloroform-tetrahydrofuran-acetic acid=10:2:1): Rf=0.42;

IR (liquid film): $\nu=3400$, 2950, 2850, 1740, 1440, 1210, 1170, 1080, 980 cm$^{-1}$;

NMR(CDCl$_3$ solution): $\delta=5.67$-5.50 (2H,m), 5.50-5.35 (2H,m), 4.20-3.70 (2H,m), 3.68 (3H,s), 2.75 (1H,dd), 0.95 (3H,t).

EXAMPLE 14

Methyl 9α-hydroxy-11α,15S-bis(2-tetrahydropyranyloxy)-15-(3-propylcyclopentyl)-16,17,18,19,20-pentanorprost-trans-13-enoate By proceeding as described in Example 6 but replacing the 9α-hydroxy-11α,15S-bis(2-tetrahydropyranyloxy)-15-(trans-4-ethylcyclohexyl)-16,17,18,19,20-pentanorprosta-cis-5,trans-13-dienoic acid by 570 mg. of methyl 9α-hydroxy-11α,15S-bis(2-tetrahydropyranyloxy)-15-(3-propylcyclopentyl)-16,17,18,19,20-pentanorprosta-cis-5,trans-13-dienoate (prepared as described in Example 11) dissolved in 10 ml. of methanol and utilizing 200 mg. of 5% palladium on charcoal, there were obtained 386 mg. of the title compound and 127 mg. of methyl 9α-hydroxy-11α,15R-bis(2-tetrahydropyranyloxy)-15-(3-propylcyclopentyl)-16,17,18,19,20-pentanorprostanoate. The title compound showed the following physical characteristics:

TLC (developing solvent, benzene-ethyl acetate=2:1): Rf=0.45;

NMR(CDCl$_3$ solution): $\delta=5.63$-5.25 (2H,m), 4.80-4.55 (2H,m), 4.30-3.10 (10H,m), 0.95 (3H,t).

EXAMPLE 15

Methyl 9-oxo-11α,15S-bis(2-tetrahydropyranyloxy)-15-(3-propylcyclopentyl)-16,17,18,19,20-pentanorprost-trans-13-enoate By proceeding as described in Example 12 but replacing the methyl 9α-hydroxy-11α,15S-bis(2-tetrahydropyranyloxy)-15-(3-propylcyclopentyl)-16,17,18,19,20-pentanorprosta-cis-5,trans-13-dienoate by 0.106 g. of methyl 9α-hydroxy-11α,15S-bis(2-tetrahydropyranyloxy)-15-(3-propylcyclopentyl)-16,17,18,19,20-pentanorprost-trans-13-enoate (prepared as described in Example 14) dissolved in 0.5 ml. of dry methylene chloride and utilizing 0.112 g. of chromium trioxide, a suspension of 0.182 ml. of dry pyridine in 3 ml. of dry methylene chloride, 0.5 g. of infusorial earth and 0.65 g. of sodium bisulphate monohydrate, there were obtained 0.105 g. of the title compound having the following physical characteristic:

TLC (developing solvent, benzene-ethyl acetate=2:1): Rf=0.679.

EXAMPLE 16

Methyl 9-oxo-11α,15S-dihydroxy-15-(3-propylcyclopentyl)-16,17,18,19,20-pentanorprost-trans-13-enoate [or 15-(3-propylcyclopentyl)-16,17,18,19,20-pentanor-PGE$_1$ methyl ester]

By proceeding as described in Example 2 but replacing the 9α,15S-dihydroxy-11α-(2-tetrahydropyranyloxy)-15-(trans-4-ethylcyclohexyl)-16,17,18,19,20-pentanorprosta-cis-5,trans-13-dienoic acid by 105 mg. of methyl 9-oxo-11α,15S-bis(2-tetrahydropyranyloxy)-15-(3-propylcyclopentyl)-16,17,18,19,20-pentanorprost-trans-13-enoate (prepared as described in Example 15) dissolved in a mixture of 0.3 ml. of tetrahydrofuran and 3 ml. of a 65% aqueous solution of acetic acid, there were obtained 43 mg. of the title compound having the following physical characteristics:

TLC (developing solvent, ethyl acetate-benzene=3:1): Rf=0.34;
IR(KBr tablet): ν=3350, 2950, 2850, 1740, 1470, 1430, 1360, 1310, 1270, 1210, 1170, 1090, 980 cm$^{-1}$;
NMR(CDCl$_3$ solution): δ=5.70-5.55 (2H,m), 4.13-3.74 (2H,m), 3.67 (3H,s), 2.93-2.61 (1H,dd), 0.95 (3H,t).

EXAMPLE 17

9α,11α,15S-Trihydroxy-15-(3-propylcyclopentyl)-16,17,18,19,20-pentanorprosta-cis-5,trans-13-dienoic acid [or 15-(3-propylcyclopentyl)-16,17,18,19,20-pentanor-PGF$_{2\alpha}$]

To a solution of 140 mg. of methyl 9α,11α,15S-trihydroxy-15-(3-propylcyclopentyl)-16,17,18,19,20-pentanorprosta-cis-5,trans-13-dienoate (prepared as described in Example 10) in 2 ml. of ethanol there were added 3 ml. of a 2 N aqueous solution of potassium hydroxide, and the mixture was stirred at 40° to 45° C. for 2 hours. The reaction mixture was then acidified with acetic acid and concentrated under reduced pressure. The residue was dissolved with ethyl acetate, washed with an aqueous solution of sodium chloride, dried over magnesium sulphate and concentrated under reduced pressure. The residue was purified by column chromatography on silica gel using a mixture of cyclohexane and ethyl acetate (1:1) as eluent to give 71 mg. of the title compound having the following physical characteristics:

TLC (developing solvent, chloroform-tetrahydrofuran-acetic acid=10:2:1): Rf=0.10;
IR (liquid film): ν=3450, 2925, 1700, 1240, 1045, 970 cm$^{-1}$;
NMR(CDCl$_3$ solution): δ=5.7-5.2 (4H,m), 5.2-4.0 (5H, broad s), 4.3-3.6 (3H,m), 2.7-0.7 (27H,m).

EXAMPLE 18

9α-Hydroxy-11α,15S-bis(2-tetrahydropyranyloxy)-15-(3-propylcyclopentyl)-16,17,18,19,20-pentanorprost-trans-13-enoic acid By proceeding as described in Example 17 but replacing the methyl 9α,11α,15S-trihydroxy-15-(3-propylcyclopentyl)-16,17,18,19,20-pentanorprosta-cis-5,trans-13-dienoate by 0.113 g. of methyl 9α-hydroxy-11α,15S-bis(2-tetrahydropyranyloxy)-15-(3-propylcyclopentyl)-16,17,18,19,20-pentanorprost-trans-13-enoate (prepared as described in Example 14) dissolved in 3.0 ml. of methanol and utilizing 2.0 ml. of a 2 N aqueous solution of potassium hydroxide, there were obtained 0.110 g. of the title compound having the following physical characteristic:

TLC (developing solvent, methylene chloride-methanol=20:1): Rf=0.33.

EXAMPLE 19

9-Oxo-11α,15S-bis(2-tetrahydropyranyloxy)-15-(3-propylcyclopentyl)-16,17,18,19,20-pentanorprost-trans-13-enoic acid By proceeding as described in Example 4 but replacing the 9α-hydroxy-11α,15S-bis(2-tetrahydropyranyloxy)-15-(trans-4-ethylcyclohexyl)-16,17,18,19,20-pentanorprosta-cis-5,trans-13-dienoic acid by 0.110 g. of 9α-hydroxy-11α,15S-bis(2-tetrahydropyranyloxy)-15-(3-propylcyclopentyl)-16,17,18,19,20-pentanorprost-trans-13-enoic acid (prepared as described in Example 18) dissolved in 4 ml. of diethyl ether and utilizing 4 ml. of the chromic acid solution, there were obtained 0.104 g. of the title compound having the following physical characteristics:

TLC (developing solvent, methylene chloride-methanol=20:1): Rf=0.35.

EXAMPLE 20

9-Oxo-11α,15S-dihydroxy-15-(3-propylcyclopentyl)-16,17,18,19,20-pentanorprost-trans-13-enoic acid [or 15-(3-propylcyclopentyl)-16,17,18,19,20-pentanor-PGE$_1$]

By proceeding as described in Example 2 but replacing the 9α,15S-dihydroxy-11α-(2-tetrahydropyranyloxy)-15-(trans-4-ethylcyclohexyl)-16,17,18,19,20-pentanorprosta-cis-5,trans-13-dienoic acid by 0.104 g. of 9-oxo-11α,15S-bis(2-tetrahydropyranyloxy)-15-(3-propylcyclopentyl)-16,17,18,19,20-pentanorprost-trans-13-enoic acid (prepared as described in Example 19) dissolved in a mixture of 0.5 ml. of tetrahydrofuran and 5 ml. of a 65% aqueous solution of acetic acid, there were obtained 69 mg. of the title compound having the following characteristics:

TLC (developing solvent, chloroform-tetrahydrofuran-acetic acid=10:2:1): Rf=0.235;
NMR(CDCl$_3$ solution): δ=5.70-5.10 (5H,m), 4.21-3.72 (2H,m), 2.85-2.60 (1H,dd), 0.90 (3H,t).

REFERENCE EXAMPLE 9

1-Methoxycarbonyl-1-methyl-3-propylcyclopentane

Under an atmosphere of nitrogen, 3 ml. of a 1.4 M solution of n-butyllithium in n-hexane were added to a solution of 0.643 ml. of diisopropylamine in 3 ml. of dry tetrahydrofuran at −78° C. and the solution was stirred at that temperature for 15 minutes. To the lithium diisopropylamide solution thus obtained was added dropwise a solution of 300 mg. of 1-methoxycarbonyl-3-propylcyclopentane in 5 ml. of dry tetrahydrofuran and the mixture was stirred at −78° C. for 30 minutes. To the solution was added a solution of 0.216 ml. of methyl iodide in 5 ml. of dry tetrahydrofuran and the mixture was stirred at −78° C. for one hour. The reaction mixture was quenched with an aqueous solution of ammonium chloride and extracted with diethyl ether. The extract was washed with 1 N hydrochloric acid, an aqueous solution of sodium bicarbonate, water and an aqueous solution of sodium chloride, dried over magnesium sulphate and concentrated under reduced pressure to give 330 mg. of the title compound having the following physical characteristic:
NMR(CDCl$_3$ solution): $\delta$=3.7 (3H,s), 2.7-1.1 (14H,m), 1.1-0.6 (3H,m).

REFERENCE EXAMPLE 10

Dimethyl 2-oxo-2-(1-methyl-3-propylcyclopentyl)ethylphosphonate

By proceeding as described in Reference Example 5 but replacing the 1-methoxycarbonyl-3-propylcyclopentane by 4.5 g. of 1-methoxycarbonyl-1-methyl-3-propylcyclopentane (prepared as described in Reference Example 9) dissolved in 30 ml. of dry tetrahydrofuran and utilizing a solution of 5.5 g. of dimethyl methylphosphonate in 40 ml. of dry tetrahydrofuran and 31.5 ml. of a 14 M solution of n-butyllithium in n-hexane, there were obtained 5.0 g. of the title compound having the following physical characteristics:
TLC (developing solvent, ethyl acetate): Rf=0.58;
NMR(CDCl$_3$ solution): $\delta$=3.85 (6H,d), 3.2 (2H,d), 2.7-1.1 (14H,m), 1.1-0.65 (3H,m).

REFERENCE EXAMPLE 11

Methyl 9α-acetoxy-11α-(2-tetrahydropyranyloxy)-15-oxo-15-(1-methyl-3-propylcyclopentyl)-16,17,18,19,20-pentanorprosta-cis-5,trans-13-dienoate By proceeding as described in Reference Example 2 but replacing the dimethyl 2-oxo-2-(trans-4-ethylcyclohexyl)ethylphosphonate by 5.0 g. of dimethyl 2-oxo-2-(1-methyl-3-propylcyclopentyl)ethylphosphonate (prepared as described in Reference Example 10) dissolved in 20 ml of dry tetrahydrofuran and utilizing a suspension of 689 mg. of sodium hydride (63% content) in 80 ml. of dry tetrahydrofuran and 5.8 g. of 1α-acetoxy-2α-(6-methoxycarbonylhex-cis-2-enyl)-3β-formyl-4α-(2-tetrahydropyranyloxy)cyclopentane in 35 ml. of dry tetrahydrofuran, there were added 7.2 g. of the title compound having the following physical characteristics:
TLC (developing solvent, benzene-ethyl acetate=4:1): Rf=0.65;
IR (liquid film): $\nu$=2950, 2870, 1740, 1695, 1630 cm$^{-1}$;
NMR (CDCl$_3$ solution): $\delta$=7.2-6.2 (2H,m), 5.7-4.8 (3H,m), 4.8-4.4 (1H,m).

REFERENCE EXAMPLE 12

Methyl 9α-acetoxy-11α-(2-tetrahydropyranyloxy)-15R-hydroxy-15-(1-methyl-3-propylcyclopentyl)-16,17,18,19,20-pentanorprosta-cis-5,trans-13-dienoate By proceeding as described in Reference Example 8 but replacing the methyl 9α-acetoxy-11α-(2-tetrahydropyranyloxy)-15-oxo-15-(trans-4-ethylcyclohexyl)-16,17,18,19,20-pentanorprosta-cis-5,trans-13-dienoate by 7.2 g. of methyl 9α-acetoxy-11α-(2-tetrahydropyranyloxy)-15-oxo-15-(1-methyl-3-propylcyclopentyl)-16,17,18,19,20-pentanorprosta-cis-5,trans-13-dienoate (prepared as described in Reference Example 11) dissolved in 70 ml. of methanol and utilizing 1.5 g of sodium borohydride; there were obtained 2.85 g. of the title compound, 1.617 g. of its 15S-hydroxy isomer and 1.47 g. of their mixture. The title compound showed the following physical characteristics:
TLC (developing solvent, benzene-ethyl acetate=1:2): Rf=0.53, (15S-hydroxy isomer, Rf=0.70);
IR (liquid film): $\nu$=3500, 2950, 2870, 1740, 980 cm$^{-1}$;
NMR (CDCl$_3$ solution): $\delta$=5.90-5.57 (2H,m), 5.57-5.30 (2H,m), 5.30-5.00 (1H,m), 4.9-4.5 (1H,m), 3.7 (3H,s), 4.4-3.1 (4H,m).

EXAMPLE 21

Methyl 9α,15R-dihydroxy-11α-(2-tetrahydropyranyloxy)-15-(1-methyl-3-propylcyclopentyl)-16,17,18,19,20-pentanorprosta-cis-5,trans-13-dienoate By proceeding as described in Example 9 but replacing the methyl 9α-acetoxy-11α-(2-tetrahydropyranyloxy)-15S-hydroxy-15-(3-propylcyclopentyl)-16,17,18,19,20-pentanorprosta-cis-5,trans-13-dienoate by 300 mg. of methyl 9α-acetoxy-11α-(2-tetrahydropyranyloxy)-15R-hydroxy-15-(1-methyl-3-propylcyclopentyl)-16,17,18,19,20-pentanorprosta-cis-5,trans-13-dienoate (prepared as described in Reference Example 12) dissolved in 2.6 ml. of methanol and utilizing 93 mg. of anhydrous potassium carbonate, there were obtained 276 mg. of the title compound having the following physical characteristics:
TLC (developing solvent, benzene-ethyl acetate=2:1): Rf=0.36;
IR (liquid film): $\nu$=3450, 2950, 2860, 1730, 980 cm$^{-1}$;
NMR (CDCl$_3$ solution): $\delta$=5.9-5.3 (4H,m), 4.9-4.5 (1H,m), 3.7 (3H,s), 4.4-3.1 (5H,m), 1.1-0.6 (6H,m).

EXAMPLE 22

Methyl 9α,11α,15R-trihydroxy-15-(1-methyl-3-propylcyclopentyl)-16,17,18,19,20-pentanorprosta-cis-5,trans-13-dienoate [or 15-(1-methyl-3-propylcyclopentyl)-16,17,18,19,20-pentanor-PGF$_{2\alpha}$ methyl ester]

A solution of 276 mg. of methyl 9α,15R-dihydroxy-11α-(2-tetrahydropyranyloxy)-15-(1-methyl-3-propylcyclopentyl)-16,17,18,19,20-pentanorprosta-cis-5,trans-13-dienoate (prepared as described in Example 21) in a mixture of 9 ml. of tetrahydrofuran and 4 ml. of 1 N hydrochloric acid was stirred at 40° to 50° C. for one hour, and the reaction mixture was then concentrated under reduced pressure. The residue was dissolved in ethyl acetate, washed with water and an aqueous solution of sodium chloride, dried over magnesium sulphate and concentrated under reduced pressure. The residue was purified by column chromatography on silica gel using a mixture of benzene and ethyl acetate (3:2) as eluent to give 128 mg. of the title compound having the following physical characteristics:

TLC (developing solvent, chloroform-tetrahydrofuran-acetic acid = 10:2:1): Rf=0.38;
IR (liquid film): ν=3400, 2950, 2880, 1740, 980 cm$^{-1}$;
NMR (CDCl$_3$ solution): δ=5.75-5.15 (4H,m), 4.30-4.05 (1H,m), 3.67 (3H,s), 4.05-3.53 (4H,m), 1.05-0.7 (6H,m).

REFERENCE EXAMPLE 13

Methyl 9α acetoxy-11α,15R-bis(2-tetrahydropyranyloxy)-15-(1-methyl-3-propylcyclopentyl)-16,17,18,19,20-pentanor-prosta-cis-5,trans-13-dienoate By proceeding as described in Reference Example 4 but replacing methyl 9α-acetoxy-11α-(2-tetrahydropyranyloxy)-15S-hydroxy-15-(trans-4-ethylcyclohexyl)-16,17,18,19,20-pentanorprosta-cis-5,trans-13-dienoate by 1.48 g. of methyl 9α-acetoxy-11α-(2-tetrahydropyranyloxy)-15R-hydroxy-15-(1-methyl-3-propylcyclopentyl)-16,17,18,19,20-pentanorprosta-cis-5,-trans-13-dienoate (prepared as described in Reference Example 12) dissolved in 16.5 ml. of methylene chloride and utilizing 9.8 mg of p-toluene-sulphonic acid and 0.765 ml. of 2,3-dihydropyran, there were obtained 1.27 g. of the title compound having the following physical characteristics:

TLC (developing solvent, benzene-ethyl acetate=2:1): Rf=0.82;
IR (liquid film): ν=2950, 2860, 1740, 1440, 1380, 980 cm$^{-1}$;
NMR (CDCl$_3$ solution): δ=5.7-5.2 (4H,m), 5.2-4.9 (1H,m), 4.8-4.4 (2H,m), 3.65 (3H,s), 4.3-3.1 (6H,m).

EXAMPLE 23

Methyl 9α-hydroxy-11α,15R-bis(2-tetrahydropyranyloxy)-15-(1-methyl-3-propylcyclopentyl)-16,17,18,19,20-pentanor-prosta-cis-5,trans-13-dienoate By proceeding as described in Example 9 but replacing the methyl 9α-acetoxy-11α-(2-tetrahydropyranyloxy)-15S-hydroxy-15-(3-propylcyclopentyl)-16,17,18,19,20-pentanorprosta-cis-5,trans-13-dienoate by 1.27 g. of methyl 9α-acetoxy-11α,15R-bis(2-tetrahydropyranyloxy)-15-(1-methyl-3-propylcyclopentyl)-16,17,18,19,20-pentanorprosta-cis-5,trans-13-dienoate (prepared as described in Reference Example 13) dissolved in 12 ml. of methanol and utilizing 430 mg. of anhydrous potassium carbonate, there were obtained 1.2 g. of the title compound having the following physical characteristics:

TLC (developing solvent, benzene-ethyl acetate=2:1): Rf=0.64;
IR (liquid film): ν=3500, 2950, 2870, 1740, 980 cm$^{-1}$;
NMR (CDCl$_3$ solution): δ=5.8-5.2 (4H,m), 4.8-4.4 (2H,m), 3.65 (3H,s), 4.3-3.1 (8H,m).

EXAMPLE 24

Methyl 9-oxo-11α,15R-bis(2-tetrahydropyranyloxy)-15-(1-methyl-3-propylcyclopentyl)-16,17,18,19,20-pentanor-prosta-cis-5,trans-13-dienoate By proceeding as described in Example 4 but replacing the 9α-hydroxy-11α,15S-bis(2-tetrahydropyranyloxy)-15-(trans-4-ethylcyclohexyl)-16,17,18,19,20-pentanorprosta-cis-5,trans-13-dienoic acid by 400 mg. of methyl 9α-hydroxy-11α15R-bis(2-tetrahydropyranyloxy)-15-(1-methyl-3-propylcyclopentyl)-16,17,18,19,20-pentanorprosta-cis-5,trans-13-dienoate (prepared as described in Example 23) dissolved in 20 ml. of diethyl ether and utilizing 5.2 ml of the chromic acid solution, there were obtained 276 mg. of the title compound having the following physical characteristics:

TLC (developing solvent, benzene-ethyl acetate=2:1): Rf=0.79;
IR (liquid film): ν=2950, 2860, 1740, 980 cm$^{-1}$;
NMR (CDCl$_3$ solution): δ=5.9-5.1 (4H,m), 4.9-4.4 (2H,m), 3.65 (3H,s), 4.4-3.1 (6H,m).

EXAMPLE 25

Methyl 9-oxo-11α,15R-dihydroxy-15-(1-methyl-3-propylcyclopentyl)-16,17,18,19,20-pentanorprosta-cis-5,trans-13-dienoate [or 15-(1-methyl-3-propylcyclopentyl)-16,17,18,19,20-pentanor-PGE$_2$ methyl ester]

By proceeding as described in Example 2 but replacing the 9α,15S-dihydroxy-11α-(2-tetrahydropyranyloxy)-15-(trans-4-ethylcyclohexyl)-16,17,18,19,20-pentanor-prosta-cis-5,trans-13-dienoic acid by 276 mg. of methyl 9-oxo-11α,15R-bis(2-tetrahydropyranyloxy)-15-(1-methyl-3-propylcyclopentyl)-16,17,18,19,20-pentanorprosta-cis-5,trans-13-dienoate (prepared as described in Example 24) dissolved in a mixture of 0.86 ml. of tetrahydrofuran and 3.66 ml. of a 65% aqueous solution of acetic acid there were obtained 76 mg. of the title compound having the following physical characteristics:

TLC (developing solvent, chloroform-tetrahydrofuranacetic acid = 10:2:1): Rf=0.21;
IR (liquid film): ν=3400, 2950, 2860, 1740, 980 cm$^{-1}$;
NMR (CDCl$_3$ solution): δ=5.9-5.5 (2H,m), 5.5-5.2 (2H,m), 3.65 (3H,s), 4.3-3.2 (3H,m), 2.75 (1H,dd), 1.05-0.7 (6H,m).

EXAMPLE 26

Methyl 9α-hydroxy-11α,15R-bis(2-tetrahydropyranyloxy)-15-(1-methyl-3-propylcyclopentyl)-16,17,18,19,20-pentanorprost-trans-13-enoate By proceeding as described in Example 6 but replacing the 9α-hydroxy-11α,15S-bis(2-tetrahydropyranyloxy)-15-(trans-4-enthylcyclohexyl)-16,17,18,19,20-pentanorprosta-cis-5,trans-13-dienoic acid by 800 mg. of methyl 9α-hydroxy-11α,15R-bis(2-tetrahydropyranyloxy)-15-(1-methyl-3-propylcyclopentyl)-16,17,18,19,20-pentanorprosta-cis-5-trans-13-dienoate (prepared as described in Example 23) dissolved in 11 ml. of methanol and utilizing 260 mg. of 5% palladium on charcoal, there were obtained 770 mg. of the title compound having the following physical characteristics:
IR (liquid film): $\nu=3480, 2950, 2860, 1740, 980$ cm$^{-1}$;
NMR (CDCl$_3$ solution): $\delta=5.7-5.2$ (2H,m), 4.9-4.3 (2H,m), 3.65 (3H,s).

EXAMPLE 27

Methyl 9-oxo-11α,15R-bis(2-tetrahydropyranyloxy)-15-(1-methyl-3-propylcyclopentyl)-16,17,18,19,20-pentanor-prost-trans-13-enoate By proceeding as described in Example 4 but replacing the 9α-hydroxy-11α,15S-bis(2-tetrahydropyranyloxy)-15-(trans-4-ethylcyclohexyl)-16,17,18,19,20-pentanorprosta-cis-5,trans-13-dienoic acid by 770 mg. of methyl 9α-hydroxy-11α,15R-bis(2-tetrahydropyranyloxy)-15-(1-methyl-3-propylcyclopentyl)-16,17,18,19,20-pentanorprost-trans-13-enoate (prepared as described in Example 26) dissolved in 40 ml. of diethyl ether and utilizing 9.96 ml. of the chromic acid solution, there were obtained 500 mg. of the title compound having the following physical characteristics:
TLC (developing solvent, benzene-ethyl acetate=2:1): Rf=0.82;
IR (liquid film): $\nu=2950, 2860, 1745, 980$ cm$^{-1}$;
NMR (CDCl$_3$ solution): $\delta=5.7-5.2$ (2H,m), 4.9-4.3 (2H,m), 3.65 (3H,s), 4.4-3.0 (6H,m), 2.75 (1H,dd).

EXAMPLE 28

Methyl 9-oxo-11α,15R-dihydroxy-15-(1-methyl-3-propylcyclopentyl)-16,17,18,19,20-pentanorprost-trans-13-enoate [or 15-(1-methyl-3-propylcyclopentyl)-16,17,18,19,20-pentanor-PGE$_1$ methyl ester]

By proceeding as described in Example 2 but replacing the 9α,15S-dihydroxy-11α-(2-tetrahydropyranyloxy)-15-(trans-4-ethylcyclohexyl)-16,17,18,19,20-pentanorprosta-cis-5,trans-13-dienoic acid by 500 mg. of methyl 9-oxo-11α,15R-bis(2-tetrahydropyranyloxy)-15-(1-methyl-3-propylcyclopentyl)-16,17,18,19,20-pentanor-prost-trans-13-enoate (prepared as described in Example 27) dissolved in a mixture of 1.7 ml. of tetrahydrofuran and 6.6 ml. of a 65% aqueous solution of acetic acid, there were obtained 131 mg. of the title compound having the following physical characteristics:
TLC (developing solvent, chloroform-tetrahydrofuranacetic acid=10:2:1): Rf=0.20;
IR (liquid film): $\nu=3400, 2950, 2850, 1740, 980$ cm$^{-1}$;
NMR (CDCl$_3$ solution): $\delta=5.90-5.50$ (2H,m), 4.15-3.75 (2H,m), 3.65 (3H,s), 2.75 (1H,dd).

REFERENCE EXAMPLE 14

Dimethyl 2-oxo-2-(3-phenylcyclopentyl)ethylphosphonate

By proceeding as described in Reference Example 5 but replacing the 1-methoxycarbonyl-3-propylcyclopentane by 5.23 g. of 1-methoxycarbonyl-3-phenylcyclopentane dissolved in 10 ml. of dry tetrahydrofuran and utilizing a solution of 7.95 g. of dimethyl methylphosphonate in 100 ml. of dry tetrahydrofuran and 64.1 ml. of a 1.0 N solution of n-butyllithium in n-hexane, there were obtained 5.74 g. of the title compound having the following physical characteristics:
NMR (CDCl$_3$ solution): $\delta=7.30$ (5H,s), 3.85 (6H,d), 3.20 (2H,d), 3.50-2.80 (2H,m), 2.70-1.50 (6H,m).

REFERENCE EXAMPLE 15

Methyl 9α-acetoxy-11α-(2-tetrahydropyranyloxy)-15-oxo-15-(3-phenylcyclopentyl)-16,17,18,19,20-pentanorprosta-cis-5,trans-13-dienoate By proceeding as described in Reference Example 2 but replacing the dimethyl 2-oxo-2-(trans-4-ethylcyclohexyl)ethylphosphonate by 5.74 g. of dimethyl 2-oxo-2-(3-phenylcyclopentyl)ethylphosphonate (prepared as described in Reference Example 14) dissolved in 10 ml. of dry tetrahyfrofuran and utilizing a suspension of 0.739 g. of sodium hydride (63% content) in 80 ml. of dry tetrahydrofuran and 6.38 g. of 1α-acetoxy-2α-(6-methoxycarbonylhex-cis-2-enyl)-3β-formyl-4α-(2-tetrahydropyranyloxy)cyclopentane in 20 ml. of dry tetrahydrofuran, there were obtained 8.11 g. of the title compound having the following physical characteristics:
TLC (developing solvent, benzene-ethyl acetate=3:1): Rf=0.67;
IR (liquid film): $\nu=3030, 2950, 2850, 1740, 1690, 1660, 1630, 1430, 1370, 1240, 1030, 790, 760$ cm$^{-1}$;
NMR (CDCl$_3$ solution): $\delta=7.41$ (5H,s), 7.09-6.63 (1H,dd), 6.55-6.12 (1H,d), 5.62-5.30 (2H,m), 5.30-5.00 (1H,m), 4.60 (1H,broad s), 3.65 (3H,s), 2.05 (3H,s).

REFERENCE EXAMPLE 16

Methyl 9α-acetoxy-11α-(2-tetrahydropyranyloxy)-15S-hydroxy-15-(3-phenylcyclopentyl)-16,17,18,19,20-pentanorprosta-cis-5,trans-13-dienoate By proceeding as described in Reference Example 3 but replacing the methyl 9α-acetoxy-11α-(2-tetrahydropyranyloxy)-15-oxo-15-(trans-4-ethylcyclohexyl)-16,17,18,19,20-pentanorprosta-cis-5,trans-13-dienoate by 8.11 g. of methyl 9α-acetoxy-11α-(2-tetrahydropyranyloxy)-15-oxo-15-(3-phenylcyclopentyl)-16,17,18,19,20-pentanorprosta-cis-5,trans-13-dienoate (prepared as described in Reference Example 15) dissolved in 100 ml. of methanol and utilizing 1.09 g. of sodium borohydride, there were obtained 3.97 g. of the title compound, 2.06 g. of its 15R-hydroxy isomer and 1.37 g. of their mixture. The title compound showed the following physical characteristics:
TLC (developing solvent, benzene-ethyl acetate=3:1): Rf=0.38, (15R-hydroxy isomer, Rf=0.40);
IR (liquid film): $\nu=3450, 3030, 2950, 2850, 1740, 1600, 1430, 1370, 1245, 1140, 1030, 980, 760, 700$ cm$^{-1}$;
NMR (CDCl$_3$ solution ): $\delta=7.25$ (5H,s), 5.78-5.50 (2H,m), 5.50-5.20 (2H,m), 5.20-4.70 (1H,m), 4.65-4.51 (1H,m), 4.20-3.00 (7H,m), 2.05 (3H,s).

EXAMPLE 29

Methyl 9α,15S-dihydroxy-11α-(2-tetrahydropyranyloxy)-15-(3-phenylcyclopentyl)-16,17,18,19,20-pentanorprosta-cis-5,trans-13-dienoate By proceeding as described in Example 9 but replacing the methyl 9α-acetoxy-11α-(2-tetrahydropyranyloxy)-15S-hydroxy-15-(3-propylcyclopentyl)-16,17,18,19,20-pentanorprosta-cis-5,trans-13-dienoate by 0.995 g. of methyl 9α-acetoxy-11α-(2-tetrahydropyranyloxy)-15S-hydroxy-15-(3-phenylcyclopentyl)-16,17,18,19,20-pentanorprosta-cis-5,trans-13-dienoate (prepared as described in Reference Example 16) dissolved in 30 ml. of methanol and utilizing 0.96 g. of anhydrous potassium carbonate, there were obtained 0.991 g. of the title compound having the following physical characteristics:

TLC (developing solvent, benzene-ethyl acetate=2:1): Rf=0.22;
IR (liquid film): $\nu$=3450, 3030, 2950, 2850, 1740, 1600, 1490, 1440, 1350, 1220, 1140, 1080, 1010, 980, 750, 700 cm$^{-1}$;
NMR (CDCl$_3$ solution): $\delta$=7.30 (5H,s), 5.85–5.25 (4H,m), 4.85–4.55 (1H,m), 4.37–3.00 (8H,m).

EXAMPLE 30

Methyl 9$\alpha$,11$\alpha$,15S-trihydroxy-15-(3-phenylcyclopentyl)-16,17,18,19,20-pentanorprosta-cis-5,trans-13-dienoate [or 15-(3-phenylcyclopentyl)-16,17,18,19,20-pentanor-PGF$_2\alpha$ methyl ester]

By proceeding as described in Example 2 but replacing the 9$\alpha$,15S-dihydroxy-11$\alpha$-(2-tetrahydropyranyloxy)-15-(trans-4-ethylcyclohexyl)-16,17,18,19,20-pentanorprosta-cis-5,trans-13-dienoic acid by 0.991 g. of methyl 9$\alpha$,15S-dihydroxy-11$\alpha$-(2-tetrahydropyranyloxy)-15-(3-phenylcyclopentyl)-16,17,18,19,20-pentanorprosta-cis-5,trans-13-dienoate (prepared as described in Example 29) dissolved in a mixture of 3 ml. of tetrahydrofuran and 30 ml. of a 65% aqueous solution of acetic acid, there were obtained 159 mg. of the title compound having the following physical characteristics:

TLC (developing solvent, ethyl acetate): Rf=0.30;
IR (liquid film): $\nu$=3400, 3030, 2950, 2850, 1740, 1600, 1490, 1430, 1240, 1170, 1030, 980, 750, 700 cm$^{-1}$;
NMR (CDCl$_3$ solution): $\delta$=7.23 (5H,s), 5.71–5.09 (4H,m), 4.23–4.05 (1H,m), 4.05–3.70 (2H,m), 3.65 (3H,s), 3.30–3.00 (3H, broad s).

REFERENCE EXAMPLE 17

Methyl 9$\alpha$-acetoxy-11$\alpha$,15S-bis(2-tetrahydropyranyloxy)-15-(3-phenylcyclopentyl)-16,17,18,19,20-pentanorprosta-cis-5,trans-13-dienoate By proceeding as described in Reference Example 4 but replacing the methyl 9$\alpha$-acetoxy-11$\alpha$-(2-tetrahydropyranyloxy)-15S-hydroxy-15-(trans-4-ethylcyclohexyl)-16,17,18,19,20-pentanorprosta-cis-5,trans-13-dienoate by 1.03 g. of methyl 9$\alpha$-acetoxy-11$\alpha$-(2-tetrahydropyranyloxy)-15S-hydroxy-15-(3-phenylcyclopentyl)-16,17,18,19,20-pentanorprosta-cis-5,trans-13-dienoate (prepared as described in Reference Example 16) dissolved in 6 ml. of methylene chloride and utilizing 5 mg. of p-toluenesulphonic acid and 0.305 g. of 2,3-dihydropyran, there were obtained 1.31 g. of the title compound having the following physical characteristics:

TLC (developing solvent, benzene-ethyl acetate=4:1): Rf=0.52;
NMR (CDCl$_3$ solution): $\delta$=7.20 (5H,s), 5.72–5.20 (4H,m), 5.20–4.70 (1H,m), 4.70–4.20 (2H,m), 3.65 (3H,s), 2.00 (3H,s).

EXAMPLE 31

Methyl 9$\alpha$-hydroxy-11$\alpha$,15S-bis(2-tetrahydropyranyloxy)-15-(3-phenylcyclopentyl)-16,17,18,19,20-pentanorprosta-cis-5,trans-13-dienoate By proceeding as described in Example 9 but replacing the methyl 9$\alpha$-acetoxy-11$\alpha$-(2-tetrahydropyranyloxy)-15S-hydroxy-15-(3-propylcyclopentyl)-16,17,18,19,20-pentanorprosta-cis-5,trans-13-dienoate by 1.31 g. of methyl 9$\alpha$-acetoxy-11$\alpha$,15S-bis(2-tetrahydropyranyloxy)-15-(3-phenylcyclopentyl)-16,17,18,19,20-pentanorprosta-cis-5,trans-13-dienoate (prepared as described in Reference Example 17) dissolved in 27 ml of methanol and utilizing 0.999 g. of anhydrous potassium carbonate, there were obtained 1.16 g. of the title compound having the following physical characteristics:

TLC (developing solvent, benzene-ethyl acetate=4:1): Rf=0.24;
NMR (CDCl$_3$ solution): $\delta$=7.23 (5H,s), 5.72–5.25 (4H,m), 4.85–4.40 (2H,m), 3.62 (3H,s).

EXAMPLE 32

Methyl 9-oxo-11$\alpha$,15S-bis(2-tetrahydropyranyloxy)-15-(3-phenylcyclopentyl)-16,17,18,19,20-pentanorprosta-cis-5,trans-13-dienoate By proceeding as described in Example 12 but replacing the methyl 9$\alpha$-hydroxy-11$\alpha$,15S-bis(2-tetrahydropyranyloxy)-15-(3-propylcyclopentyl)-16,17,18,19,20-pentanorprosta-cis-5,trans-13-dienoate by 1.16 g. of methyl 9$\alpha$-hydroxy-11$\alpha$,15S-bis(2-tetrahydropyranyloxy)-15-(3-phenylcyclopentyl)-16,17,18,19,20-pentanorprostacis-5,trans-13-dienoate (prepared as described in Example 31) dissolved in 5 ml. of dry methylene chloride and utilizing a solution of 3.05 ml. of pyridine in 50 ml. of dry methylene chloride, 1.89 g. of chromium trioxide, 3 g. of infusorial earth and 12 g. of sodium bisulphate, there were obtained 1.12 g. of the title compound having the following physical characteristics:

TLC (developing solvent, benzene-ethyl acetate=4:1): Rf=0.44.

EXAMPLE 33

Methyl 9-oxo-11$\alpha$,15S-dihydroxy-15-(3-phenylcyclopentyl)16,17,18,19,20-pentanorprosta-cis-5,trans-13-dienoate [or 15-(3-phenylcyclopentyl)-16,17,18,19,20-pentanor-PGE$_2$ methyl ester]

By proceeding as described in Example 2 but replacing the 9$\alpha$,15S-dihydroxy-11$\alpha$-(2-tetrahydropyranyloxy)-15-(trans-4-ethylcyclohexyl)-16,17,18,19,20-pentanorprosta-cis-5,trans-13dienoic acid by 1.12 g. of methyl 9-oxo-11$\alpha$,15S-bis(2-tetrahydropyranyloxy)-15-(3-phenylcyclopentyl)-16,17,18,19,20-pentanorprosta-cis-5,trans-13-dienoate (prepared as described in Example 32) dissolved in a mixture of 5 ml. of tetrahydrofuran and 40 ml. of a 65% suspension of acetic acid, there were obtained 364 mg. of the title compound having the following physical characteristics:

TLC (developing solvent ethyl acetate-benzene=3:1): Rf=0.39;

IR (liquid film): $\nu = 3400$, 3030, 2950, 2850, 1740, 1600, 1490, 1430, 1370, 1320, 1250, 1160, 1080, 1040, 980, 750, 700 cm$^{-1}$;

NMR (CDCl$_3$ solution): $\delta = 7.25$ (5H,s), 5.72–5.48 (2H,m), 5.48–5.10 (2H,m), 4.15–3.75 (2H,m), 3.65 (3H,s), 3.30–2.50 (2H, broad s), 2.75 (1H,dd).

REFERENCE EXAMPLE 18

Methyl 9α-acetoxy-11α-(2-tetrahydropyranyloxy)-15S-hydroxy-15-(3-ethylcyclohexyl)-16,17,18,19,20-pentanorprosta-cis-5,trans-13-dienoate Under an atmosphere of argon, a trace amount of methyl iodide was added to a mixture of 220 mg. of magnesium and 0.5 ml. of dry tetrahydrofuran at room temperature, and to the mixture was added dropwise a solution of 1.588 g. of 1-bromo-3-ethylcyclohexane in 6.5 ml. of dry tetrahydrofuran. The mixture was refluxed with stirring for 2.5 hours. The Grignard reagent solution thus obtained was added dropwise to a solution of 2.0 g. of 1α-acetoxy-2α-(6-methoxycarbonylhex-cis-2-enyl)-3β-(2-formyl-trans-vinyl)-4α-(2-tetrahydropyranyloxy)-cyclopentane in 32 ml. of dry tetrahydrofuran at 0° to 5° C. and the mixture was stirred at that temperature for one hour. The reaction mixture was treated with 1 N hydrochloric acid and extracted with diethyl ether. The extract was washed with water and an aqueous solution of sodium chloride, dried over magnesium sulphate and concentrated under reduced pressure. The residue was purified by column chromatography on silica gel using a mixture of benzene and ethyl acetate (5:1) as eluent to give 630 mg. of the title compound, 755 mg. of its 15R-hydroxy isomer and 437 mg. of their mixture. The title compound showed the following physical characteristics:

TLC (developing solvent, benzene-ethyl acetate = 2:1): Rf = 0.44, (15R-hydroxy isomer, Rf = 0.58);

IR (liquid film): $\nu = 3450$, 3000, 2930, 2850, 1730, 975 cm$^{-1}$;

NMR (CDCl$_3$ solution): $\delta = 5.9$–4.9 (5H,m), 4.9–4.5 (1H,m), 4.5–3.2 (8H,m).

1α-Acetoxy-2α-(6-methoxycarbonylhex-cis-2-enyl)-3β-(2-formyl-trans-vinyl)-4α-(2-tetrahydropyranyloxy)-cyclopentane was prepared from 1α-acetoxy-2α-(6-methoxycarbonylhex-cis-2-enyl)-3β-formyl-4α-(2-tetrahydropyranyloxy)cyclopentane (prepared as described in Reference Example 2) as follows:

1.2 g of 1α-acetoxy-2α-(6-methoxycarbonylhex-cis-2-enyl)-3β-formyl-4α-(2-tetrahydropyranyloxy)cyclopentane and 1.8 g. of formylmethylenetriphenylphosphorane [prepared as described in J. Chem. Soc., 1266 (1961)] were dissolved in 15 ml. of anhydrous benzene and refluxed for 5 hours with stirring. The reaction mixture was diluted with 500 ml. of benzene, washed with an aqueous solution of oxalic acid, a saturated aqueous solution of sodium bicarbonate and a saturated aqueous solution of sodium chloride, dried over magnesium sulphate and concentrated under reduced pressure. The residue was purified by column chromatography on silica gel using a mixture of ethyl acetate and benzene (1:5) as eluent to give 1.03 g. of 1α-acetoxy-2α-(6-methoxycarbonylhex-cis-2-enyl)-3β-(2-formyl-trans-vinyl)-4α-(2-tetrahydropyranyloxy)cyclopentane having the following physical characteristics:

TLC (developing solvent, ethyl acetate-benzene = 1:2): Rf = 0.48;

IR (liquid film): $\nu = 2940$, 1737, 1691, 1635, 1246, 1127, 1132, 974 cm$^{-1}$;

NMR(CDCl$_3$ + dimethylsulphoxide-d$_6$ solution): $\delta = 5.10$–4.60 (1H,m), 4.29 (2H,s), 4.13–3.77 (1H,d).

EXAMPLE 34

9α,15S-Dihydroxy-11α-(2-tetrahydropyranyloxy)-15-(3-ethylcyclohexyl)-16,17,18,19,20-pentanorprosta-cis-5,trans-13-dienoic acid By proceeding as described in Example 1 but replacing the methyl 9α-acetoxy-11α-(2-tetrahydropyranyloxy)-15S-hydroxy-15-(trans-4-ethylcyclohexyl)-16,17,18,19,20-pentanorprosta-cis-5,trans-13-dienoate by 409 mg. of methyl 9α-acetoxy-11α-(2-tetrahydropyranyloxy)-15S-hydroxy-15-(3-ethylcyclohexyl)-16,17,18,19,20-pentanorprosta-cis-5,trans-13-dienoate (prepared as described in Reference Example 18) dissolved in 10 ml. of methanol and utilizing 4 ml. of a 2 N aqueous solution of potassium hydroxide, there were obtained 300 mg. of the title compound having the following physical characteristics:

TLC (developing solvent, methylene chloride-methanol = 19:1): Rf = 0.19;

IR (liquid film): $\nu = 3450$, 3000, 2930, 2850, 2800–2400, 1740, 1710, 975 cm$^{-1}$;

NMR(CDCl$_3$ solution): $\delta = 5.8$–5.2 (4H,m), 4.9–4.3 (4H,m), 4.3–3.2 (5H,m).

EXAMPLE 35

9α,11α-15S-Trihydroxy-15-(3-ethylcyclohexyl)-16,17,18,19,20-pentanorprosta-cis-5,trans-13-dienoic acid [or 15-(3-ethylcyclohexyl)-16,17,18,19,20-pentanor-PGF$_2$α]

By proceeding as described in Example 22 but replacing the methyl 9α,15R-dihydroxy-11α-(2-tetrahydropyranyloxy)-15-(1-methyl-3-propylcyclopentyl)-16,17,18,19,20-pentanorprosta-cis-5,trans-13-dienoate by 300 mg. of 9α,15S-dihydroxy-11α-(2-tetrahydropyranyloxy)-15-(3-ethylcyclohexyl)-16,17,18,19,20-pentanorprosta-cis-5,trans-13-dienoic acid (prepared as described in Example 34) dissolved in 4 ml. of tetrahydrofuran and utilizing 3 ml. of 1 N hydrochloric acid, there were obtained 107 mg. of the title compound having the following physical characteristics:

TLC (developing solvent, chloroform-tetrahydrofuran-acetic acid = 10:2:1): Rf = 0.15;

IR (liquid film): $\nu = 3400$, 2970, 2950, 2860, 2800–2250, 1740, 1708, 975 cm$^{-1}$;

NMR(CDCl$_3$ solution): $\delta = 5.80$–5.23 (4H,m), 5.02 (4H, broad s) 4.30–3.60 (3H,m), 1.0–0.7 (3H,m).

REFERENCE EXAMPLE 19

Methyl 9α-acetoxy-11α,15S-bis(2-tetrahydropyranyloxy)-15-(3-ethylcyclohexyl)-16,17,18,19,20-pentanorprosta-cis-5,trans-13-dienoate By proceeding as described in Reference Example 4 but replacing the methyl 9α-acetoxy-11α-(2-tetrahydropyranyloxy)-15S-hydroxy-15-(trans-4-ethylcyclohexyl)-16,17,18,19,20-pentanorprosta-cis-5,trans-13-dienoate by 1.063 g. of methyl 9α-acetoxy-11α-(2-tetrahydropyranyloxy)-15S-hydroxy-15-(3-ethylcyclohexyl)-16,17,18,19,20-pentanorprosta-cis-5,trans-13-dienoate (prepared as described in Reference Example 18) dissolved in 20 ml. of methylene chloride and utilizing a catalytic amount of p-toluenesulphonic acid and 0.82 ml. of 2,3-dihydropyran, there were obtained 1.23 g. of the title compound having the following physical characteristic:
TLC (developing solvent, benzene-ethyl acetate=2:1): Rf=0.64.

EXAMPLE 36

9α-Hydroxy-11α,15S-bis(2-tetrahydropyranyloxy)-15-(3-ethylcyclohexyl)-16,17,18,19,20-pentanorprosta-cis-5,trans-13-dienoic acid By proceeding as described in Example 1 but replacing the methyl 9α-acetoxy-11α-(2-tetrahydropyranyloxy)-15S-hydroxy-15-(trans-4-ethylcyclohexyl)-16,17,18,19,20-pentanorprosta-cis-5,trans-13-dienoate by 600 mg. of methyl 9α-acetoxy-11α,15S-bis(2-tetrahydropyranyloxy)-15-(3-ethylcyclohexyl)-16,17,18,19,20-pentanorprosta-cis-5,trans-13-dienoate (prepared as described in Reference Example 19) dissolved in 10 ml. of methanol and utilizing 6 ml. of a 2 N aqueous solution of potassium hydroxide, there were obtained 405 mg. of the title compound having the following physical characteristics:
TLC (developing solvent, methylene chloride-methanol=20:1): Rf=0.18;
IR (liquid film): $\nu$=3450, 2950, 1730, 1700 cm$^{-1}$;
NMR(CDCl$_3$ solution): $\delta$=6.7–5.9 (2H,m), 5.8–5.0 (4H,m), 4.9–4.4 (2H,m), 4.4–3.0 (7H,m).

EXAMPLE 37

9-Oxo-11α,15S-bis(2-tetrahydropyranyloxy)-15-(3-ethylcyclohexyl)-16,17,18,19,20-pentanorprosta-cis-5,trans-13-dienoic acid By proceeding as described in Example 4 but replacing the 9α-hydroxy-11α,15S-bis(2-tetrahydropyranyloxy)-15-trans-4-ethylcyclohexyl)-16,17,18,19,20-pentanorprosta-cis-5,trans-13-dienoic acid by 389 mg. of 9α-hydroxy-11α,15S-bis(2-tetrahydropyranyloxy)-15-(3-ethylcyclohexyl)-16,17,18,19,20-pentanorprosta-cis-5,trans-13-dienoic acid (prepared as described in Example 36) dissolved in 40 ml. of diethyl ether and utilizing 12.8 ml. of the chromic acid solution, there were obtained 334 mg. of the title compound having the following physical characteristics:
TLC (developing solvent, chloroform-tetrahydrofuran-acetic acid=10:2:1): Rf=0.74;
IR (liquid film): $\nu$=2950, 1740, 1700 cm$^{-1}$;
NMR(CDCl$_3$ solution): $\delta$=5.8–5.0 (4H,m), 5.0–4.3 (2H,m), 4.3–3.2 (7H,m).

EXAMPLE 38

9-Oxo-11α,15S-dihydroxy-15-(3-ethylcyclohexyl)-16,17,18,19,20-pentanorprosta-cis-5,trans-13-dienoic acid [or 15-(3-ethylcyclohexyl)-16,17,18,19,20-pentanor-PGE$_2$]

By proceeding as described in Example 2 but replacing the 9α,15S-dihydroxy-11α-(2-tetrahydropyranyloxy)-15-(trans-4-ethylcyclohexyl)-16,17,18,19,20-pentanorprosta-cis-5,trans-13-dienoic acid by 334 mg. of 9α-oxo-11α,15S-bis(2-tetrahydropyranyloxy)-15-(3-ethylcyclohexyl)-16,17,18,19,20-pentanorprosta-cis-5,trans-13-dienoic acid (prepared as described in Example 37) dissolved in a mixture of 3 ml. of tetrahydrofuran and 15 ml. of a 65% aqueous solution of acetic acid, there were obtained 168 mg. of the title compound having the following physical characteristics:
TLC (developing solvent, chloroform-tetrahydrofuran-acetic acid=10:2:1): Rf=0.30;
IR (liquid film): $\nu$=3400, 2950, 1730, 1700, 975 cm$^{-1}$;
NMR(CDCl$_3$ solution): $\delta$=5.9–5.2 (7H,m), 4.2–3.7 (2H,m), 2.75 (1H,dd), 1.0–0.7 (3H,m).

EXAMPLE 39

Methyl 9α-hydroxy-11α,15S-bis(2-tetrahydropyranyloxy)-15-(3-ethylcyclohexyl)-16,17,18,19,20-pentanorprosta-cis-5,trans-13-dienoate By proceeding as described in Example 9 but replacing the methyl 9α-acetoxy-11α-(2-tetrahydropyranyloxy)-15S-hydroxy-15-(3-propylcyclopentyl)-16,17,18,19,20-pentanorprosta-cis-5,trans-13-dienoate by 820 mg. of methyl 9α-acetoxy-11α,15S-bis(2-tetrahydropyranyloxy)-15-(3-ethylcyclohexyl)-16,17,18,19,20-pentanorprosta-cis-5,trans-13-dienoate (prepared as described in Reference Example 19) dissolved in 10 ml. of methanol and utilizing 164 mg. of anhydrous potassium carbonate, there were obtained 576 mg. of the title compound having the following physical characteristics:
TLC (developing solvent, benzene-ethyl acetate=2:1): Rf=0.44;
IR (liquid film): $\nu$=3500, 2950, 1740 cm$^{-1}$;
NMR(CDCl$_3$ solution): $\delta$=5.7–5.1 (4H,m), 4.8–4.4 (2H,m), 4.3–3.1 (11H,m).

EXAMPLE 40

Methyl 9α-hydroxy-11α,15S-bis(2-tetrahydropyranyloxy)-15-(3-ethylcyclohexyl)-16,17,18,19,20-pentanorprost-trans-13-enoate By proceeding as described in Example 6 but replacing the 9α-hydroxy-11α,15S-bis(2-tetrahydropyranyloxy)-15-(trans-4-ethylcyclohexyl)-16,17,18,19,20-pentanorprosta-cis-5,trans-13-dienoic acid by 517 mg. of methyl 9α-hydroxy-11α,15S-bis(2-tetrahydropyranyloxy)-15-(3-ethylcyclohexyl)-16,17,18,19,20-pentanorprosta-cis-5,trans-13-dienoate (prepared as described in Example 39) dissolved in 20 ml. of methanol and utilizing 150 mg. of 5% palladium on charcoal, there were obtained 456 mg. of the title compound having the following physical characteristics:
TLC (developing solvent, benzene-ethyl acetate=2:1): Rf=0.35;
NMR(CDCl$_3$ +D$_2$O solution): $\delta$=5.6–5.1 (2H,m), 4.9–4.4 (2H,m), 4.4–3.1 (11H,m).

EXAMPLE 41

Methyl 9-oxo-11α,15S-bis(2-tetrahydropyranyloxy)-15-(3-ethylcyclohexyl)-16,17,18,19,20-pentanorprost-trans-13-enoate By proceeding as described in Example 4 but replacing the 9α-hydroxy-11α,15S-bis(2-tetrahydropyranyloxy)-15-(trans-4-ethylcyclohexyl)-16,17,18,19,20-pentanorprosta-cis-5,trans-13-dienoic acid by 456 mg. of methyl 9α-hydroxy-11α,15S-bis(2-tetrahydropyranyloxy)-15-(3-ethylcyclohexyl)-16,17,18,19,20-pentanorprost-trans-13-enoate (prepared as described in Example 40) dissolved in 50 ml. of diethyl ether and utilizing 20 ml. of the chromic acid solution, there were obtained 409 mg. of the title compound having the following physical characteristics:
TLC (developing solvent, benzene-ethyl acetate=2:1): Rf=0.65;
IR (liquid film): $\nu$=2950, 1735 cm$^{-1}$;
NMR(CDCl$_3$ solution): $\delta$=5.8–5.2 (2H,m), 4.9–4.4 (2H,m), 4.4–3.1 (9H,m).

EXAMPLE 42

Methyl 9-oxo-11α,15S-dihydroxy-15-(3-ethylcyclohexyl)-16,17,18,19,20-pentanorprost-trans-13-enoate [or 15-(3-ethylcyclohexyl)-16,17,18,19,20-pentanor-PGE$_1$ methyl ester]

By proceeding as described in Example 2 but replacing the 9α,15S-dihydroxy-11α-(2-tetrahydropyranyloxy)-15-(trans-4-ethylcyclohexyl)-16,17,18,19,20-pentanorprosta-cis-5,trans-13-dienoic acid by 409 mg. of methyl 9-oxo-11α,15S-bis(2-tetrahydropyranyloxy)-15-(3-ethylcyclohexyl)-16,17,18,19,20-pentanorprost-trans-13-enoate (prepared as described in Example 41) dissolved in a mixture of 5 ml. of tetrahydrofuran and 20 ml. of a 65% aqueous solution of acetic acid, there were obtained 186 mg. of the title compound having the following physical characteristics:
TLC (developing solvent, chloroform-tetrahydrofuran-acetic acid=10:2:1) Rf=0.36;
IR (liquid film): $\nu$=3400, 2970, 2950, 2870, 1740, 970 cm$^{-1}$;
NMR (CDCl$_3$ solution): $\delta$=5.70–5.45 (2H,m), 4.20–3.60 (4H,m), 3.66 (3H,s), 2.74 (1H,dd), 1.0–0.7 (3H,m).

REFERENCE EXAMPLE 20

Dimethyl 2-oxo-2-(3-ethylcyclopentyl)ethylphosphonate

By proceeding as described in Reference Example 5 but replacing the 1-methoxycarbonyl-3-propylcyclopentane by 6.956 g. of 1-methoxycarbonyl-3-ethylcyclopentane dissolved in 40 ml. of dry tetrahydrofuran and utilizing a solution of 11 g. of dimethyl methylphosphonate in 110 ml. of dry tetrahydrofuran and 64 ml. of a 1.4 M solution of n-butyllithium in n-hexane, there were obtained 10.426 g. of the title compound having the following physical characteristics:
TLC (developing solvent, ethyl acetate): Rf=0.45;
IR (liquid film): $\nu$=3500, 2960, 2860, 1710, 1455, 1390, 1375, 1260, 1185, 1030 cm$^{-1}$;
NMR (CDCl$_3$ solution): $\delta$=3.73 (6H,d), 3.10 (2H,d), 2.5–1.1 (10H,m), 0.88 (3H,t).

REFERENCE EXAMPLE 21

Methyl 9α-acetoxy-11α-(2-tetrahydropyranyloxy)-15-oxo-15-(3-ethylcyclopentyl)-16,17,18,19,20-pentanorprosta-cis-5,trans-13-dienoate By proceeding as described in Reference Example 2 but replacing the dimethyl 2-oxo-2-(trans-4-ethylcyclohexyl)-ethylphosphonate by 3.2 g. of dimethyl 2-oxo-2-(3-ethylcyclopentyl)ethylphosphonate (prepared as described in Reference Example 20) dissolved in 15 ml. of dry tetrahydrofuran and utilizing a suspension of 470 mg. of sodium hydride (63% content) in 60 ml. of dry tetrahydrofuran and 3.96 g. of 1α-acetoxy-2α-(6-methoxycarbonylhex-cis-2-enyl)-3β-formyl-4α-(2-tetrahydropyranyloxy)cyclopentane in 15 ml. of dry tetrahydrofuran, there were obtained 3.775 g. of the title compound having the following physical characteristics:
TLC (developing solvent, benzene-ethyl acetate=4:1): Rf=0.60;
IR (liquid film): $\nu$=2950, 2870, 1735, 1685, 1660, 1620, 1430, 1370, 1240, 970 cm$^{-1}$;
NMR (CDCl$_3$ solution): $\delta$=7.2–6.1 (2H,m), 5.8–5.0 (3H,m), 4.9–4.5 (1H,m), 3.72 (3H,s), 2.1 (3H,s), 0.9 (3H,t).

REFERENCE EXAMPLE 22

Methyl 9α-acetoxy-11α-(2-tetrahydropyranyloxy)-15S-hydroxy-15-(3-ethylcyclopentyl)-16,17,18,19,20-pentanorprosta-cis-5,trans-13-dienoate By proceeding as described in Reference Example 3 but replacing the methyl 9α-acetoxy-11α-(2-tetrahydropyranyloxy)-15-oxo-15-(trans-4-ethylcyclohexyl)-16,17,18,19,20-pentanorprosta-cis-5,trans-13-dienoate by 3.775 g. of methyl 9α-acetoxy-11α-(2-tetrahydropyranyloxy)-15-oxo-15-(3-ethylcyclopentyl)-16,17,18,19,20-pentanorprosta-cis-5,trans-13-dienoate (prepared as described in Reference Example 21) dissolved in 40 ml. of methanol and utilizing 811 mg. of sodium borohydride, there were obtained 1.571 g. of the title compound, 1.624 g. of its 15R-hydroxy isomer and 0.286 g. of their mixture. The title compound showed the following physical characteristics:
TLC (developing solvent, chloroform-tetrahydrofuran-acetic acid=10:2:1): RF=0.65, (15R-hydroxy isomer, Rf=0.71);
IR (liquid film): $\nu$=3500, 2950, 2875, 1733, 1430, 1370, 1240, 1135, 1020, 975 cm$^{-1}$;
NMR (CDCl$_3$ solution): $\delta$=5.9–5.5 (2H,m), 5.5–5.2 (2H,m), 5.2–4.9 (1H,m), 4.9–4.4 (1H,m), 3.65 (3H,s), 2.03 (3H,s), 0.88 (3H,t).

EXAMPLE 43

9α,15S-Dihydroxy-11α-(2-tetrahydropyranyloxy)-15-(3-ethylcyclopentyl)-16,17,18,19,20-pentanorprosta-cis-5,trans-dienoic acid By proceeding as described in Example 1 but replacing the methyl 9α-acetoxy-11α-(2-tetrahydropyranyloxy)-15S-hydroxy-15-(trans-4-ethylcyclohexyl)-16,17,18,19,20-pentanorprosta-cis-5,trans-13-dienoate by 524 mg. of methyl 9α-acetoxy-11α-(2-tetrahydropyranyloxy)-15S-hydroxy-15-(3-ethylcyclopentyl)-16,17,18,19,20-pentanorprosta-cis-5,trans-13-dienoate (prepared as described in Reference Example 22) dissolved in 5 ml. of ethanol and utilizing 6 ml. of a 5% aqueous solution of potassium hydroxide, there were obtained 442 mg. of the title compound having the following physical characteristics:
TLC (developing solvent, chloroform-tetrahydrofuran-acetic acid=10:2:1): Rf=0.66;
IR (liquid film): $\nu$=3450, 2950, 2870, 1710, 1440, 1370, 1240, 1130, 1020, 970 cm$^{-1}$;
NMR (CDCl$_3$ solution): $\delta$=5.8–5.2 (4H,m), 5.0–4.4 (4H,m), 4.4–3.2 (5H,m), 0.90 (3H,t).

EXAMPLE 44

9α,11α,15S-Trihydroxy-15-(3-ethylcyclopentyl)-16,17,18,19,20-pentanorprosta-cis-5,trans-13-dienoic acid [or 15-(3-ethylcyclopentyl)-16,17,18,19,20-pentanor-PGF$_{2α}$]

By proceeding as described in Example 22 but replacing the methyl 9α,15R-dihydroxy-11α-(2-tetrahydropyranyloxy)-15-(1-methyl-3-propylcyclopentyl)-16,17,18,19,20-pentanorprosta-cis-5,trans-13-dienoate by 442 mg. of 9α,15S-dihydroxy-11α-(2-tetrahydropyranyloxy)-15-(3-ethylcyclopentyl)-16,17,18,19,20-pentanorprosta-cis-5,trans-13-dienoic acid (prepared as described in Example 43) dissolved in a mixture of 3 ml. of tetrahydrofuran and 4 ml. of 1 N hydrochloric acid, there were obtained 13 mg. of the title compound (isomer A) and 37 mg. of the title compound (isomer B) having the following physical characteristics:
TLC (developing solvent, chloroform-tetrahydrofuran-acetic acid = 10:2:1): isomer A, Rf = 0.24 isomer B, Rf = 0.13;
IR (liquid film): ν = 3350, 2950, 2860, 1710, 1440, 1240, 1050, 970 cm$^{-1}$;
NMR (CDCl$_3$ solution): δ = 5.8–5.2 (4H,m), 5.2–4.8 (4H,m), 4.3–4.04 (1H,m), 4.04–3.6 (2H,m), 0.87 (3H,t).

REFERENCE EXAMPLE 23

Methyl 9α-acetoxy-11α,15S-bis(2-tetrahydropyranyloxy)-15-(3-ethylcyclopentyl)-16,17,18,19,20-pentanorprosta-cis-5,trans-13-dienoate By proceeding as described in Reference Example 4 but replacing the methyl 9α-acetoxy-11α-(2-tetrahydropyranyloxy)-15S-hydroxy-15-(trans-4-ethylcyclohexyl)-16,17,18,19,20-pentanorprosta-cis-5,trans-13-dienoate by 1.047 g. of methyl 9α-acetoxy-11α-(2-tetrahydropyranyloxy)-15S-hydroxy-15-(3-ethylcyclopentyl)-16,17,18,19,20-pentanorprosta-cis-5,trans-13-dienoate (prepared as described in Reference Example 22) dissolved in 7 ml. of dry methylene chloride and utilizing 5 mg. of p-toluenesulphonic acid and 0.3 ml. of 2,3-dihydropyran, there were obtained 1.2 g. of the title compound having the following physical characteristics:
TLC (developing solvent, benzene-ethyl acetate = 4:1): Rf = 0.53;
IR (liquid film): ν = 2950, 2870, 1735, 1430, 1370, 1240, 1130, 1020, 970 cm$^{-1}$;
NMR (CDCl$_3$ solution): δ = 5.8–5.2 (4H,m), 5.2–4.85 (1H,m), 4.85–4.5 (2H,m), 3.68 (3H,s), 2.05 (3H,s), 0.9 (3H,t).

EXAMPLE 45

9α-Hydroxy-11α,15S-bis(2-tetrahydropyranyloxy)-15-(3-ethylcyclopentyl)-16,17,18,19,20-pentanorprosta-cis-5,trans-13-dienoic acid By proceeding as described in Example 1 but replacing the methyl 9α-acetoxy-11α-(2-tetrahydropyranyloxy)-15S-hydroxy-15-(trans-4-ethylcyclohexyl)-16,17,18,19,20-pentanorprosta-cis-5,trans-13-dienoate by 1.2 g. of methyl 9α-acetoxy-11α,15S-bis(2-tetrahydropyranyloxy)-15-(3-ethylcyclopentyl)-16,17,18,19,20-pentanorprosta-cis-5,trans-13-dienoate (prepared as described in Reference Example 23) dissolved in a mixture of 10 ml. of ethanol and 5 ml. of tetrahydrofuran and utilizing 10 ml. of a 2 N aqueous solution of potassium hydroxide, there were obtained 1.05 g. of the crude title compound having the following physical characteristics:
TLC (developing solvent, methylene chloride-methanol = 20:1): Rf = 0.22;
IR (liquid film): ν = 3450, 2950, 2870, 1735, 1710, 1430, 1240, 1130, 1020, 970 cm$^{-1}$;
NMR (CDCl$_3$ solution): δ = 6.5–5.7 (2H,m), 5.7–5.2 (4H,m), 4.95–4.5 (2H,m), 4.5–3.1 (7H,m), 0.88 (3H,t).

EXAMPLE 46

9-Oxo-11α,15S-bis(2-tetrahydropyranyloxy)-15-(3-ethylcyclopentyl)-16,17,18,19,20-pentanorprosta-cis-5,trans-13-dienoic acid By proceeding as described in Example 4 but replacing the 9α-hydroxy-11α,15S-bis(2-tetrahydropyranyloxy)-15-(trans-4-ethylcyclohexyl)-16,17,18,19,20-pentanorprosta-cis-5,trans-13-dienoic acid by 1.05 g. of 9α-hydroxy-11α,15S-bis(2-tetrahydropyranyloxy)-15-(3-ethylcyclopentyl)-16,17,18,19,20-pentanorprosta-cis-5,trans-13-dienoic acid (prepared as described in Example 45) dissolved in 30 ml. of diethyl ether and utilizing 70 ml. of the chromic acid solution, there were obtained 874 mg. of the title compound having the following physical characteristics:
TLC (developing solvent, methylene chloride-methanol = 20:1): Rf = 0.21;
IR (liquid film): ν = 2950, 2870, 1740, 1705, 1440, 1370, 1240, 1200, 1135, 1080, 1040, 1020, 975 cm$^{-1}$;
NMR (CDCl$_3$ solution): δ = 5.9–5.1 (4H,m) 4.9–4.5 (2H,m), 2.75 (1H,dd), 0.86 (3H,t).

EXAMPLE 47

9-Oxo-11α,15S-dihydroxy-15-(3-ethylcyclopentyl)-16,17,18,19,20-pentanorprosta-cis-5,trans-13-dienoic acid [or 15-(3-ethylcyclopentyl)-16,17,18,19,20-pentanor-PGE$_2$]

By proceeding as described in Example 2 but replacing the 9α,15S-dihydroxy-11α-(2-tetrahydropyranyloxy)-15-(trans-4-ethylcyclohexyl)-16,17,18,19,20-pentanorprosta-cis-5,trans-13-dienoic acid by 870 mg. of 9-oxo-11α,15S-bis(2-tetrahydropyranyloxy)-15-(3-ethylcyclopentyl)-16,17,18,19,20-pentanorprosta-cis-5,trans-13-dienoic acid (prepared as described in Example 46) dissolved in a mixture of 5 ml. of tetrahydrofuran and 13 ml. of 65% aqueous acetic acid, there were obtained 405 mg. of the title compound having the following physical characteristics:
TLC (developing solvent, chloroform-tetrahydrofuran-acetic acid = 10:2:1): Rf = 0.31;
IR (liquid film): ν = 3350, 2950, 2875, 1735, 1705, 1440, 1400, 1240, 1155, 1070, 970 cm$^{-1}$;
NMR (CDCl$_3$ solution): δ = 5.9–5.0 (7H,m), 4.3–3.5 (2H,m), 2.75 (1H,dd), 0.88 (3H,t).

EXAMPLE 48

2-Tetrahydropyranyl 9-oxo-11α,15S-bis(2-tetrahydropyranyloxy)-15-(3-ethylcyclopentyl)-16,17,18,19,20-pentanorprosta-cis-5,trans-13-dienoate To a solution of 119 mg. of 9-oxo-11α,15S-dihydroxy-15-(3-ethylcyclopentyl)-16,17,18,19,20-pentanorprosta-cis-5,trans-13-dienoic acid (prepared as described in Example 47) in 2 ml. of absolute methylene chloride were added 0.1 ml. of 2,3-dihydropyran and 1.6 mg. of p-toluenesulphonic acid at 0° to 5° C. and the mixture was stirred at the same temperature for 15 minutes. The reaction mixture was diluted with ethyl acetate, then washed with a saturated aqueous solution of sodium bicarbonate and an aqueous solution of sodium chloride, dried over magnesium sulphate and concentrated under reduced pressure. The residue was purified by column chromatography on silica gel using a mixture of benzene and ethyl acetate (4:1) as eluent to give 158 mg. of the title compound having the following physical characteristics:

TLC (developing solvent, methylene chloride-methanol=20:1): Rf=0.56;
IR (liquid film): $\nu$=2950, 2890, 1740, 1440, 1350, 1200, 1130, 1070, 1040, 1025, 970 cm$^{-1}$;
NMR (CDCl$_3$ solution): $\delta$=6.04–5.89 (1H,m), 5.8–5.14 (4H,m), 5.04–4.87 (1H,m), 4.87–4.48 (2H,m), 4.25–3.22 (8H,m), 0.88 (3H,t).

EXAMPLE 49

2-Tetrahydropyranyl 9-oxo-11α,15S-bis(2-tetrahydropyranyloxy)-15-(3-ethylcyclopentyl)-16,17,18,19,20-pentanorprost-trans-13-enoate and 2-tetrahydropyranyl 9-oxo-11α,15R-bis(2-tetrahydropyranyloxy)-15-(3-ethylcyclopentyl)-16,17,18,19,20-pentanorprostanoate By proceeding as described in Example 6 but replacing the 9α-hydroxy-11α,15S-bis(2-tetrahydropyranyloxy)-15-(trans-4-ethylcyclohexyl)-16,17,18,19,20-pentanorprosta-cis-5,trans-13-dienoic acid by 158 mg. of 2-tetrahydropyranyl 9-oxo-11α,15S-bis(2-tetrahydropyranyloxy)-15-(3-ethylcyclopentyl)-16,17,18,19,20-pentanorprosta-cis-5,trans-13-dienoate (prepared as described in Example 48) dissolved in 2 ml. of methanol and utilizing 25 mg. of 5% palladium on charcoal, there were obtained 158 mg. of the mixture of the title compounds having the following physical characteristics:

TLC (developing solvent, methylene chloride-methanol=20:1): Rf=0.47 and 0.53;
NMR (CDCl$_3$ solution): $\delta$=6.04–5.88 (1H,m), 5.77–5.2 (0.8H,m), 5.04–4.88 (1H,m), 4.88–4.45 (2H,m), 4.40–3.20 (8H,m), 0.88 (3H,t).

EXAMPLE 50

9-Oxo-11α,15S-dihydroxy-15-(3-ethylcyclopentyl)-16,17,18,19,20-pentanorprost-trans-13-enoic acid [or 15-(3-ethylcyclopentyl)-16,17,18,19,20-pentanor-PGE$_1$] and 9-oxo-11α,15R-dihydroxy-15-(3-ethylcyclopentyl)-16,17,18,19,20-pentanorprostanoic acid [or 15-(3-ethylcyclopentyl)-13,14-dihydro-16,17,18,19,20-pentanor-PGE$_1$]

By proceeding as described in Example 2 but replacing the 9α,15S-dihydroxy-11α-(2-tetrahydropyranyloxy)-15-(trans-4-ethylcyclohexyl)-16,17,18,19,20-pentanorprosta-cis-5,trans-13-dienoic acid by 130 mg. of the mixture of 2-tetrahydropyranyl 9-oxo-11α,15S-bis(2-tetrahydropyranyloxy)-15-(3-ethylcyclopentyl)-16,17,18,19,20-pentanorprost-trans-13-enoate and 2-tetrahydropyranyl 9-oxo-11α,15R-bis(2-tetrahydropyranyloxy)-15-(3-ethylcyclopentyl)-16,17,18,19,20-pentanorprostanoate (prepared as described in Example 49) dissolved in a mixture of 0.5 ml. of tetrahydrofuran and 5 ml. of a 65% aqueous solution of acetic acid, there were obtained 11 mg. of the PGE$_1$ compound as a white powder and 17 mg. of the 13,14-dihydro-PGE$_1$ compound as an oil, having the following physical characteristics:

(1) 15-(3-ethylcyclopentyl)-16,17,18,19,20-pentanor-PGE$_1$ melting point=107°–108° C.;
TLC (developing solvent, chloroform-tetrahydrofuran-acetic acid=10:2:1): Rf=0.33;
IR (KBr tablet): $\nu$=3500, 2950, 2860, 1740, 1720, 1080, 975 cm$^{-1}$;
NMR (CDCl$_3$ solution): $\delta$=5.6 (2H,t), 5.39 (3H, broad s), 4.25–3.64 (2H,m), 2.75 (1H,dd), 0.88 (3H,t);
(2) 15-(3-ethylcyclopentyl)-13,14-dihydro-16,17,18,19,20-pentanor-PGE$_1$
TLC (developing solvent, chloroform-tetrahydrofuran-acetic acid=10:2:1): Rf=0.46;
IR (liquid film): $\nu$=3400, 2940, 2855, 2700–2200, 1730, 1710, 1070 cm$^{-1}$;
NMR (CDCl$_3$ solution): $\delta$=5.37 (3H,broad s), 4.27–3.87 (1H,m), 3.56–3.28 (1H,m), 2.69 (1H,dd), 0.88 (3H,t).

REFERENCE EXAMPLE 24

Methyl 2-phenylseleno-9α-hydroxy-11α,15S-bis(2-tetrahydropyranyloxy)-15-(3-propylcyclopentyl)-16,17,18,19,20-pentanorprost-trans-13-enoate Under an atmosphere of nitrogen, 3.29 ml. of a 1.4 M solution of n-butyllithium in n-hexane were added dropwise to a solution of 0.64 ml. of diisopropylamine in 15 ml. of tetrahydrofuran at −70° C. and the mixture was stirred at the same temperature for 20 minutes to give the lithium diisopropylamide solution. To it was added dropwise a solution of 1.01 g. of methyl 9α-hydroxy-11α,15S-bis(2-tetrahydropyranyloxy)-15-(3-propylcyclopentyl)-16,17,18,19,20-pentanorprost-trans-13-enoate (prepared as described in Example 14) in 8 ml. of tetrahydrofuran at −70° C. and the mixture was stirred at that temperature for 10 minutes. To the solution thus obtained was added dropwise a solution of 1.5 g. of diphenyldiselenide in 10 ml. of tetrahydrofuran at −70° C. and the mixture was stirred at the same temperature for 1.5 hours. The reaction mixture was then poured into a saturated aqueous solution of ammonium chloride and extracted with ethyl acetate. The extract was washed with water, 1 N hydrochloric acid, an aqueous solution of sodium bicarbonate and an aqueous solution of sodium chloride, dried over magnesium sulphate and concentrated under reduced pressure. The residue was purified by column chromatography on silica gel using a mixture of benzene and ethyl acetate (6:1) as eluent to give 852 mg. of the title compound having the following physical characteristic:

TLC (developing solvent, benzene-ethyl acetate=2:1): Rf=0.54.

EXAMPLE 51

Methyl 9α-hydroxy-11α,15S-bis(2-tetrahydropyranyloxy)-15-(3-propylcyclopentyl)-16,17,18,19,20-pentanorprosta-trans-2,trans-13-dienoate To a solution of 852 mg. of methyl 2-phenylseleno-9α-hydroxy-11α,15S-bis(2-tetrahydropyranyloxy)-15-(3-propylcyclopentyl)-16,17,18,19,20-pentanorprost-trans-13-enoate (prepared as described in Reference Example 24) in a mixture of 15 ml. of ethyl acetate and 9 ml. of tetrahydrofuran were added dropwise 0.9 ml. of 30% hydrogen peroxide at 37° C. and the mixture was stirred at that temperature for 30 minutes. The reaction mixture was then diluted with ethyl acetate, washed with water, an aqueous solution of sodium carbonate and an aqueous solution of sodium chloride, dried over magnesium sulphate and concentrated under reduced pressure to give 623 mg. of the crude title compound having the following physical characteristics:
TLC (developing solvent, benzene-ethyl acetate=2:1): Rf=0.35;
NMR (CCl$_4$ solution): δ=7.3–6.5 (1H,m), 6.05–5.0 (3H,m), 4.9–4.4 (2H,m), 4.4–3.0 (10H,m).

EXAMPLE 52

9α-Hydroxy-11α,15S-bis(2-tetrahydropyranyloxy)-15-(3-propylcyclopentyl)-16,17,18,19,20-pentanorprosta-trans-2,trans-13-dienoic acid By proceeding as described in Example 1 but replacing the methyl 9α-acetoxy-11α-(2-tetrahydropyranyloxy)-15S-hydroxy-15-(trans-4-ethylcyclohexyl)-16,17,18,19,20-pentanorprosta-cis-5,trans-13-dienoate by 623 mg. of methyl 9α-hydroxy-11α,15S-bis(2-tetrahydropyranyloxy)-15-(3-propylcyclopentyl)-16,17,18,19,20-pentanorprosta-trans-2,trans-13-dienoate (prepared as described in Example 51) dissolved in a mixture of 5 ml. of ethanol and 1.2 ml. of tetrahydrofuran and utilizing 2.4 ml. of a 2 N aqueous solution of potassium hydroxide, there were obtained 567 mg. of the title compound having the following physical characteristic: TLC (developing solvent, methylene chloride-methanol=10:1): Rf=0.46.

EXAMPLE 53

9-Oxo-11α,15S-bis(2-tetrahydropyranyloxy)-15-(3-propylcyclopentyl)-16,17,18,19,20-pentanorprosta-trans-2,trans-13-dienoic acid By proceeding as described in Example 4 but replacing the 9α-hydroxy-11α,15S-bis(2-tetrahydropyranyloxy)-15-(trans-4-ethylcyclohexyl)-16,17,18,19,20-pentanorprosta-cis-5,trans-13-dienoic acid by 567 mg. of 9α-hydroxy-11α,15S-bis(2-tetrahydropyranyloxy)-15-(3-propylcyclopentyl)-16,17,18,19,20-pentanorprosta-trans-2,trans-13-dienoic acid (prepared as described in Example 52) dissolved in 12.8 ml. of diethyl ether and utilizing 10.5 ml. of the chromic acid solution, there were obtained 420 mg. of the title compound having the following physical characteristics:
TLC (developing solvent, methylene chloride-methanol=10:1): Rf=0.42;
NMR (CCl$_4$ solution): δ=7.2–6.7 (1H,m), 6.5–5.1 (3H,m), 4.9–4.35 (2H,m), 4.3–3.1 (6H,m), 2.75 (1H,dd).

EXAMPLE 54

9-Oxo-11α,15S-dihydroxy-15-(3-propylcyclopentyl)-16,17,18,19,20-pentanorprosta-trans-2,trans-13-dienoic acid [or 15-(3-propylcyclopentyl)-16,17,18,19,20-pentanor-trans-Δ$^2$-PGE$_1$]

By proceeding as described in Example 2 but replacing the 9α,15S-dihydroxy-11α-(2-tetrahydropyranyloxy)-15-(trans-4-ethylcyclohexyl)-16,17,18,19,20-pentanorprosta-cis-5,trans-13-dienoic acid by 420 mg. of 9-oxo-11α,15S-bis(2-tetrahydropyranyloxy)-15-(3-propylcyclopentyl)-16,17,18,19,20-pentanorprosta-trans-2,trans-13-dienoic acid (prepared as described in Example 53) dissolved in a mixture of 1.5 ml. of tetrahydrofuran and 8.4 ml. of a 65% aqueous solution of acetic acid, there were obtained 136 mg. of the title compound having the following physical characteristics:
TLC (developing solvent, chloroform-tetrahydrofuran-acetic acid=10:2:1): Rf=0.32;
IR (liquid film): ν=3400, 2950, 2860, 1750, 1700, 1650, 1420, 1160, 1080, 980 cm$^{-1}$;
NMR (CDCl$_3$ solution): δ=7.2–6.7 (1H,m), 6.1–5.45 (3H,m), 5.27 (3H, broad s), 4.35–3.6 (2H,m), 2.75 (1H,dd).

REFERENCE EXAMPLE 25

1α-Acetoxy-2α-(6-methoxycarbonylhexyl)-3β-formyl-4α-(2-tetrahydropyranyloxy)-cyclopentane By proceeding as described in Example 6 but replacing the 9α-hydroxy-11α,15S-bis(2-tetrahydropyranyloxy)-15-(trans-4-ethylcyclohexyl)-16,17,18,19,20-pentanorprosta-cis-5,trans-13-dienoic acid by 1.15 g. of 1α-acetoxy-2α-(6-methoxycarbonylhex-cis-2-enyl)-3β-formyl-4α-(2-tetrahydropyranyloxy)cyclopentane (prepared as described in Reference Example 2) dissolved in 30 ml. of methanol and utilizing 290 mg. of 5% palladium on charcoal, there were obtained 1.12 g. of the title compound having the following physical characteristics:
TLC (developing solvent, benzene-ethyl acetate=2:1): Rf=0.49;
IR (liquid film): ν=2970, 2880, 2730, 1740, 1430, 1370, 1240, 1125, 1015, 960 cm$^{-1}$;
NMR (CDCl$_3$ solution): δ=9.75 (1H,t), 5.3–4.9 (1H,m), 4.8–4.1 (1H,m), 3.65 (3H,s), 2.06 (3H,s).

REFERENCE EXAMPLE 26

Methyl 9α-acetoxy-11α-(2-tetrahydropyranyloxy)-15-oxo-15-(3-ethylcyclopentyl)-16,17,18,19,20-pentanorprost-trans-13-enoate By proceeding as described in Reference Example 21 but replacing the 1α-acetoxy-2α-(6-methoxycarbonylhex-cis-2-enyl)-3β-formyl-4α-(2-tetrahydropyranyloxy)cyclopentane by 1.12 g. of 1α-acetoxy-2α-(6-methoxycarbonylhexyl)-3β-formyl-4α-(2-tetrahydropyranyloxy)cyclopentane (prepared as described in Reference Example 25) dissolved in 5 ml. of dry tetrahydrofuran and utilizing a suspension of 125 mg. of sodium hydride (63% content) in 15 ml. of dry tetrahydrofuran and a solution of 907 mg. of dimethyl 2-oxo-2-(3-ethylcyclopentyl)ethylphosphonate (prepared as described in Reference Example 20) in 5 ml. of dry tetrahydrofuran, there were obtained 1.274 g. of the title compound having the following physical characteristics:
TLC (developing solvent, benzene-ethyl acetate=2:1): Rf=0.71;
IR (liquid film): ν2950, 2860, 1730, 1690, 1660, 1620, 1430, 1370, 1240, 1200, 1130, 1020, 970 cm$^{-1}$;
NMR (CDCl$_3$ solution): δ=6.8–6.0 (2H,m), 5.4–4.9 (1H,m), 4.7–4.4 (1H,m), 3.63 (3H,s), 2.05 (3H,s), 0.9 (3H,t).

REFERENCE EXAMPLE 27

Methyl 9α-acetoxy-11α-(2-tetrahydropyranyloxy)-15S-hydroxy-15-(3-ethylcyclopentyl)-16,17,18,19,20-pentanorprost-trans-13-enoate By proceeding as described in Reference Example 3 but replacing the methyl 9α-acetoxy-11α-(2-tetrahydropyranyloxy)-15-oxo-15-(trans-4-ethylcyclohexyl)-16,17,18,19,20-pentanorprosta-cis-5,trans-13-dienoate by 1.274 g. of methyl 9α-acetoxy-11α-(2-tetrahydropyranyloxy)-15-oxo-15-(3-ethylcyclopentyl)-16,17,18,19,20-pentanorprost-trans-13-enoate (prepared as described in Reference Example 26) dissolved in 20 ml. of methanol and utilizing 278 mg. of sodium borohydride, there were obtained 512 mg. of the title compound, 449 mg. of its 15R-hydroxy isomer and 160 mg. of their mixture. The title compound showed the following physical characteristics:

TLC (developing solvent, benzene-ethyl acetate=2:1): Rf=0.39, (its 15R-hydroxy isomer, Rf=0.50);

IR (liquid film): $\nu$=3450, 2950, 2860, 1735, 1430, 1370, 1245, 1130, 1020, 970 cm$^{-1}$;

NMR (CDCl$_3$ solution): $\delta$=5.8–5.4 (2H,m), 5.3–4.9 (1H,m), 4.8–4.5 (1H,m), 3.65 (3H,s), 2.05 (3H,s), 0.9 (3H,t).

REFERENCE EXAMPLE 28

Methyl 9α-acetoxy-11α,15S-bis(2-tetrahydropyranyloxy)-15-(3-ethylcyclopentyl)-16,17,18,19,20-pentanorprost-trans-13-enoate By proceeding as described in Reference Example 4 but replacing the methyl 9α-acetoxy-11α-(2-tetrahydropyranyloxy)-15S-hydroxy-15-(trans-4-ethylcyclohexyl)-16,17,18,19,20-pentanorprosta-cis-5,trans-13-dienoate by 512 mg. of methyl 9α-acetoxy-11α-(2-tetrahydropyranyloxy)-15S-hydroxy-15-(3-ethylcyclopentyl)-16,17,18,19,20-pentanorprost-trans-13-enoate (prepared as described in Reference Example 27) dissolved in 4 ml. of methylene chloride and utilizing 2.5 mg. of p-toluenesulphonic acid and 0.15 ml. of 2,3-dihydropyran, there were obtained 612 mg. of the title compound having the following physical characteristics:

TLC (developing solvent, benzene-ethyl acetate=4:1): Rf=0.50;

IR (liquid film): $\nu$=2925, 2850, 1730, 1430, 1370, 1240, 1195, 1130, 1070, 1020, 970 cm$^{-1}$;

NMR (CDCl$_3$ solution): $\delta$=5.8–5.3 (2H,m), 5.3–4.9 (1H,m), 4.9–4.5 (2H,m), 3.66 (3H,s), 2.05 (3H,s), 0.9 (3H,t).

EXAMPLE 55

Methyl 9α-hydroxy-11α,15S-bis(2-tetrahydropyranyloxy)-15-(3-ethylcyclopentyl)-16,17,18,19,20-pentanorprost-trans-13-enoate By proceeding as described in Example 9 but replacing the methyl 9α-acetoxy-11α-(2-tetrahydropyranyloxy)-15S-hydroxy-15-(3-propylcyclopentyl)-16,17,18,19,20-pentanorprosta-cis-5,trans-13-dienoate by 612 mg. of methyl 9α-acetoxy-11α,15S-bis(2-tetrahydropyranyloxy)-15-(3-ethylcyclopentyl)-16,17,18,19,20-pentanorprost-trans-13-enoate (prepared as described in Reference Example 28) dissolved in 8 ml. of methanol and utilizing 610 mg. of potassium carbonate, there were obtained 576 mg. of the title compound having the following physical characteristics:

TLC (developing solvent, benzene-ethyl acetate=4:1): Rf=0.40;

IR (liquid film): $\nu$=3450, 2930, 2850, 1735, 1430, 1350, 1255, 1200, 1130, 1075, 1020, 970 cm$^{-1}$;

NMR (CDCl$_3$ solution): $\delta$=5.7–5.15 (2H,m), 4.8–4.4 (2H,m), 3.59 (3H,s), 0.89 (3H,t).

REFERENCE EXAMPLE 29

Methyl 2-phenylseleno-9α-hydroxy-11α,15S-bis(2-tetrahydropyranyloxy)-15-(3-ethylcyclopentyl)-16,17,18,19,20-pentanorprost-trans-13-enoate By proceeding as described in Reference Example 24 but replacing the methyl 9α-hydroxy-11α,15S-bis(2-tetrahydropyranyloxy)-15-(3-propylcyclopentyl)-16,17,18,19,20-pentanorprost-trans-13-enoate by 576 mg. of methyl 9α-hydroxy-11α,15S-bis(2-tetrahydropyranyloxy)-15-(3-ethylcyclopentyl)-16,17,18,19,20-pentanorprost-trans-13-enoate (prepared as described in Example 55) dissolved in 3 ml. of dry tetrahydrofuran and utilizing 1.7 ml. of a 1.4 M solution of n-butyllithium in n-hexane, a solution of 0.34 ml. of diisopropylamine in 7 ml. of dry tetrahydrofuran, and a solution of 748 mg. of diphenyldiselenide in 4 ml. of dry tetrahydrofuran, there were obtained 259 mg. of the title compound and 136 mg. of the starting material. The title compound showed the following physical characteristics:

TLC (developing solvent, benzene-ethyl acetate=2:1): Rf=0.56;

IR (liquid film): $\nu$=3450, 2930, 2850, 1725, 1650, 1570, 1430, 1350, 1200, 1135, 1025, 975 cm$^{-1}$;

NMR (CDCl$_3$ solution): $\delta$=7.9–7.3 (5H,m), 5.8–5.3 (2H,m), 4.9–4.5 (2H,m), 3.69 (3H,s), 0.9 (3H,t).

EXAMPLE 56

Methyl 9α-hydroxy-11α,15S-bis(2-tetrahydropyranyloxy)-15-(3-ethylcyclopentyl)-16,17,18,19,20-pentanorprosta-trans-2,trans-13-dienoate By proceeding as described in Example 51 but replacing the methyl 2-phenylseleno-9α-hydroxy-11α,15S-bis(2-tetrahydropyranyloxy)-15-(3-propylcyclopentyl)-16,17,18,19,20-pentanorprost-trans-13-enoate by 259 mg. of methyl 2-phenylseleno-9α-hydroxy-11α,15S-bis(2-tetrahydropyranyloxy)-15-(3-ethylcyclopentyl)-16,17,18,19,20-pentanorprost-trans-13-enoate (prepared as described in Reference Example 29) dissolved in 4 ml. of a mixture of ethyl acetate and tetrahydrofuran (2:1) and utilizing 0.3 ml. of 30% hydrogen peroxide, there were obtained 201 mg. of the title compound having the following physical characteristics:

TLC (developing solvent, benzene-ethyl acetate=2:1): Rf=0.47;

IR (liquid film): $\nu$=3450, 2950, 2860, 1730, 1660, 1440, 1200, 1140, 1025, 980 cm$^{-1}$;

NMR (CDCl$_3$ solution): $\delta$=7.13 (1H,dt), 5.93 (1H,d), 5.9–5.3 (2H,m), 5.0–4.6 (2H,m), 3.8 (3H,s), 0.9 (3H,t).

EXAMPLE 57

9α-Hydroxy-11α,15S-bis(2-tetrahydropyranyloxy)-15-(3-ethylcyclopentyl)-16,17,18,19,20-pentanorprosta-trans-2,trans-13-dienoic acid By proceeding as described in Example 1 but replacing the methyl 9α-acetoxy-11α-(2-tetrahydropyranyloxy)-15S-hydroxy-15-(trans-4-ethylcyclohexyl)-16,17,18,19,20-pentanorprosta-cis-5,trans-13-dienoate by 201 mg. of methyl 9α-hydroxy-11α,15S-bis(2-tetrahydropyranyloxy)-15-(3-ethylcyclopentyl)-16,17,18,19,20-pentanorprosta-trans-2,trans-13-dienoate (prepared as described in Example 56) dissolved in 2.4 ml. of a mixture of ethanol and tetrahydrofuran (1:1)

and utilizing a solution of 95 mg. of potassium hydroxide in 1 ml. of water, there were obtained 136 mg. of the title compound having the following physical characteristics:

TLC (developing solvent, benzene-ethyl acetate=2:1): Rf=0.16;
IR (liquid film): $\nu$=3450, 2940, 2860, 1700, 1650, 1430, 1370, 1240, 1130, 1020, 980 cm$^{-1}$;
NMR (CDCl$_3$ solution): $\delta$=7.22 (1H,dt), 6.3 (2H,s), 5.95 (1H,d), 5.9–5.35 (2H,m), 5.0–4.6 (2H,m), 4.6–3.3 (7H,m), 3.0–1.1 (34H,m), 0.9 (3H,t).

EXAMPLE 58

9-Oxo-11α,15S-bis(2-tetrahydropyranyloxy)-15-(3-ethylcyclopentyl)-16,17,18,19,20-pentanorprosta-trans-2,trans-13-dienoic acid By proceeding as described in Example 4 but replacing the 9α-hydroxy-11α,15S-bis(2-tetrahydropyranyloxy)-15-(trans-4-ethylcyclohexyl)-16,17,18,19,20-pentanorprostacis-5,trans-13-dienoic acid by 136 mg. of 9α-hydroxy-11α,15S-bis(2-tetrahydropyranyloxy)-15-(3-ethylcyclopentyl)-16,17,18,19,20-pentanorprosta-trans-2,trans-13-dienoic acid (prepared as described in Example 57) dissolved in 5 ml. of diethyl ether and utilizing 4 ml. of the chromic acid solution, there were obtained 111 mg. of the title compound having the following physical characteristics:
TLC (developing solvent, methylene chloride-methanol=20:1): Rf=0.21;
IR (liquid film): $\nu$=3450, 2950, 2860, 1740, 1695, 1650, 1440, 1240, 1130, 1075, 1035, 1020, 975 cm$^{-1}$;
NMR (CDCl$_3$ solution): $\delta$=9.95 (1H,m), 7.25 (1H,dt), 5.95 (1H,d), 5.95–5.5 (2H,m), 5.1–4.6 (2H,m), 4.6–3.3 (6H,m), 0.9 (3H,t).

EXAMPLE 59

9-Oxo-11α,15S-dihydroxy-15-(3-ethylcyclopentyl)-16,17,18,19,20-pentanorprosta-trans-2,trans-13-dienoic acid [or 15-(3-ethylcyclopentyl)-16,17,18,19,20-pentanor-trans-$\Delta^2$-PGE$_1$]

By proceeding as described in Example 2 but replacing the 9α,15S-dihydroxy-11α-(2-tetrahydropyranyloxy)-15-(trans-4-ethylcyclohexyl)-16,17,18,19,20-pentanorprosta-cis-5,trans-13-dienoic acid by 111 mg. of 9-oxo-11α,15S-bis(2-tetrahydropyranyloxy)-15-(3-ethylcyclopentyl)-16,17,18,19,20-pentanorprosta-trans-2,trans-13-dienoic acid (prepared as described in Example 58) dissolved in a mixture of 0.5 ml. of tetrahydrofuran and 5 ml. of 65% aqueous acetic acid, there were obtained 52 mg. of the title compound as a white powder having the following physical characteristics:
melting point=135°–137° C.;
TLC (developing solvent, chloroform-tetrahydrofuran-acetic acid=10:2:1): Rf=0.37;
IR (liquid film): $\nu$=3500, 2930, 2860, 1730, 1700, 1650, 1240, 1080, 975 cm$^{-1}$;
NMR (CDCl$_3$+CD$_3$OD+CD$_3$COCD$_3$ solution): $\delta$=6.92 (1H,dt), 5.76 (1H,dt), 5.66–5.50 (2H,m), 4.3–3.6 (5H,m), 0.88 (3H,t).

EXAMPLE 60

β-Cyclodextrin clathrate of 15-(3-propylcyclopentyl)-16,17,18,19,20-pentanor-trans-$\Delta^2$-PGE$_1$ A solution of 5.46 mg. of 15-(3-propylcyclopentyl)-16,17,18,19,20-pentanor-trans-$\Delta^2$-PGE$_1$ (prepared as described in Example 54) in 1 ml. of ethanol was added to a solution of 64.88 mg. of β-cyclodextrin in 2.7 ml. of water and the mixture was stirred at room temperature for 10 minutes. The mixture was concentrated under reduced pressure to give 70 mg. of the β-cyclodextrin clathrate of the compound specified in the title. The content of 15-(3-propylcyclopentyl)-16,17,18,19,20-pentanor-trans-$\Delta^2$-PGE$_1$ in the product was 7.8%.

EXAMPLE 61

β-Cyclodextrin clathrate of 15-(trans-4-ethylcyclohexyl)-16,17,18,19,20-pentanor-PGE$_1$ A solution of 4.84 mg. of 15-(trans-4-ethylcyclohexyl)-16,17,18,19,20-pentanor-PGE$_1$ (prepared as described in Example 8) in 1 ml. of ethanol was added to a solution of 58.75 mg. of β-cyclodextrin in 2.4 ml. of water and the mixture was stirred at room temperature for 10 minutes. The mixture was concentrated under reduced pressure to give 63 mg. of the β-cyclodextrin clathrate of the compound specified in the title. The content of 15-(trans-4-ethylcyclohexyl)-16,17,18,19,20-pentanor-PGE$_1$ in the product was 7.6%.

The present invention includes within its scope pharmaceutical cmpositions which comprise at least one new therapeutically useful compound of general formula VII, or cyclodextrin clathrate thereof, or, when R represents a hydrogen atom, a non-toxic salt thereof, together with a pharmaceutical carrier or coating. In clinical practice the new compounds of the present invention will normally be administered orally, vaginally, rectally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, mannitol or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the human adult, the doses per person are generally between 5 and 5,000 µg. by oral administration in the treatment of hypertension, between 5 and 5,000 µg. by oral administration in the treatment of disorders of the peripheral circulation, between 0.1 and 50 mg. by oral administration in the prevention and treatment of cerebral thrombosis and myocardial infarction, between 0.5 and 500 µg. by oral administration in the treatment of gastric ulceration and between 0.05 and 5,000 µg. by oral, intravaginal, intrauterine, intravenous, intramuscular and extraovular administration in the termination of pregnancy and induction of labour in pregnant female mammals, in the treatment of impaired fertility and in the control of oestrus, contraception and menstrual regulation in female mammals. In domestic female mammals such as cows, mares, sows, ewes and bitches, the doses are generally between 0.01 and 50 mg. per animal by intramuscular, subcutaneous, intrauterine, intravaginal and intravenous administration for the synchronisation of oestrus, treatment of impaired fertility and the induction of abortion and labour.

The following Example illustrates pharmaceutical compositions according to the invention.

EXAMPLE 62

15-(3-Propylcyclopentyl)-16,17,18,19,20-pentanor-PGE$_1$ (2 mg.) was dissolved in ethanol (10 ml.), mixed with mannitol (18.5 g.) sieved through a 30-mesh sieve, dried at 30° C. for 90 minutes and again sieved through a 30-mesh sieve. Aerosil (microfine silica, 200 mg.) was added and the powder obtained was machine filled into one hundred No. 2 hard gelatin capsules to give capsules each containing 20 µg. of 15-(3-propylcyclopentyl)-16,17,18,19,20-pentanor-PGE$_1$, which after swallowing of the capsule is released into the stomach.

We claim:

1. Prostaglandin analogues of the formula:

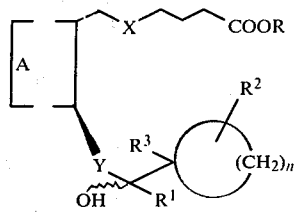

wherein A represents a grouping of the formula:

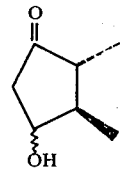

X represents ethylene, Y represents ethylene or trans-vinylene, R represents a hydrogen atom or a straight- or branched-chain alkyl group containing from 1 to 12 carbon atoms, $R^1$ represents a hydrogen atom or a methyl or ethyl group, $R^2$ represents a straight- or branched-chain alkyl group containing from 2 to 8 carbon atoms, $R^3$ represents a hydrogen atom or a straight- or branched-chain alkyl group containing from 1 to 3 carbon atoms, and n represents 4 or 5, and cyclodextrin clathrates of such acids and esters and, when R represents a hydrogen atom, non-toxic salts thereof.

2. Prostaglandin analogues according to claim 1 wherein R represents a hydrogen atom or a methyl group.

3. Prostaglandin analogues according to claim 1 wherein $R^1$ represents a hydrogen atom.

4. Prostaglandin analogues according to claim 1 in which $R^2$ represents an alkyl group of 2 to 3 carbon atoms.

5. Prostaglandin analogues according to claim 1 wherein $R^3$ represents a hydrogen atom or a methyl group.

6. Prostaglandin analogues according to claim 1 wherein the hydroxy groups in formulae VII, and VIIIB depicted in claim 1 and shown in α- or β-configuration are attached to the carbon atom in α-configuration.

7. Prostaglandin analogue according to claim 1 which is 9-oxo-11α,15S-dihydroxy-15-(trans-4-ethylcyclohexyl)-16,17,18,19,20-pentanorprost-trans-13-enoic acid.

8. Prostaglandin analogue according to claim 1 which is 9-oxo-11α,15S-dihydroxy-15-(3-propylcyclopentyl)-16,17,18,19,20-pentanorprost-trans-13-enoic acid.

9. Prostaglandin analogue according to claim 1 which is 9-oxo-11α,15S-dihydroxy-15-(3-ethylcyclopentyl)-16,17,18,19,20-pentanorprost-trans-13-enoic acid.

10. Prostaglandin analogue according to claim 1 which is 9-oxo-11α,15R-dihydroxy-15-(3-ethylcyclopentyl)-16,17,18,19,20-pentanorprostanoic acid.

11. Prostaglandin analogue according to claim 1 which is methyl 9-oxo-11α,15S-dihydroxy-15-(3-propylcyclopentyl)-16,17,18,19,20-pentanorprost-trans-13-enoate.

12. Prostaglandin analogue according to claim 1 which is methyl 9-oxo-11α,15R-dihydroxy-15(1-methyl-3-propylcyclopentyl)-16,17,18,19,20-pentanorprost-trans-13-enoate.

13. Prostaglandin analogue according to claim 1 which is methyl 9-oxo-11α,15S-dihydroxy-15-(3-ethylcyclohexyl)-16,17,18,19,20-pentanorprost-trans-13-enoate.

* * * * *